United States Patent
Van Keuren-Jensen et al.

(10) Patent No.: US 11,053,545 B2
(45) Date of Patent: Jul. 6, 2021

(54) BIOMARKERS AND METHODS OF DIAGNOSING AND PROGNOSING MILD TRAUMATIC BRAIN INJURIES

(71) Applicant: THE TRANSLATIONAL GENOMICS RESEARCH INSTITUTE, Phoenix, AZ (US)

(72) Inventors: Kendall Van Keuren-Jensen, Phoenix, AZ (US); Matthew Huentelman, Phoenix, AZ (US); Ashish Yeri, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 407 days.

(21) Appl. No.: 15/758,213

(22) PCT Filed: Sep. 8, 2016

(86) PCT No.: PCT/US2016/050810
§ 371 (c)(1),
(2) Date: Mar. 7, 2018

(87) PCT Pub. No.: WO2017/044650
PCT Pub. Date: Mar. 16, 2017

(65) Prior Publication Data
US 2018/0258483 A1    Sep. 13, 2018

Related U.S. Application Data

(60) Provisional application No. 62/215,381, filed on Sep. 8, 2015.

(51) Int. Cl.
| | |
|---|---|
| *C12Q 1/68* | (2018.01) |
| *C12Q 1/6876* | (2018.01) |
| *C12Q 1/6883* | (2018.01) |
| *G01N 33/53* | (2006.01) |

(52) U.S. Cl.
CPC ......... *C12Q 1/6876* (2013.01); *C12Q 1/6883* (2013.01); *G01N 33/5308* (2013.01); *C12Q 2600/112* (2013.01); *C12Q 2600/158* (2013.01); *C12Q 2600/178* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | |
|---|---|---|
| 2013/0022982 A1 | 1/2013 | Wang et al. |
| 2013/0060168 A1 | 3/2013 | Chu et al. |
| 2014/0147454 A1* | 5/2014 | Chakraborty .......... A61K 39/00 424/185.1 |
| 2014/0303025 A1* | 10/2014 | Van Keuren-Jensen .................... C12Q 1/6883 506/9 |

FOREIGN PATENT DOCUMENTS

WO    2014/152773 A1    9/2014

OTHER PUBLICATIONS

Handbook of Chemistry and Physics, 49th Edition, 1968, Weast (ed.), The Chemical Rubber Co., Cleveland, Ohio, p. A-245—Combination Equation.*
Lu et al, Nature 435: 834 (2005).*
Winter et al., "Argonaute-3 activates the let-7a passenger strand microRNA", RNA Biology, 10(10):1631-1643 (Oct. 2013).
Love, M. I., et al. Moderated estimation of fold change and dispersion for RNA-seq data with DESeq2. Genome Biology 2014; 15:550.
Freitas, T., et al. Accurate read-based metagenome characterization using a hierarchical suite of unique signatures. Nucleic Acids Res 2015; 43:e69.
Burgos, K. L., et al. Identification of extracellular miRNA in human cerebrospinal fluid by next-generation sequencing. RNA 2013; 19:712-722.
Hackenberg, M., et al. miRanalyzer: an update on the detection and analysis of microRNAs in high-throughput sequencing experiments. Nucl Acids Res 2011; 39:W132-W138.
Langlois, J. A., et al. The epidemiology and impact of traumatic brain injury: a brief overview. J Head Trauma Rehabil 2006; 21(5):375-378.
Alla, S., et al. Self-report scales/checklists for the measurement of concussion symptoms: a systematic review. Br J Sports Med 2009; 43(Suppl 1):i3-12.
Hutchison, J. S., et al. Impact of hypotension and low cerebral perfusion pressure on outcomes in children treated with hypothermia therapy following sever traumatic brain injury: a post hoc analysis of the Hypothermia Pediatric Head Injury Trial. Dev Neurosci 2010; 32(5-6):406-412.
Hutchison, M., et al. Differential emotional responses of varsity athletes to concussion and musculoskeletal injuries. Clin J Sport Med 2009; 19(1):13-19.
Gosselin, N., et al. Sleep following sport-related concussions. Sleep Med 2009; 10(1):35-46.
Gosselin, D., et al. MyD88 signaling in brain endothelial cells is essential for the neuronal activity and glucocorticoid release during systemic inflammation. Mol Psychiatry 2008; 13(5):480-497.
Wilusz, J. E., et al. Long noncoding-RNAs: functional surprises from the RNA world. Genes Dev 2009; 23(13):1494-1504.
Wilusz, J. RNA stability: is it the endo' the world as we know it? Nat Struct Mol Biol 2009; 16(1):9-10.
Moran, A., et al. Re-imagining motor imagery: building bridges between cognitive neuroscience and sport psychology. Br J Psychol 2012; 103(2):224-247.

(Continued)

*Primary Examiner* — James Martinell
(74) *Attorney, Agent, or Firm* — Rodney J. Fuller; Booth Udall Fuller, PLC

(57) ABSTRACT

The invention provides microRNA markers and methods for determining the risk a subject has for developing mild traumatic brain injuries (mTBI). In some aspects, the methods further include determine the fitness of a subject for participating in an activity with increased chances of receiving a head impact. Certain embodiments are directed to kits designed for these purposes.

5 Claims, No Drawings

(56) References Cited

OTHER PUBLICATIONS

Taft, R. J., et al. Non-coding RNAs: regulators of disease. J Pathol 2010; 220(2):126-139.
Casalini, P., et al. MicroRNAs and future therapeutic applications in cancer. J BUON 2009; 14(Suppl 1):S17-22.
Iorio, L., et al. N-terminal pro-brain natriuretic peptide determination as possible marker of cardiac dysfunction in patients with adrenal disorders. J Endocrinol Invest 2010; 33(7):509-510.
Iorio, L., et al. Neurological picture. Pseudoperipheral tongue weakness. J Neurol Neurosurg Psychiatry 2010; 81(9):1024-1025.
Iorio, M. V., et al. Interplay between microRNAs and the epigenetic machinery: an intricate network. Biochimica et Biophysica Acta 2010; 1799(10-12):694-701 doi: 10.1016/j.bbagrm.2010.05.005. Epub May 20, 2010.
Schratt, G. microRNAs at the synapse. Nat Rev Neurosci 2009; 10(12):842-849.
Schratt, G. Fine-tuning neural gene expression with microRNAs. Curr Opin Neurobiol 2009; 19(2):213-219.
Rosa, A., et al. MicroRNAs in early vertebrate development. Cell Cycle 2009; 8(21):3513-3520.
Rosa, A., et al. The miR-430/427/302 family controls mesendodermal fate specification via species-specific target selection. Dev Cell 2009; 16(4):517-527.
Mercer, S. L, et al. Study designs for effectiveness and translation research: identifying trade-offs. Am J Prev Med 2007; 33(2):139-154.
Mercer, A., et al. Characterization of neurons in the CA2 subfield of the adult rat hippocampus. J Neurosci 2007; 27(27):7329-7338.
Barbato, C., et al. Searching for MIND: microRNAs in neurodegenerative diseases. J Biomed Biotechnol 2009; 2009:871313.
Li, Y., et al. Brain anatomical network and intelligence. PLoS Comput Biol 2009; 5(5):e1000395.
Olsen, L., et al. MicroRNAs show mutually exclusive expression patterns in the brain of adult male rats. PLoS One 2009: 4(10):e7225.
Taft, R.J., et al. Nuclear-localized tiny RNAs are associated with transcription initiation and splice sites in metazoans. Nat Struct Mol Biol 2010; 17(8):1030-1034.
Yin, X., et al. Brain endothelial cells synthesize neurotoxic thrombin in Alzheimer's disease. Am J Pathol 2010; 176(4):1600-1606.
Lei, H., et al. Evolution of the neurochemical profile after transient focal cerebral ischemia in the mouse brain. J Cereb Blood Flow Metab 2009; 29(4):811-819.
Lei, P., et al. Microarray based analysis of microRNA expression in rat cerebral cortex after traumatic brain injury. Brain Res 2009; 12884:191-201.
Lei, B., et al. Effects of midazolam on brain injury after transient focal cerebral ischemia in rats. J Neurosurg Anesthesiol 2009; 21(2):131-139.
Breiman, L. Random Forests. Machine Learning 2001; 45(1): 5-32.
Tan, A. A., et al. Strain differences in response to traumatic brain injury in Long-Evans compared to Sprague-Dawley rats. J Neurotrauma 2009; 26(4):539-548.
Tan, Z. Neural protection by naturopathic compounds—an example f tetramethylpyrazine from retina to brain. J Ocul Biol Dis Infor 2009; 2(2):57-64.
Dienel, G. A. Lactate shuttling and lactate use as fuel after traumatic brain injury: metabolic considerations. Journal of Cerebral Blood Flow and Metabolism 2014; 34:1736-1748.
Satrustegui, J., et al. Role of aralar, the mitochondrial transporter of aspartate-glutamate, in brain N-acetylaspartate formation and Ca(2+) signaling in neuronal mitochondria. Journal of Neuroscience Research 2007; 85:3359-3366.
Di Pietro, V., et al. Potentially neuroprotective gene modulation in an in vitro model of mild traumatic brain injury. Molecular and Cellular Biochemistry 2013; 375:185-198.
Sinasac, D., et al., Slc25a13-Knockout Mice Harbor Metabolic Deficits but Fail to Display Hallmarks of Adult-Onset Type II Citrullinemia. Molecular and Cellular Biology 20004; 24(2):527-536.

Scafidi, S., et al. Delayed cerebral oxidative glucose metabolism after traumatic brain injury in young rats. Journal of Neurochemistry 2009; 109(1):189-197.
McCrory, P., et al. Consensus Statement on Concussion in Sport— the 3rd International Conference on Concussion in sport held in Zurich, Nov. 2008. SAJSM 2009; 21(2):36-46.
Broglio, S. P., et al. The effect of sport concussion on neurocognitive function, self-report symptoms and postural control: a meta-analysis. Sports Med 2008; 38(1):53-67.
Suskiewicz, Kevin M. Postural Stability Assessment Following Concussion: One Piece of the Puzzle. Clinical Journal of Sport Medicine 2001; 11:182-189.
McCrea, M., et al. Acute effects and recovery time following concussion in collegiate football players; the NCAA Concussion Study. JAMA 2003; 290(19):2556-2563.
Guskiewicz, K. M., et al. Recurrent concussion and risk of depression in retired professional football players. Med Sci Sports Exerc 2007; 39(6):903-909.
Van Donkelaar, P., et al. Attentional deficits in concussion. Brain Injury 2005; 19(12):1031-1039.
Kosik, Kenneth S. The neuronal microRNA system. Nature Reviews Neuroscience 2006; 7:911-920.
Nelson, P. T., et al. In situ hybridization is a necessary experimental complement to microRNA (miRNA) expression profiling in the human brain_ Neuroscience Letters 2009; 466(2):69-72.
Fineberg, S. K., et al. MicroRNAs Potentiate Neural Development. Neuron 2009; 64(3):303-309.
Eacker, S. M., et al. Understanding microRNAs in neurodegeneration. Nat Rev Neurosci 2009; 10(12):837-841.
Dharap, A., et al. Transient Focal Ischemia Induces Extensive Temporal Changes in Rate Cerebral MicroRNAome. Journal of Cerebral Blood Flow & Metabolism 2009; 29(4):675-687.
Rowson, et al. Brain Injury Prediction: Assessing the Combined Probability of Concussion Using Linear and Rotational Head Acceleration. Ann of Biomed. Engg 2013; 41(5):873-882.
Raposo, G., et al. Extracellular vesicles: exosomes, microvesicles, and friends. J Cell Biol 2013; 200(4):373-383.
Colombo, M., et al. Biogenesis, secretion, and intercellular interactions of exosomes and other extracellular vesicles. Annu Rev Cell Dev Biol 2014; 30:255-289.
Yanez-Mo, M., et al. Biological properties of extracellular vesicles and their physiological functions. J Extracell Vesicles 2015: 4:27066.
Minciacchi, V., et al. Extracellular vesicles in cancer: exosomes, microvesicles and emerging role of large oncosomes. Semin Cell Dev Biol 2015; 40:41-51.
Vickers, K., et al. MicroRNAs are transported in plasma and delivered to recipient cells by high-density lipoproteins. Nat Cell Biol 201; 13:423-433.
Arroyo, J., et al. Argonaute2 complexes carry a population of circulating microRNAs independent of vesicles in human plasma. Proc Natl Acad Sci 2011; 108:5003-5008.
Turchinovich, A., et al. Characterization of extracellular circulating microRNA. Nucleic Acids Res 2011; 39:7223-7233.
Margue, C., et al. Comparison of a healthy miRNome with melanoma patient miRNomes: are microRNAs suitable serum biomarkers for cancer? Oncotarget 2015; 6(14):12110-12127.
Yuan, T., et al. Plasma extracellular RNA profiles in healthy and cancer patients. Sci Rep 2016; 20:19413.
Freedman, J., et al. Diverse human extracellular RNAs are widely detected in human plasma. Nat Commun 2016; 7:11106.
Ben-Dov, I., et al. Cell and Microvesicle Urine microRNA Deep Sequencing Profiles from Healthy Individuals: Observations with Potential Impact on Biomarker Studies. PLoS One 2016; 11:e0147249.
Fehlmann, T., et al. Distribution of microRNA biomarker candidates in solid tissues and body fluids. RNA Biol 2016; 13:1084-1088.
Hecksteden, A., et al. miRNAs and sports: tracking training status and potentially confounding diagnoses. J Transl Med 2016; 14:219.
Meiri, E., et al. Discovery of microRNAs and other small RNAs in solid tumors. Nucleic Acids Res 2010; 38:6234-6246.
Dhahbi, J. 5' tRNA Halves: The Next Generation of Immune Signaling Molecules. Front Immunol 2015; 6:74.

(56) References Cited

OTHER PUBLICATIONS

Dhahbi, J., et al. Deep Sequencing of Serum Small RNAs Identifies Patterns of 5' tRNA Half and YRNA Fragment Expression Associated with Breast Cancer. Biomark Cancer 2014; 6:37-47.

Dhahbi, J., et al. 5'-YRNA fragments derived by processing of transcripts from specific YRNA genes and pseudogenes are abundant in human serum and plasma. Physiol Genomics 2013; 45:990-998.

Chakrabortty, S., et al. Extracellular vesicle-mediated transfer of processed and functional RNY5 RNA. RNA 2015; 21:1966-1979.

Tosar, J., et al. Assessment of small RNA sorting into different extracellular fractions revealed by high-throughput sequencing of breast cell lines. Nucleic Acids Res 2015; 43:5601-5616.

Van Balkom, B. W., et al. Quantitative and qualitative analysis of small RNAs in human endothelial cells and axosomes provides insights into localized RNA processing, degradation and sorting. J Extracell Vesicles 2015; 4:26760.

Nicolas, F. E., et al. Biogenesis of Y RNA-derived small RNAs is independent of the microRNA pathway. FEBS Lett 2012; 586:1226-1230.

Fritz, J. V. et al. Sources and Functions of Extracellular Small RNAs in Human Circulation. Annu Rev Nutr 2016; 36:301-336.

Stein, A. J., et al. Structural insights into RNA quality control: the Ro autoantigen binds misfolded RNAs via its central cavity. Cell 2015; 121:529-539.

Zhang, A. T., et al. Dynamic interaction of Y RNAs with chromatin and initiation proteins during human DNA replication. J Cell Sci 2011; 124:2058-2069.

Kirchner, S., et al. Emerging roles of tRNA in adaptive translation, signalling dynamics and disease. Nat Rev Genet 2015; 16:98-112.

Goodarzi, H., et al. Endogenous tRNA-Derived Fragments Suppress Breast Cancer Progression via YBX1 Displacement. Cell 2015; 161:790-802.

Cozen, S., et al. ARM-seq: AlkB-facilitated RNA methylation sequencing reveals a complex landscape of modified RNA fragments. Nat Methods 2015; 12:879-884.

Zheng, G., et al. Efficient and quantitative high-throughput tRNA sequencing. Nat Methods 2015; 12:835-837.

Patton, J. G., et al. Biogenesis, delivery, and function of extracellular RNA. J Extracell Vesicles 2015; 4:27494.

Siomi, M. C., et al. PIWI-interacting small RNAs: the vanguard of genome defence. Nat Rev Mol Cell Biol 2011; 12:246-258.

Morris, K. V., et al. The rise of regulatory RNA. Nat Rev Genet 2014; 15:423-437.

Thompson, D., et al. tRNA cleavage is a conserved response to oxidative stress in eukaryotes. RNA 2008; 14:2095-2103.

Thompson, D. M., et al. Stressing out over tRNA cleavage. Cell 2009; 138:215-219.

Ivanov, P., et al. Angiogenin-Induced tRNA Fragments Inhibit Translation Initiation. Molecular Cell 2011; 43:613-623.

Anderson, P., et al. tRNA fragments in human health and disease. FEBS Letters 2014; 588:4297-4304.

Pang, Y., et al. Diverse cell stresses induce unique patterns of tRNA up- and down-regulation: tRNA-seq for quantifying changes in tRNA copy number. Nucleic Acids Research 2014; 42:e170.

Lee, Y. S., et al. A novel class of small RNAs: tRNA-derived RNA fragments (tRFs). Genes and Dev 2009; 23:2639-2649.

Kumar, P., et al. tRFdb: a database for transfer RNA fragments. Nucl Acids Res 2015; 43:D141-D145.

Bhomia, Manish et al., "A Panel of Serum MiRNA Biomarkers for the Diagnosis of Severe to Mild Traumatic Brain Injury in Humans", Scientific Reports, 6(1):1-12 (Sep. 1, 2016).

Redell, John B. et al., "Human Traumatic Brain Injury Alters Plasma microRNA Levels", Journal of Neurotrauma, 27:2147-2156 (Dec. 2010).

Sharma, Anuj et al., "Identification of Serum MicroRNA Signatures for Diagnosis of Mild Traumatic Brain Injury in a closed Head Injury Model", PLOS ONE, 9(11):e112019 (Nov. 7, 2014).

* cited by examiner

BIOMARKERS AND METHODS OF DIAGNOSING AND PROGNOSING MILD TRAUMATIC BRAIN INJURIES

RELATED APPLICATION DATA

This application is the U.S. National Stage of International Application No. PCT/US2016/050810, filed Sep. 8, 2016, which claims priority to and the benefit of U.S. Provisional Application No. 62/215,381 filed Sep. 8, 2015, the contents of each of which are hereby incorporated by reference in their entireties.

FIELD OF THE INVENTION

The present invention is related to biomarkers and methods for determining the risk of a subject for developing mild traumatic brain injuries (mTBI). In some aspects, embodiments of the invention are directed to kits and apparatuses.

BACKGROUND OF THE INVENTION

Despite significant benefits to the physical, mental, and social development of adolescents and young adults participating athletics, sport-related injuries are a significant risk in this population. Particularly, playing contact sports such as football and hockey involves a significant risk of brain injury due to impact to the head. During such physical activity, the head or other body part of the individual is often subjected to direct contact to the head, which results in impact to the skull and brain of the individual as well as movement of the head or body part itself. Sport-related concussion is the most commonly cited athletic injury in the lay and professional literature during the past decade. These injuries are a significant public health issue because of concerns with the developing brain following head trauma, recurrent and cumulative effects of concussion, recovery following concussion, as well as more global issues concerning academic performance and psychosocial issues.

The Center for Disease Control and Prevention (CDC) estimates estimated that 1.6 to 3.8 million sport-related concussion injuries occurring annually and that the incidence of sports-related mild traumatic brain injury (mTBI) approaches 300,000 annually in the United States. It is not uncommon that a typical range of concussions per year for a football team of 90 players is 4-6 (7%) and for a hockey team with 28 players is 6 (21%). In rugby, concussion can affect as many as 40% of players on a team each year. Approximately a third of these injuries occur in football. Head injuries accounted for 13.3% of all football injuries to boys and 4.4% of all soccer injuries to both boys and girls in a large study of high school sports injuries. Approximately 62,800 mTBI cases occur annually among high school varsity athletes, with football accounting for about 63% of cases. Concussions in hockey affect 10% of the athletes and make up 12%-14% of all injuries.

The CDC statistics on mTBI does not even include such incidences in the United States Armed Forces. In the army, the incidence of TBI in the armed forces is around 20,000 annually, and for the Navy, Air Force, and the Marines, the incidence of TBI for each branch is around 2,500 annually.

Concussions, particularly when repeated multiple times, significantly threaten the long-term health of the person. The health care costs associated with mTBI in sports are estimated to be in the hundreds of millions annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Sport-related concussion has been linked to various markers of health, including an increase in symptom reports, cognitive deficits, balance impairments, as well as depression, mood disturbances, sleep disturbances, and attention/concentration issues, which are all mediators that may affect one's perception of their quality of life. While there have been great strides in the evaluation of clinical assessment tools for evaluating the concussed athlete, concussion remains a clinical diagnosis based primarily on self-reported signs and symptoms, cognitive deficits, and balance impairments. These tools are helpful in tracking recovery post-injury, but they rely on self-reporting by an individual who is motivate to remain participating in sport and lack the sensitivity to be a diagnostic tool.

The health risks of subsequent head impact increases significantly, for example subsequent impacts following an initial concussion (mTBI) may be 4-6 times more likely to result in a second, often more severe, brain injury. Although increased brain tissue strain, pressure waves, and pressure gradients within the skull have been linked with specific brain injury mechanisms, much remains unknown about the response of the brain to head impacts. There is even less known about the correspondence between specific impact forces and injury, particularly with respect to injuries caused by repeated exposure to impact forces of a lower level than those that result in a catastrophic injury or fatality.

Detecting changes that are a direct result of head impact and mild traumatic brain injury are challenging. Conventional imaging techniques are usually insufficient to identify damage associated with mTBI. However, the presence of lingering symptoms indicates that functional changes resulting from repeated and/or acute exposure to head impact do occur and can typically last several days. These functional changes possibly result from structural damage to torn axons and synaptic connections and inflammation. Therefore, there is an opportunity to detect either physical injury and/or repair processes going on in the brain as a head impact that do not result in a concussion diagnosis or only result in mTBI. Unfortunately, there is limited data on the molecular changes associated with mTBI or from the effect repeated head impacts that do not result in a diagnosis of concussion such as those that occur during routine practices and games of contact sports.

SUMMARY OF THE INVENTION

Certain embodiments of the invention are directed to methods of determining the risk of a subject developing mTBI. The methods generally include obtaining a biological sample from a subject; measuring the biological sample for an amount of at least one microRNA marker selected from the group consisting of the biomarkers selected from biomarkers listed in any one of Tables 1-65; and comparing the amount of the at least microRNA marker with the amount of the at least one microRNA marker in a control biological sample, wherein a change in the amount of the at least one microRNA marker from the subject compared with the control is indicative of the subject having an increased risk for mTBI.

Other embodiments of the invention are directed to methods or determining the fitness of a subject to participate in a activity with increased chances of receiving a head impact. The method typically includes obtaining a biological sample from a subject; measuring the biological sample for an amount of at least one microRNA marker selected from biomarkers listed in any one of Tables 1-65; and comparing the amount of the at least one microRNA marker with the amount of the at least one microRNA marker in a control sample; and wherein a change in the amount of the at least one microRNA marker from the subject compared with the control is indicative of the subject being unfit for participating in the activity with increased chances of receiving a head impact.

Certain implementations of the methods of the invention comprise measuring the biological sample for an amount of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at 25, at least 30, at least 35, at least 40, at least 45, or at least 50 biomarkers selected from biomarkers listed in any one of Tables 1-65.

In some aspects, the biological sample is obtained after the subject has received a head impact incident, for example within 48 hours, within 24 hours, within 12 hours, or within 6 hours of the subject having had a head impact incident or is suspected of having a head impact incident.

The invention also provides kits for determining the risk of a subject for developing mTBI or for determining the fitness of a subject for participating in an activity with increased chances of receiving a head impact, wherein the kits detect the expression of at least one microRNA marker selected from the biomarkers listed in any one of Tables 1-65. In some embodiments, the kit comprises a primer or probe that specifically determines the expression level of at least one microRNA marker selected from any one of Tables 2-65 in the subject. The kits may further comprise a dataset comprising the expression level of the at least one microRNA marker in normal subjects and/or a control sample. In some aspects, the kits may further comprise a DNA polymerase and a buffer. In other aspects, the probe is covalently attached to the surface of a solid support.

The kits may further comprise instructions listing the direction of change in the expression of the at least one microRNA marker in the subject in relation to the dataset or the control that demonstrates the subject has increased risk of the subject for developing mTBI. In some embodiments, the direction of change in the expression corresponds to the changes as depicted in any one of Tables 2-41.

The kits also may be designed to determine the probability score for a subject's exposure to potentially injurious head impact. Such kits comprise a primer or probe that specifically determines the expression level of at least one microRNA marker selected from any one of Tables 38-41, 48-53, and 60-65 and a control sample or a dataset comprising the expression level of the at least one microRNA marker in normal subjects. Correlating the direction of change in the expression of the at least one microRNA marker with the direction of change as depicted in any one of Tables 38-41 determines the subject's probability score for a subject's risk for concussion or exposure to potentially injurious head impact.

Additional objectives, advantages and novel features will be set forth in the description which follows or will become apparent to those skilled in the art upon examination of the drawings and detailed description which follows.

DETAILED DESCRIPTION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, the term "acute head injury" refers to head injury received by subjects who do not have a history of chronic cumulative head impact exposure. For example, the subject may play non-contact sports.

As used herein, the term, "biological sample," includes blood samples, salivary samples, and urine samples. However, other biological samples are also contemplated, for example, cerebral spinal fluid samples, plasma samples, and tear samples. Thus biological sample, as used herein, refers to biological fluids (biofluids) of the subject.

As used herein, the term "head impact," refers generally to measurable impact to the head.

As used herein, the term "expression" in relation to biomarkers refers both genetic expression and protein expression. Measuring genetic expression includes measuring the expression of DNA and/or RNA, including measuring non-coding RNA molecules such as microRNAs. Such measurements include measuring extracellular RNA expression. Measuring protein expression includes measuring the presence of whole proteins and/or peptides. For RNA expression, a microRNA marker is considered expressed if a sample has at least 10 read counts of the microRNA.

The invention relates to the discovery that contact sports athletes who recently had or did not have any head impact incidents have unique microRNA expression profiles. Furthermore, the uniqueness of the microRNA profiles can be distinguish based on the force of the head impact (as measured by linear or rotational acceleration or an impact score such as HITsp from helmets made by Riddell), the number of hits, and the frequency of the head impact. Thus, the invention provides microRNA markers for determining the risk of a subject for developing mTBI and/or concussion. In some aspects, the disclosed microRNA markers have been found to be significant in at least four comparisons.

Table 1 lists the microRNAs, where changes in their expression in plasma, urine, and/or saliva samples of a subject can determine whether the subject is at risk for developing mTBI and/or concussion. In some aspects, the microRNA markers of Table 1 were significant from linear regression of seven categories of the players' impact data from the helmets on the RNA expression. The seven categories are (1) total number of all head impacts sustained by the player in the game (Total_Hits); (2) highest impact sustained by the player in the game as measured by linear acceleration sustained by the head (Max_Lin_acc); highest impact sustained by the player in the game as measured by the rotational acceleration (Max_Rot_acc); highest impact sustained by the player in the game as measured by a combined score (HITsp) of the location of impact, linear and rotational acceleration (Max_HITsp); sum of all impacts sustained by the player in the game as measured by linear acceleration sustained by the head (Cum_Lin_acc); sum of all impacts sustained by the player in the game as measured by the rotational acceleration (Cum_Rot_acc); and sum of all impacts sustained by the player in the game as measured by a combined score (HITsp) of the location of impact, linear and rotational acceleration (Cum_HITsp). In some aspects, microRNA markers of Table 1 were significant from differential expression analysis between:

- Samples from players with a diagnosed concussion (Concussion) and samples acquired from players before the competitive season began (Baseline);
- Samples from players with a diagnosed concussion (Concussion) and samples acquired from players who were hit greater than or equal to 60 times the previous day (High_freq_hits);
- Samples from players with a diagnosed concussion (Concussion) and samples acquired from players who were hit less than or equal to 15 times the previous day (Low_freq_hits);
- Samples from players with a diagnosed concussion (Concussion) and samples acquired from players who sustained a hit with HITsp of greater than or equal to 85 the previous day (Max_hitsp);
- Samples from players with a diagnosed concussion (Concussion) and samples acquired from players who sustained a hit with HITsp of less than or equal to 30 the previous day (Min_hitsp);
- High_freq_hits and Low_freq_hits;
- High_freq_hits and Baseline;
- Low_freq_hits and Baseline;
- Max_hitsp and Min_hitsp;
- Max_hitsp and Baseline;
- Min_hitsp and Baseline;
- Samples from subjects with mild exposure to potentially injurious head impact (probability score of 0-0.1) and samples from subjects with least exposure to potentially injurious head impact (probability score of 0);
- Samples from subjects with moderate exposure potentially injurious head impact (probability score of 0.1-0.5) and samples from subjects with least exposure potentially injurious head impact (probability score of 0);
- Samples from subjects with moderate exposure potentially injurious head impact (probability score of 0.1-0.5) and samples from subjects with mild exposure potentially injurious head impact (probability score of 0-0.1);
- Samples from subjects with high exposure potentially injurious head impact (probability score of >0.5) and samples from subjects with least exposure potentially injurious head impact (probability score of 0);
- Samples from subjects with high exposure potentially injurious head impact (probability score of >0.5) and samples from subjects with mild exposure potentially injurious head impact (probability score of 0-0.1); and
- Samples from subjects with high exposure potentially injurious head impact (probability score of >0.5) and samples from subject with moderate exposure potentially injurious head impact (probability score of 0.1-0.5).

In comparisons using the probability score for risk of concussion or exposure to potentially injurious head impact, the scores are calculated using the linear and rotational acceleration was studied previously by Rowson et al. ("Brain Injury Prediction: Assessing the Combined Probability of Concussion Using Linear and Rotational Head Acceleration." *Ann of Biomed. Engg* 2013).

Tables 2-13 list microRNA markers and the type of change in their expression for determining the risk of the subject for developing mTBI and/or concussion using the subject's blood sample, preferably the subject's plasma sample. Specifically, Tables 2 and 3 list the microRNA markers for determining risk based Cum_HITsp. Tables 4 and 5 list the microRNA markers for determining risk based Cum_Lin_acc. Table 6 lists the microRNA markers for determining risk based on Cum_Rot_acc. Tables 7 and 8 list the microRNA markers for determining risk based on Max_Lin_acc. Table 9 lists the microRNA markers for determining risk based Max_Rot_acc. Tables 10 and 11 lists the microRNA markers for determining risk based on Max_HITsp. Tables 12 and 13 lists the microRNA markers for determining risk based Total_Hits. Results are shown for three levels of stringency as determined by the percentage of measurable expression of these markers in the samples.

Tables 14-25 list microRNA markers and the type of change in their expression for determining the risk of the subject for developing mTBI and/or concussion using the subject's urine sample. Specifically, Tables 14 and 15 list the microRNA markers for determining risk based on Cum_HITsp. Tables 16 and 17 list the microRNA markers for determining risk based on Cum_Lin_acc. Tables 18 and 19 list the microRNA markers for determining risk based on Max_Lin_acc. Tables 20 and 21 list the microRNA markers for determining risk based on Max_Rot_acc. Tables 22 and 23 list the microRNA markers for determining risk based on Max_HITsp. Tables 24 and 25 list the microRNA markers for determining risk based on Total_Hits. Results are shown for three levels of stringency as determined by the percentage of measurable expression of these markers in the samples.

Tables 26-31 list microRNA markers and the type of change in their expression for determining the risk of the subject for developing mTBI and/or concussion using the subject's saliva sample. Specifically, Table 26 lists the microRNA markers for determining risk based on Cum_HITsp. Table 27 lists the microRNA markers for determining risk based on Cum_Lin_acc. Table 28 lists the microRNA markers for determining risk based on Max_Lin_acc. Table 29 lists the microRNA markers for determining risk based on Max_Rot_acc. Table 30 lists the microRNA markers for determining risk based on Max_HITsp. Table 31 lists the microRNA markers for determining risk based on Total_Hits. Results are shown for three levels of stringency as determined by the percentage of measurable expression of these markers in the samples.

Tables 32-41 list the microRNA markers that a differentially expressed in blood, preferably plasma, or urine samples that can be used for determining the risk of a subject for developing mTBI and for concussion. Tables 32 and 33 list markers from plasma and urine samples, respectively, where the analysis focuses on samples from players diagnosed with a concussion. Tables 34 and 35 list markers from plasma samples where the analysis focuses on the number of the times a player was hit or on the impact score sustained by the player. Tables 36 and 37 list markers from urine samples where the analysis focuses on the number of the times a player was hit or on the impact score sustained by the player. Tables 38 and 39 list markers from plasma samples where the analysis focuses the subjects' probability score for the risk of concussion or exposure to potentially injurious head impact. Tables 40 and 41 list markers from urine samples where the analysis focuses the subjects' probability score for the risk of concussion or exposure to potentially injurious head impact.

The invention also provides methods for determining the risk of a subject for developing mTBI and/or concussion. The methods comprise obtaining a biological sample from a subject; measuring the biological sample for an amount of at least one microRNA marker selected from the group consisting of the microRNA markers listed in Tables 1-65; and comparing the amount of the at least one microRNA marker in the biological sample with the amount of the at least one microRNA marker in a control sample, wherein a change in the amount of the at least one microRNA marker from the subject compared with the control sample is indicative of the subject being at an increased risk for developing mTBI and/or concussion. In some aspects, the microRNA markers detect the risk of developing mTBI and/or concussion after a head impact incident.

The invention also provides methods for determining the fitness of a subject for participating in an activity with increased chances of receiving a head impact. The methods comprise obtaining a biological sample from a subject; measuring the biological sample for an amount of at least one microRNA marker selected from the group consisting of the microRNA markers listed in Tables 1-65; and comparing the amount of the at least one microRNA marker with the amount of the at least one microRNA marker in a control sample, wherein a change in the amount of the at least one microRNA marker from the subject compared with the control is indicative of the subject being unfit for participating in the activity with increased chances of receiving a head impact.

In some aspects, the methods of the invention further comprises determining, based on the microRNA marker measurement, whether the subject should be hospitalized for the head impact incident, whether the subject should be monitored while continuing or halting the activity that resulted in the head impact, or the whether the subject incurred no significant increases in risk for developing mTBI due to the head impact incident.

In some aspects, measuring the biological sample of the methods of the invention comprises measuring the biological sample for an amount of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least 25, at least 30, at least 35, at least 40, at least 45, or at least 50 microRNA markers selected from the group consisting of the microRNA markers listed in Tables 1-65.

In a preferred implementation, the microRNA marker measured for determining a subject's risk for developing mTBI and/or concussion due to an incident involving head impact is selected from microRNA markers with measurable expression in at least 80% of the samples. In some aspects, the microRNAs marker measured is selected from microRNAs markers for determining risk based on Max_HITsp (Table 10, 11, 22, 23, or 30), Max_Lin_acc (Table 7, 8, 18, 19, or 28), and/or Total_Hits (Table 12, 13, 24, 25, or 31). In preferred embodiments, the biological sample is plasma.

In some embodiments of the invention, the biological sample from a subject is obtained after known head impact, for example head impact that is detected by helmet, such as one by Riddell. In some aspects, the biological sample may be collected immediately after known head impact or within one hour, three hours, six hours, eight hours, 12 hours, 18 hours, 24 hours, or 48 hours after known head impact. The biological sample may also be collected at least one hour, at least three hours, at least six, at least eight hours, at least 12 hours, at least 18 hours, or at least 24 hours after known head impact.

In some implementations, the control sample is the baseline sample of the subject. The baseline sample of the subject may be collected prior the immediate head trauma, which may or may not reflect a history of frequent head impacts, such as in athletes playing contact sports. For example, the baseline sample of a football player collected before the start of the athlete's competitive season or during the practice week may reflect a baseline comprising changes due to the subject having a history of frequent head impacts. Though if the baseline sample of a football player were collected before the start of the athlete's first competitive season or if the baseline sample were from a subject not participating in contact sports, the baseline sample would not reflect a baseline comprising such changes.

In other implementations, the control sample is not the baseline sample of the subject. For example, the control sample may be a matched sample (for example by age and sex) from a different subject or a predicted control sample calculated from the general population. The predicted control sample may be further made representative by characterizing the general population by age. Thus, prepubescent athletes and post-pubescent athletes would have separate predicted control samples. The representative sample for the general population of post-pubescent athletes may be further refined by sex and additional age brackets, for example, for a population of males between the ages of 18 to 24, females between the ages of 18 to 24, males between the ages of 25 to 30, females between the ages of 25 to 30, males between the ages of 30 to 40, or females between the ages of 30 to 40.

Methods for measuring the biological sample for an amount of at least one microRNA marker are well established in the art. Such methods include detection of the at least one microRNA marker by reacting the biological sample with primers to detect gene expression. Particular methods for measuring the biological sample for an amount of at least one microRNA marker include PCR, real-time PCR, and gene arrays.

When more than one microRNA marker is measured, the determination of the risk of a subject for developing mTBI may be based on a uniform increase in the expression of a set of microRNA markers selected from the microRNA markers listed in any one of Tables 1-65, a uniform decrease in the expression of a set of microRNA markers selected from the microRNA markers listed in any one of Tables 2-65, or a combination of increased expression of some microRNA markers listed in any one of Tables 2-65 and decrease expression of other microRNA markers listed in any one of Tables 2-65.

For example, an increased risk may be reflected by the detection of increased expression in the measured microRNA markers. An increased risk may also be reflected by the detection of decreased expression in the measured microRNA markers. An increased risk may additionally be reflected by the detection of decreased expression in some of the measured microRNA markers in combination with the detection of increased expression in the other measured microRNA markers. In some implementations, the determination of the risk of a subject for developing mTBI may be based a combination of microRNA marker listed in any one of Tables 1-65 having increased expression, decreased expression, and no change in expression.

Gradations of risk may also be determined by comparing the amount of the at least one microRNA marker in the biological sample with the amount of the at least one microRNA marker in a control sample. The magnitude of the change in expression is correlated to increased or decreased risk of the subject developing mTBI and/or concussion. The combination of particularly changes or lack of change in the expression of microRNA marker is also correlated to increased or decreased risk of the subject developing mTBI and/or concussion.

The invention further encompasses kits for determining the risk of a subject for developing mTBI or for determining the fitness of a subject for participating in an activity with increased chances of receiving a head impact, wherein the kits detect the expression of at least one microRNA marker selected from the microRNA markers listed in any one of Tables 1-65. In some embodiments, the kit comprises a primer or probe that specifically determines the expression level of at least one microRNA marker selected from any one of Tables 1-65 in the subject. In some implementations, the probe is covalently attached to the surface of a solid support. The kits may further comprise a dataset comprising the expression level of the at least one microRNA marker in normal subjects and/or a control sample.

The kits may further comprise instructions listing the direction of change in the expression of the at least one microRNA marker in the subject in relation to the dataset or the control that demonstrates the subject has increased risk of the subject for developing mTBI. In some embodiments, the direction of change in the expression corresponds to the changes as depicted in any one of Tables 2-41.

In some embodiments, the kits determine the probability of a subject's exposure to potentially injurious head impact, for example least exposure (probability score of 0), mild exposure (probability score of 0-0.1), moderate exposure (probability score of 0.1-0.5), and high exposure (probability score of >0.5). Such kits comprise a primer or probe that specifically determines the expression level of at least one microRNA marker selected from Tables 38-41, 48-53, or 60-65 and a control sample or a dataset comprising the expression level of the at least one microRNA marker in normal subjects. Correlating the change in the expression of the at least one microRNA marker with the changes as depicted in Tables 38-41 determines the subject's probability score exposure to potentially injurious head impact.

In some aspects, the kits provide rapid onsite determination of the risk of a subject for developing mTBI. An example of such a kit comprises a detection agent for at least one microRNA marker at least one microRNA marker selected from the group consisting of the microRNA markers listed in any one of Tables 1-65 and reagents facilitating the detection of the at least one microRNA marker. The detection agent may be antibodies that recognize the at least one microRNA marker, which can be fluorescence-conjugated. The detection agent may also be a nucleotide sequence that recognize the at least one microRNA marker. Reagents facilitating the detection of the at least one microRNA marker by using the aforementioned detection agents are well known in the art. In some embodiments, the kits may comprise a DNA polymerase and a buffer.

Examples

It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

1. Linear Regression of microRNA Expression in Blood, Urine, and Saliva Samples in Relation to Head Impact Data
   Methods:
   Circulating RNA from plasma, urine and saliva samples from players on game days were sequenced by next generation sequencing using the Illumina HISeq 2500. For the small-RNA sequencing in year one, only those samples which had at least 100,000 miRNA counts each were allowed in to the linear regression analysis, which gives 30 plasma, 7 saliva samples and 13 urine samples. With year one and year two samples combined, there were 360 samples sequenced in all for small RNA, which consisted of 165 plasma, 34 saliva and 161 urine samples. The cut-off employed for sample selection was that each sample have at least 1 million input reads with 5%, 0.5% and 0.5% of the reads mapped to the genome going to mature miRNAs in plasma, saliva, and urine samples respectively.

All the analyses conducted were with respect to the player's hit data on the previous day. Since no new saliva samples were sequenced from year 2, the analyses are restricted to plasma and urine only.

Simple linear regression was performed where the players' impact data from the Riddell (Chicago, Ill., USA) helmets were regressed up on the RNA expression measured in counts which have been normalized for sequencing depth between the samples. The seven categories of impact data regressed are:

1) The total number of all head impacts sustained by the player in the game (Total_Hits);
2) The highest impact sustained by the player in the game as measured by linear acceleration sustained by the head (Max_Lin_acc);
3) The highest impact sustained by the player in the game as measured by the rotational acceleration (Max_Rot_acc);
4) The highest impact sustained by the player in the game as measured by a combined score (HITsp) of the location of impact, linear and rotational acceleration (Max_HITsp);
5) The sum of all impacts sustained by the player in the game as measured by linear acceleration sustained by the head (Cum_Lin_acc);
6) The sum of all impacts sustained by the player in the game as measured by the rotational acceleration (Cum_Rot_acc); and
7) The sum of all impacts sustained by the player in the game as measured by a combined score (HITsp) of the location of impact, linear and rotational acceleration (Cum_HITsp).

The analysis was performed with three levels of stringency, namely with all genes regardless of their expression levels included at first (No cut-off), with only those genes which had measurable expression in at least 50% of the samples (Expr in 0.5 samples) and lastly with only those genes which had expression in at least 80% of the samples (Expr in 0.8 samples). The following table shows the number of genes with a |slope|>0.1 and a p-value<0.1 for each category and for each biofluid sequenced. Here, expressed is defined as having at least 10 read counts of the mature microRNA.

Results:
Tables 2, 4, 6, 7, 9, 10, 12, 14, 16, 18, 20, 22, 24, and 26-31 list the significant microRNA markers from linear expression with just year 1 samples, and Tables 3, 5, 8, 11, 13, 15, 17, 19, 21, 23, and 25 list the significant microRNA markers from linear expression with the combination of year 1 and year 2 samples, which may be used to determine the extent of a subject's head impact injury. The analysis was performed with two levels of stringency: (1) only those genes which had measurable expression in at least 50% of the samples (Expr in 0.5 samples) and (2) only those genes which had expression in at least 80% of the samples (Expr in 0.8 samples). Genes with a |slope|>0.1 and a p-value<0.05 were considered significant. Tables 2-13 list the significant markers in plasma samples from analysis with just year 1 samples and the combination of year 1 and year 2 samples. Tables 14-25 list the significant markers in urine samples just year 1 samples and the combination of year 1 and year 2 samples. Tables 26-31 list the significant markers in saliva samples with just year 1 samples. The absolute value of the linear regression data for a specific microRNA marker indicates the level of responsiveness of the specific microRNA marker's expression to the an impact data.

2. Differential Expression Analysis of microRNA Expression in Blood and Saliva Samples Methods:

Two differential expression (DE) analyses were performed. For the first, the data set was divided by biofluid (plasma and urine only) into various categories based on a single measurement: number of hits sustained on the previous day or the highest impact sustained on the previous day (HITsp). For this analysis, Max_HITsp refers to samples from players who sustain a hit greater than or equal to 85 the previous day; Min_HITsp refers to samples form players who sustain a hit less than or equal to 30 the previous day; High_freq_hits refers to samples players who were hit greater than or equal to 60 times the previous day; Low_freq_hits refers to samples from players who were hit less than or equal to 15 times the previous day; Baseline refers to samples acquired from players before the season began; and Concussion refer to samples from players with a diagnosed concussion.

The categories for the DE (case v. control) analysis conducted are listed below.

Concussion vs. Baseline
Concussion vs. High_freq_hits
Concussion vs. Low_freq_hits
Concussion vs. Max_hitsp
Concussion vs. Min_hitsp
High_freq_hits vs. Low_freq_hits
High_freq_hits vs. Baseline
Low_freq_hits vs. Baseline
Max_hitsp vs. Min_hitsp
Max_hitsp vs. Baseline
Min_hitsp vs. Baseline For the second DE analysis, the data was separated by weighting each impact sustained the previous day by the linear and rotational acceleration for each impact. We have used the method of Rowson et. al ("Brain Injury Prediction: Assessing the Combined Probability of Concussion Using Linear and Rotational Head Acceleration." *Ann of Biomed. Engg* 2013) to determine risk of exposure associated with each impact. Briefly, each impact sustained by the player is given a probability score that informs the risk of exposure to potentially injurious impacts. These probabilities are summed up for the previous day hit data to get a cumulative risk score. The players are then categorized as 0 (least risk: baseline samples), 1 (risk between 0-0.1), 2 (0.1-0.5) and 3 (0.5 and above). Differential expression analysis was then conducted for the following category comparisons: 3 vs. 0, 3 vs. 1, 3 vs. 2, 2 vs. 0, 2 vs. 1, and 1 vs. 0.

The above analysis therefore takes into account the number of impacts sustained by the player the previous day along with their corresponding impact information (linear and rotational acceleration associated with each hit).

Results:

Tables 32-41 list the differentially expressed microRNA markers based on the above comparisons and depict the direction of change in the expression of these markers in the pairwise comparisons. Positive values indicate increased expression while negative values indicate decreased expression. Table 32 lists markers that are differentially expressed in plasma based on known diagnosis of concussion. Table 34 and 35 list markers that are differentially expressed in plasma when considering the frequency of head impact or when considering the level of head impact. Tables 38 and 39 list markers that are differentially expressed in plasma when considering the subjects' probability score for the risk of concussion or exposure to potentially injurious head impact. Table 33 lists markers that are differentially expressed in urine based on known diagnosis of concussion. Tables 36 and 37 list markers that are differentially expressed in urine when considering the frequency of head impact or when considering the level of head impact. Tables 40 and 41 list markers that are differentially expressed in urine when considering the subjects' probability score for the risk of concussion or exposure to potentially injurious head impact.

3. Random Forest Classification

Methods:

The genes significantly differentially expressed at an absolute log 2FC>1 and p-value<0.05 were used for Random Forest classification. Random Forest classifier is an ensemble type classifier that builds many weak classifiers and averages the results from them to give a robust class prediction (L. Breiman. "Random forests." *Machine Learning*, 45(1): 5-32, 2001). Recursive feature elimination based on the variable importance was used to remove genes that were not critical to the classification. The full set of differentially expressed genes was used in the first iteration and in subsequent iterations 20% of the genes with the lowest importance were removed and the classification was performed. The data was split into 80% training and 20% test sets and the results for the test set were averaged for 100 random splits (to give training and test data sets). The results for accuracy, sensitivity and specificity are presented here along with the null accuracy. The null accuracy is the accuracy if no classification was performed and every sample was labeled with the class label of the most abundant class.

Results

Tables 42-65 list of miRNAs that are most useful in the classification analysis for the following comparisons:

High_freq_hits and Low_freq_hits (Tables 42 and 54);
High_freq_hits and Baseline (Tables 43 and 55);
Low_freq_hits and Baseline (Tables 44 and 56);
Max_hitsp and Min_hitsp (Tables 45 and 57);
Max_hitsp and Baseline (Tables 46 and 58);
Min_hitsp and Baseline (Tables 47 and 59);
Samples from subjects with mild exposure to potentially injurious head impact (probability score of 0-0.1, Class 1) and samples from subjects with least exposure to potentially injurious head impact (probability score of 0, Class 0) (Tables 48 and 60);
Samples from subjects with moderate exposure potentially injurious head impact (probability score of 0.1-0.5, Class 2) and samples from Class 0 subjects (Tables 49 and 61);

Samples from Class 2 subjects and samples from Class 1 subjects (Tables 50 and 62);

Samples from subjects with high exposure potentially injurious head impact (probability score of >0.5, Class 3) and samples from Class 0 subjects (Tables 51 and 63);

Samples from Class 3 subjects and samples from Class 1 subjects (Tables 52 and 64); and Samples from Class 3 subjects and samples from Class 2 subjects (Tables 53 and 65).

Tables 42-53 lists significant markers from plasma samples while Tables 54-65 lists significant markers from urine samples. The list of microRNA markers from the more stringent differential expression analysis along with direction in the change in expression of the markers are presented in Tables 35, 37, 39, and 41.

The results for accuracy, sensitivity and specificity are presented here along with the null accuracy (Table 66 for plasma samples and Table 67 for urine samples). The null accuracy is the accuracy if no classification was performed and every sample was labeled with the class label of the most abundant class. As seen in Table 66, results for the classification of the comparisons among Classes 1-3 are the most informative when compared to the comparisons of High_freq_hits and Low_freq_hits, High_freq_hits and Baseline, Low_freq_hits and Baseline, Max_hitsp and Min_hitsp, Max_hitsp and Baseline, and Min_hitsp and Baseline. The samples labeled Class 3, 2, 1, and 0 take into account the number of hits, the linear, and rotational acceleration as opposed to the categories of High_freq_hits, Low_freq_hits, Max_hitsp, and Min_hitsp, which take into account only one hit parameter.

TABLE 1

| MicroRNA | Sample sources |
|---|---|
| hsa-let-7a-3p | plasma, urine |
| hsa-let-7a-5p | urine, saliva |
| hsa-let-7b-3p | urine |
| hsa-let-7b-5p | urine |
| hsa-let-7c-3p | urine |
| hsa-let-7c-5p | plasma, urine, saliva |
| hsa-let-7d-3p | plasma |
| hsa-let-7d-5p | urine |
| hsa-let-7e-3p | plasma |
| hsa-let-7e-5p | urine |
| hsa-let-7f-1-3p | plasma |
| hsa-let-7f-5p | urine, saliva |
| hsa-let-7g-3p | plasma |
| hsa-let-7g-5p | urine |
| hsa-let-7i-3p | plasma |
| hsa-let-7i-5p | plasma |
| hsa-miR-1-3p | plasma |
| hsa-miR-100-5p | plasma, urine |
| hsa-miR-101-3p | plasma |
| hsa-miR-101-5p | plasma |
| hsa-miR-106a-3p | plasma |
| hsa-miR-106a-5p | plasma, urine |
| hsa-miR-106b-3p | plasma, urine, saliva |
| hsa-miR-106b-5p | plasma, urine |
| hsa-miR-107 | plasma, urine |
| hsa-miR-10a-5p | plasma |
| hsa-miR-10b-3p | urine |
| hsa-miR-10b-5p | plasma |
| hsa-miR-1180-3p | plasma, urine |
| hsa-miR-1185-1-3p | plasma |
| hsa-miR-1185-2-3p | plasma |
| hsa-miR-1197 | plasma |
| hsa-miR-122-5p | plasma, urine, saliva |
| hsa-miR-1224-5p | plasma |
| hsa-miR-1226-3p | urine |
| hsa-miR-1226-5p | plasma, urine |
| hsa-miR-1228-3p | plasma |

TABLE 1-continued

| MicroRNA | Sample sources |
|---|---|
| hsa-miR-1228-5p | plasma |
| hsa-miR-1229-3p | plasma |
| hsa-miR-1233-3p | plasma |
| hsa-miR-1234-3p | plasma |
| hsa-miR-1238-3p | plasma |
| hsa-miR-124-3p | plasma |
| hsa-miR-1246 | plasma, urine |
| hsa-miR-1247-3p | urine |
| hsa-miR-1247-5p | plasma |
| hsa-miR-1255b-5p | plasma |
| hsa-miR-125a-3p | urine |
| hsa-miR-125a-5p | plasma, urine, saliva |
| hsa-miR-125b-1-3p | plasma, urine |
| hsa-miR-125b-2-3p | plasma |
| hsa-miR-125b-5p | plasma, urine, saliva |
| hsa-miR-126-3p | urine |
| hsa-miR-126-5p | urine |
| hsa-miR-1260a | plasma, urine, saliva |
| hsa-miR-1260b | plasma, urine |
| hsa-miR-1264 | plasma |
| hsa-miR-1269a | urine |
| hsa-miR-1269b | urine |
| hsa-miR-127-3p | plasma, urine |
| hsa-miR-127-5p | plasma |
| hsa-miR-1270 | plasma |
| hsa-miR-1273g-3p | urine |
| hsa-miR-1275 | plasma, urine |
| hsa-miR-1283 | plasma |
| hsa-miR-1287-5p | plasma, urine |
| hsa-miR-1288-3p | plasma |
| hsa-miR-129-2-3p | plasma |
| hsa-miR-129-5p | plasma, urine |
| hsa-miR-1291 | plasma |
| hsa-miR-1292-5p | plasma |
| hsa-miR-1294 | plasma |
| hsa-miR-1296-5p | plasma |
| hsa-miR-1298-3p | plasma |
| hsa-miR-1298-5p | plasma, urine |
| hsa-miR-1299 | plasma, urine |
| hsa-miR-1301-3p | urine |
| hsa-miR-1304-3p | urine |
| hsa-miR-1307-3p | urine, saliva |
| hsa-miR-1307-5p | urine |
| hsa-miR-130a-3p | plasma, urine, saliva |
| hsa-miR-130b-3p | plasma, urine |
| hsa-miR-130b-5p | urine |
| hsa-miR-132-3p | urine, saliva |
| hsa-miR-1323 | plasma |
| hsa-miR-133a-3p | plasma, saliva |
| hsa-miR-133a-5p | plasma |
| hsa-miR-134-5p | plasma |
| hsa-miR-1343-3p | plasma |
| hsa-miR-135a-5p | plasma, urine |
| hsa-miR-136-3p | plasma, urine |
| hsa-miR-136-5p | plasma, urine |
| hsa-miR-138-1-3p | plasma |
| hsa-miR-138-5p | plasma, urine |
| hsa-miR-139-3p | plasma |
| hsa-miR-139-5p | plasma |
| hsa-miR-140-3p | saliva |
| hsa-miR-140-5p | saliva |
| hsa-miR-141-3p | plasma, urine |
| hsa-miR-142-3p | urine |
| hsa-miR-143-3p | plasma, urine |
| hsa-miR-143-5p | plasma |
| hsa-miR-144-3p | plasma, urine |
| hsa-miR-144-5p | plasma |
| hsa-miR-145-3p | plasma |
| hsa-miR-145-5p | plasma |
| hsa-miR-1468-5p | plasma |
| hsa-miR-146a-3p | plasma |
| hsa-miR-146a-5p | urine |
| hsa-miR-146b-3p | urine |
| hsa-miR-146b-5p | plasma, urine |
| hsa-miR-147b | plasma |
| hsa-miR-148a-5p | urine |
| hsa-miR-148b-5p | urine |
| hsa-miR-149-3p | urine |

TABLE 1-continued

| MicroRNA | Sample sources |
|---|---|
| hsa-miR-149-5p | plasma, urine |
| hsa-miR-150-3p | plasma |
| hsa-miR-150-5p | plasma, urine |
| hsa-miR-151a-3p | plasma, urine, saliva |
| hsa-miR-151a-5p | saliva |
| hsa-miR-151b | saliva |
| hsa-miR-152-3p | plasma |
| hsa-miR-153-3p | plasma |
| hsa-miR-154-5p | plasma |
| hsa-miR-155-5p | urine |
| hsa-miR-15a-5p | plasma |
| hsa-miR-15b-3p | plasma |
| hsa-miR-15b-5p | urine, saliva |
| hsa-miR-16-2-3p | plasma |
| hsa-miR-16-5p | plasma |
| hsa-miR-181a-2-3p | plasma, urine |
| hsa-miR-181a-3p | urine |
| hsa-miR-181a-5p | urine |
| hsa-miR-181b-5p | plasma, urine, saliva |
| hsa-miR-181c-3p | plasma, saliva |
| hsa-miR-181c-5p | plasma, urine, saliva |
| hsa-miR-181d-3p | plasma |
| hsa-miR-181d-5p | saliva |
| hsa-miR-182-5p | plasma, urine |
| hsa-miR-183-3p | plasma |
| hsa-miR-183-5p | plasma |
| hsa-miR-184 | plasma, urine |
| hsa-miR-185-3p | plasma, urine |
| hsa-miR-185-5p | plasma, saliva |
| hsa-miR-186-5p | saliva |
| hsa-miR-187-3p | plasma, urine |
| hsa-miR-188-5p | plasma, urine |
| hsa-miR-18a-3p | plasma |
| hsa-miR-18a-5p | plasma |
| hsa-miR-18b-3p | plasma |
| hsa-miR-1908-3p | urine |
| hsa-miR-1908-5p | plasma |
| hsa-miR-190a-3p | plasma, urine |
| hsa-miR-190a-5p | urine |
| hsa-miR-191-3p | plasma |
| hsa-miR-191-5p | plasma, saliva |
| hsa-miR-1910-5p | urine |
| hsa-miR-1911-3p | plasma |
| hsa-miR-1911-5p | plasma, urine |
| hsa-miR-1912 | plasma |
| hsa-miR-192-3p | saliva |
| hsa-miR-192-5p | plasma, urine |
| hsa-miR-193a-3p | urine |
| hsa-miR-193a-5p | plasma, urine |
| hsa-miR-193b-3p | plasma, urine, saliva |
| hsa-miR-193b-5p | plasma |
| hsa-miR-194-5p | urine |
| hsa-miR-195-3p | plasma |
| hsa-miR-195-5p | plasma, saliva |
| hsa-miR-196b-5p | urine |
| hsa-miR-197-3p | plasma, urine |
| hsa-miR-197-5p | plasma, urine |
| hsa-miR-1976 | plasma |
| hsa-miR-199a-3p | urine |
| hsa-miR-199a-5p | plasma, urine |
| hsa-miR-199b-5p | plasma, urine |
| hsa-miR-19a-3p | plasma, urine |
| hsa-miR-19a-5p | plasma |
| hsa-miR-19b-3p | urine |
| hsa-miR-200a-3p | urine |
| hsa-miR-200a-5p | urine |
| hsa-miR-200b-3p | urine, saliva |
| hsa-miR-200c-3p | urine |
| hsa-miR-203a-3p | plasma, urine, saliva |
| hsa-miR-203b-5p | urine |
| hsa-miR-204-3p | plasma, urine |
| hsa-miR-204-5p | plasma, saliva |
| hsa-miR-205-5p | plasma, urine |
| hsa-miR-208b-3p | plasma |
| hsa-miR-20a-3p | plasma |
| hsa-miR-20a-5p | urine |
| hsa-miR-20b-3p | plasma |
| hsa-miR-20b-5p | urine |
| hsa-miR-21-3p | urine |
| hsa-miR-21-5p | urine |
| hsa-miR-210-3p | plasma, urine |
| hsa-miR-210-5p | plasma, urine |
| hsa-miR-211-5p | plasma, urine |
| hsa-miR-2110 | plasma, urine |
| hsa-miR-2115-3p | plasma, saliva |
| hsa-miR-212-3p | urine |
| hsa-miR-212-5p | plasma |
| hsa-miR-214-3p | plasma |
| hsa-miR-214-5p | plasma |
| hsa-miR-215-5p | plasma, urine |
| hsa-miR-218-5p | plasma |
| hsa-miR-219a-2-3p | plasma, urine |
| hsa-miR-219b-5p | plasma |
| hsa-miR-22-3p | plasma, urine |
| hsa-miR-22-5p | plasma, urine |
| hsa-miR-221-3p | plasma, urine |
| hsa-miR-223-3p | urine |
| hsa-miR-223-5p | plasma |
| hsa-miR-224-3p | plasma |
| hsa-miR-224-5p | plasma, urine, saliva |
| hsa-miR-2276-3p | plasma |
| hsa-miR-2277-5p | urine |
| hsa-miR-2392 | plasma |
| hsa-miR-23a-3p | plasma, urine |
| hsa-miR-23a-5p | plasma |
| hsa-miR-23b-3p | plasma, urine, saliva |
| hsa-miR-23b-5p | plasma |
| hsa-miR-23c | plasma |
| hsa-miR-24-3p | plasma, saliva |
| hsa-miR-25-3p | plasma, urine |
| hsa-miR-25-5p | plasma, urine |
| hsa-miR-26a-2-3p | plasma |
| hsa-miR-26a-5p | saliva |
| hsa-miR-26b-3p | urine |
| hsa-miR-26b-5p | urine |
| hsa-miR-27a-3p | urine |
| hsa-miR-27a-5p | plasma, saliva |
| hsa-miR-27b-3p | urine |
| hsa-miR-27b-5p | plasma |
| hsa-miR-28-3p | plasma, urine |
| hsa-miR-296-3p | plasma, urine |
| hsa-miR-296-5p | plasma |
| hsa-miR-29a-3p | urine |
| hsa-miR-29b-1-5p | plasma |
| hsa-miR-29b-2-5p | plasma |
| hsa-miR-29b-3p | urine |
| hsa-miR-29c-3p | plasma, urine |
| hsa-miR-301a-3p | plasma |
| hsa-miR-301b-3p | plasma |
| hsa-miR-3064-5p | plasma |
| hsa-miR-3065-5p | urine |
| hsa-miR-3074-5p | plasma |
| hsa-miR-30a-3p | plasma |
| hsa-miR-30a-5p | plasma |
| hsa-miR-30b-5p | plasma, urine |
| hsa-miR-30c-1-3p | urine |
| hsa-miR-30c-2-3p | plasma, urine |
| hsa-miR-30d-3p | plasma, urine |
| hsa-miR-30d-5p | plasma |
| hsa-miR-30e-3p | plasma, urine |
| hsa-miR-30e-5p | saliva |
| hsa-miR-31-5p | plasma, urine |
| hsa-miR-3115 | plasma |
| hsa-miR-3121-3p | plasma |
| hsa-miR-3122 | plasma |
| hsa-miR-3127-5p | plasma, urine |
| hsa-miR-3130-3p | plasma |
| hsa-miR-3136-5p | plasma |
| hsa-miR-3138 | plasma |
| hsa-miR-3140-3p | plasma |
| hsa-miR-3150a-5p | plasma |
| hsa-miR-3150b-3p | plasma |
| hsa-miR-3154 | plasma |
| hsa-miR-3155a | plasma |
| hsa-miR-3155b | plasma |
| hsa-miR-3157-3p | plasma |

TABLE 1-continued

| MicroRNA | Sample sources |
|---|---|
| hsa-miR-3158-3p | plasma, urine |
| hsa-miR-3158-5p | plasma |
| hsa-miR-3159 | plasma |
| hsa-miR-3160-3p | plasma |
| hsa-miR-3160-5p | plasma |
| hsa-miR-3163 | plasma |
| hsa-miR-3168 | plasma, urine |
| hsa-miR-3173-3p | plasma |
| hsa-miR-3173-5p | plasma |
| hsa-miR-3175 | plasma |
| hsa-miR-3176 | plasma |
| hsa-miR-3177-3p | urine |
| hsa-miR-3177-5p | plasma |
| hsa-miR-3182 | plasma, urine |
| hsa-miR-3184-3p | urine |
| hsa-miR-3184-5p | plasma |
| hsa-miR-3187-5p | plasma |
| hsa-miR-3194-3p | plasma |
| hsa-miR-3194-5p | plasma |
| hsa-miR-3199 | plasma |
| hsa-miR-32-3p | plasma |
| hsa-miR-32-5p | plasma, urine, saliva |
| hsa-miR-3200-5p | plasma |
| hsa-miR-320a | plasma, urine |
| hsa-miR-320b | plasma, urine |
| hsa-miR-320c | plasma, urine |
| hsa-miR-320d | plasma, urine |
| hsa-miR-320e | plasma, urine |
| hsa-miR-323a-3p | plasma |
| hsa-miR-323b-3p | plasma, urine |
| hsa-miR-324-3p | plasma, urine |
| hsa-miR-324-5p | plasma, urine, saliva |
| hsa-miR-326 | plasma, urine |
| hsa-miR-328-3p | plasma, urine |
| hsa-miR-328-5p | plasma |
| hsa-miR-330-5p | plasma |
| hsa-miR-331-3p | plasma, urine |
| hsa-miR-331-5p | urine |
| hsa-miR-335-3p | urine, saliva |
| hsa-miR-337-5p | plasma |
| hsa-miR-338-3p | plasma, urine |
| hsa-miR-338-5p | plasma, urine |
| hsa-miR-339-3p | plasma, urine |
| hsa-miR-339-5p | urine |
| hsa-miR-33a-5p | plasma |
| hsa-miR-33b-5p | plasma, urine |
| hsa-miR-340-3p | urine, saliva |
| hsa-miR-342-3p | plasma, urine |
| hsa-miR-342-5p | plasma, urine, saliva |
| hsa-miR-345-5p | plasma, urine, saliva |
| hsa-miR-34a-5p | urine, saliva |
| hsa-miR-34b-3p | plasma, saliva |
| hsa-miR-34b-5p | plasma |
| hsa-miR-34c-3p | plasma, saliva |
| hsa-miR-34c-5p | plasma, saliva |
| hsa-miR-3529-3p | plasma |
| hsa-miR-3591-3p | plasma |
| hsa-miR-3605-3p | plasma |
| hsa-miR-3605-5p | plasma, urine |
| hsa-miR-361-3p | plasma, urine, saliva |
| hsa-miR-361-5p | urine, saliva |
| hsa-miR-3610 | urine |
| hsa-miR-3611 | plasma |
| hsa-miR-3614-5p | plasma |
| hsa-miR-3615 | urine, saliva |
| hsa-miR-362-3p | plasma |
| hsa-miR-362-5p | plasma, urine |
| hsa-miR-3620-3p | plasma |
| hsa-miR-363-3p | plasma |
| hsa-miR-363-5p | urine |
| hsa-miR-3656 | plasma |
| hsa-miR-365a-3p | plasma, saliva |
| hsa-miR-365b-3p | saliva |
| hsa-miR-365b-5p | plasma |
| hsa-miR-3677-3p | plasma |
| hsa-miR-3682-3p | plasma |
| hsa-miR-3688-3p | plasma |
| hsa-miR-3688-5p | plasma |
| hsa-miR-3691-5p | plasma |
| hsa-miR-370-3p | plasma |
| hsa-miR-371a-3p | plasma |
| hsa-miR-371a-5p | plasma |
| hsa-miR-371b-3p | plasma |
| hsa-miR-371b-5p | plasma |
| hsa-miR-373-3p | plasma |
| hsa-miR-374a-3p | urine |
| hsa-miR-374b-5p | urine, saliva |
| hsa-miR-374c-3p | urine |
| hsa-miR-374c-5p | plasma |
| hsa-miR-375 | plasma, urine |
| hsa-miR-377-3p | plasma |
| hsa-miR-377-5p | plasma |
| hsa-miR-378a-3p | plasma, urine |
| hsa-miR-378a-5p | plasma, urine |
| hsa-miR-378b | plasma |
| hsa-miR-378c | plasma, urine |
| hsa-miR-378d | plasma, urine |
| hsa-miR-378e | plasma, urine |
| hsa-miR-378f | plasma, urine |
| hsa-miR-378g | plasma |
| hsa-miR-378i | plasma, urine, saliva |
| hsa-miR-379-3p | plasma |
| hsa-miR-380-3p | plasma |
| hsa-miR-381-3p | urine |
| hsa-miR-382-5p | plasma |
| hsa-miR-383-5p | plasma |
| hsa-miR-3909 | plasma, saliva |
| hsa-miR-3913-5p | plasma, urine |
| hsa-miR-3918 | plasma |
| hsa-miR-3928-3p | urine |
| hsa-miR-3934-5p | plasma |
| hsa-miR-3940-3p | plasma |
| hsa-miR-3960 | plasma |
| hsa-miR-409-3p | urine |
| hsa-miR-410-3p | plasma, urine |
| hsa-miR-421 | plasma |
| hsa-miR-423-3p | urine, saliva |
| hsa-miR-423-5p | plasma, urine |
| hsa-miR-424-3p | plasma, urine |
| hsa-miR-424-5p | plasma, urine |
| hsa-miR-425-3p | saliva |
| hsa-miR-4284 | urine |
| hsa-miR-431-5p | plasma |
| hsa-miR-4326 | plasma |
| hsa-miR-4424 | plasma |
| hsa-miR-4433b-5p | plasma |
| hsa-miR-4436b-3p | plasma |
| hsa-miR-4440 | plasma |
| hsa-miR-4443 | plasma, urine |
| hsa-miR-4446-3p | plasma, urine |
| hsa-miR-4448 | plasma, urine |
| hsa-miR-4449 | plasma, urine |
| hsa-miR-4454 | urine |
| hsa-miR-4461 | plasma, urine |
| hsa-miR-4466 | plasma |
| hsa-miR-4467 | plasma |
| hsa-miR-4474-3p | plasma |
| hsa-miR-4479 | plasma |
| hsa-miR-448 | plasma |
| hsa-miR-4482-3p | plasma |
| hsa-miR-4488 | urine |
| hsa-miR-4489 | plasma |
| hsa-miR-4492 | plasma, urine |
| hsa-miR-449a | plasma, urine |
| hsa-miR-449b-5p | plasma, saliva |
| hsa-miR-449c-5p | plasma, urine, saliva |
| hsa-miR-4504 | plasma |
| hsa-miR-4507 | urine |
| hsa-miR-4508 | plasma |
| hsa-miR-450a-5p | urine |
| hsa-miR-450b-5p | urine |
| hsa-miR-4510 | plasma, urine |
| hsa-miR-4511 | plasma |
| hsa-miR-451a | plasma, urine |
| hsa-miR-451b | plasma |
| hsa-miR-452-5p | urine |

TABLE 1-continued

| MicroRNA | Sample sources |
|---|---|
| hsa-miR-4523 | plasma |
| hsa-miR-4532 | urine |
| hsa-miR-454-3p | urine |
| hsa-miR-455-3p | plasma, urine |
| hsa-miR-455-5p | plasma, urine |
| hsa-miR-4638-5p | plasma |
| hsa-miR-4646-5p | plasma |
| hsa-miR-4647 | plasma |
| hsa-miR-4654 | plasma |
| hsa-miR-4657 | plasma |
| hsa-miR-4667-5p | plasma |
| hsa-miR-4668-5p | plasma |
| hsa-miR-4669 | plasma |
| hsa-miR-4673 | plasma |
| hsa-miR-4677-3p | urine |
| hsa-miR-4682 | plasma |
| hsa-miR-4685-3p | plasma |
| hsa-miR-4687-5p | plasma |
| hsa-miR-4701-5p | plasma |
| hsa-miR-4707-3p | plasma |
| hsa-miR-4709-5p | plasma |
| hsa-miR-4726-5p | plasma |
| hsa-miR-4727-3p | plasma |
| hsa-miR-4728-3p | urine |
| hsa-miR-4732-3p | plasma, urine, saliva |
| hsa-miR-4732-5p | plasma |
| hsa-miR-4738-3p | plasma |
| hsa-miR-4742-3p | plasma |
| hsa-miR-4743-5p | plasma |
| hsa-miR-4745-3p | plasma |
| hsa-miR-4745-5p | plasma, urine |
| hsa-miR-4746-5p | plasma, urine |
| hsa-miR-4747-5p | plasma |
| hsa-miR-4748 | plasma |
| hsa-miR-4753-5p | plasma |
| hsa-miR-4754 | plasma |
| hsa-miR-4755-3p | plasma |
| hsa-miR-4755-5p | plasma |
| hsa-miR-4762-5p | plasma |
| hsa-miR-4766-3p | plasma |
| hsa-miR-4767 | plasma |
| hsa-miR-4772-3p | plasma |
| hsa-miR-4772-5p | plasma |
| hsa-miR-4775 | urine |
| hsa-miR-4783-3p | plasma |
| hsa-miR-4785 | plasma |
| hsa-miR-4792 | plasma, urine |
| hsa-miR-4797-3p | plasma |
| hsa-miR-483-3p | plasma |
| hsa-miR-483-5p | plasma |
| hsa-miR-484 | plasma, urine, saliva |
| hsa-miR-485-3p | plasma, saliva |
| hsa-miR-485-5p | plasma, urine |
| hsa-miR-486-3p | plasma, urine |
| hsa-miR-486-5p | plasma, urine |
| hsa-miR-489-3p | urine |
| hsa-miR-490-3p | plasma |
| hsa-miR-490-5p | plasma |
| hsa-miR-493-3p | plasma |
| hsa-miR-494-5p | plasma |
| hsa-miR-497-5p | plasma, urine |
| hsa-miR-499a-5p | plasma |
| hsa-miR-5001-3p | plasma |
| hsa-miR-5006-5p | plasma |
| hsa-miR-5009-5p | plasma |
| hsa-miR-500a-3p | urine |
| hsa-miR-500a-5p | urine |
| hsa-miR-500b-3p | plasma |
| hsa-miR-501-3p | plasma, urine |
| hsa-miR-501-5p | plasma, urine |
| hsa-miR-5010-5p | plasma, urine, saliva |
| hsa-miR-502-3p | plasma, urine |
| hsa-miR-503-3p | plasma |
| hsa-miR-505-3p | urine |
| hsa-miR-508-3p | urine |
| hsa-miR-509-3p | plasma, urine |
| hsa-miR-5096 | plasma |
| hsa-miR-5100 | plasma, urine |
| hsa-miR-511-5p | plasma |
| hsa-miR-512-3p | plasma |
| hsa-miR-515-3p | plasma |
| hsa-miR-515-5p | plasma |
| hsa-miR-516a-5p | plasma |
| hsa-miR-516b-5p | plasma |
| hsa-miR-517a-3p = hsa-miR-517b-3p | plasma |
| hsa-miR-517c-3p | plasma |
| hsa-miR-5187-5p | plasma |
| hsa-miR-5189-3p | plasma |
| hsa-miR-5189-5p | plasma |
| hsa-miR-518b | plasma |
| hsa-miR-518c-3p | plasma |
| hsa-miR-518e-5p = hsa-miR-519a-5p = hsa-miR-519b-5p = hsa-miR-519c-5p = hsa-miR-522-5p = hsa-miR-523-5p | plasma |
| hsa-miR-519c-3p | plasma |
| hsa-miR-519d-3p | plasma |
| hsa-miR-520d-5p | plasma |
| hsa-miR-526b-5p | plasma |
| hsa-miR-532-3p | plasma, urine |
| hsa-miR-532-5p | plasma |
| hsa-miR-539-3p | plasma |
| hsa-miR-541-3p | plasma |
| hsa-miR-542-3p | plasma |
| hsa-miR-542-5p | plasma, urine, saliva |
| hsa-miR-543 | plasma |
| hsa-miR-548ac | plasma |
| hsa-miR-548am-5p | plasma |
| hsa-miR-548as-3p | plasma |
| hsa-miR-548at-5p | plasma |
| hsa-miR-548au-5p | plasma |
| hsa-miR-548ax | plasma |
| hsa-miR-548ba | plasma |
| hsa-miR-548c-5p | plasma |
| hsa-miR-548e-3p | plasma |
| hsa-miR-548e-5p | saliva |
| hsa-miR-548f-5p | plasma |
| hsa-miR-548o-5p | plasma |
| hsa-miR-550a-3-5p | plasma |
| hsa-miR-550a-3p | plasma |
| hsa-miR-550a-5p | plasma |
| hsa-miR-550b-2-5p | plasma |
| hsa-miR-551a | plasma |
| hsa-miR-5583-3p | plasma |
| hsa-miR-5586-3p | plasma |
| hsa-miR-5586-5p | plasma |
| hsa-miR-5587-3p | plasma |
| hsa-miR-561-5p | urine |
| hsa-miR-5689 | plasma |
| hsa-miR-5695 | plasma |
| hsa-miR-5696 | plasma |
| hsa-miR-570-3p | plasma |
| hsa-miR-574-3p | plasma, urine |
| hsa-miR-574-5p | plasma |
| hsa-miR-576-3p | plasma |
| hsa-miR-576-5p | saliva |
| hsa-miR-577 | plasma, urine |
| hsa-miR-579-5p | plasma |
| hsa-miR-582-3p | plasma, urine |
| hsa-miR-582-5p | plasma, saliva |
| hsa-miR-589-3p | plasma, urine |
| hsa-miR-590-3p | urine, saliva |
| hsa-miR-590-5p | plasma |
| hsa-miR-592 | plasma |
| hsa-miR-6070 | plasma |
| hsa-miR-6087 | plasma |
| hsa-miR-6130 | plasma |
| hsa-miR-6131 | plasma |
| hsa-miR-615-3p | plasma, urine |
| hsa-miR-615-5p | plasma, urine |
| hsa-miR-616-3p | plasma |
| hsa-miR-616-5p | plasma |
| hsa-miR-624-5p | plasma |

TABLE 1-continued

| MicroRNA | Sample sources |
|---|---|
| hsa-miR-625-3p | plasma |
| hsa-miR-625-5p | plasma |
| hsa-miR-627-5p | plasma |
| hsa-miR-628-3p | urine |
| hsa-miR-628-5p | urine |
| hsa-miR-629-5p | plasma, urine, saliva |
| hsa-miR-636 | plasma |
| hsa-miR-642a-3p | plasma |
| hsa-miR-642b-5p | plasma |
| hsa-miR-6501-5p | plasma |
| hsa-miR-6503-3p | plasma |
| hsa-miR-6505-3p | plasma |
| hsa-miR-6509-3p | plasma |
| hsa-miR-6509-5p | plasma |
| hsa-miR-651-5p | urine |
| hsa-miR-6511a-5p | plasma |
| hsa-miR-6511b-3p | plasma |
| hsa-miR-6511b-5p | plasma |
| hsa-miR-652-3p | plasma |
| hsa-miR-653-5p | urine |
| hsa-miR-659-5p | plasma |
| hsa-miR-660-3p | plasma |
| hsa-miR-660-5p | plasma |
| hsa-miR-664a-3p | plasma, saliva |
| hsa-miR-664a-5p | plasma, urine |
| hsa-miR-664b-5p | plasma |
| hsa-miR-671-5p | plasma, urine |
| hsa-miR-6723-5p | urine |
| hsa-miR-6726-3p | plasma |
| hsa-miR-6730-5p | plasma |
| hsa-miR-6734-5p | plasma |
| hsa-miR-6735-3p | plasma |
| hsa-miR-6735-5p | plasma |
| hsa-miR-6737-3p | plasma |
| hsa-miR-6738-5p | plasma |
| hsa-miR-6739-3p | plasma |
| hsa-miR-6740-5p | plasma |
| hsa-miR-6741-3p | plasma |
| hsa-miR-6749-3p | plasma |
| hsa-miR-675-5p | plasma |
| hsa-miR-6751-3p | plasma |
| hsa-miR-6754-3p | plasma |
| hsa-miR-6764-3p | plasma |
| hsa-miR-6767-5p | plasma |
| hsa-miR-6770-3p | plasma |
| hsa-miR-6770-5p | plasma |
| hsa-miR-6777-3p | plasma |
| hsa-miR-6780a-5p | plasma |
| hsa-miR-6781-5p | plasma |
| hsa-miR-6782-3p | plasma |
| hsa-miR-6787-5p | plasma |
| hsa-miR-6791-3p | plasma |
| hsa-miR-6791-5p | plasma |
| hsa-miR-6793-3p | plasma, urine |
| hsa-miR-6802-5p | plasma |
| hsa-miR-6805-5p | plasma |
| hsa-miR-6809-3p | plasma |
| hsa-miR-6810-3p | plasma |
| hsa-miR-6817-3p | plasma |
| hsa-miR-6820-3p | plasma |
| hsa-miR-6820-5p | plasma |
| hsa-miR-6824-3p | plasma |
| hsa-miR-6829-5p | plasma |
| hsa-miR-6832-5p | plasma |
| hsa-miR-6836-3p | plasma |
| hsa-miR-6840-3p | plasma |
| hsa-miR-6850-5p | plasma |
| hsa-miR-6851-5p | plasma |
| hsa-miR-6852-5p | urine |
| hsa-miR-6853-3p | plasma |
| hsa-miR-6858-5p | plasma, urine |
| hsa-miR-6859-3p | plasma |
| hsa-miR-6868-3p | plasma |
| hsa-miR-6875-5p | plasma |
| hsa-miR-6876-5p | plasma |
| hsa-miR-6877-3p | plasma |
| hsa-miR-6878-5p | plasma |
| hsa-miR-6879-3p | plasma |
| hsa-miR-6882-5p | plasma |
| hsa-miR-6884-5p | plasma |
| hsa-miR-6885-5p | plasma |
| hsa-miR-6886-5p | plasma |
| hsa-miR-6889-3p | plasma |
| hsa-miR-6891-5p | plasma |
| hsa-miR-6892-5p | plasma |
| hsa-miR-6894-3p | plasma |
| hsa-miR-6894-5p | plasma |
| hsa-miR-7-1-3p | urine |
| hsa-miR-7-5p | plasma, saliva |
| hsa-miR-708-3p | plasma, urine |
| hsa-miR-708-5p | urine |
| hsa-miR-7106-3p | plasma |
| hsa-miR-7109-3p | plasma |
| hsa-miR-7110-3p | plasma |
| hsa-miR-7113-5p | plasma |
| hsa-miR-7151-3p | plasma |
| hsa-miR-7155-3p | plasma |
| hsa-miR-7160-5p | urine |
| hsa-miR-758-5p | plasma |
| hsa-miR-760 | urine |
| hsa-miR-7641 | plasma, urine |
| hsa-miR-766-3p | plasma, urine, saliva |
| hsa-miR-769-3p | plasma |
| hsa-miR-769-5p | plasma, urine |
| hsa-miR-7705 | plasma |
| hsa-miR-7706 | plasma, urine |
| hsa-miR-7975 | plasma, urine |
| hsa-miR-7976 | plasma |
| hsa-miR-7977 | plasma, urine |
| hsa-miR-8061 | plasma, urine |
| hsa-miR-8072 | plasma |
| hsa-miR-873-3p | plasma, urine |
| hsa-miR-873-5p | plasma, urine |
| hsa-miR-874-3p | plasma, urine |
| hsa-miR-874-5p | urine |
| hsa-miR-877-3p | plasma |
| hsa-miR-877-5p | saliva |
| hsa-miR-885-5p | plasma, saliva |
| hsa-miR-887-3p | plasma |
| hsa-miR-888-5p | urine |
| hsa-miR-891a-5p | urine |
| hsa-miR-892a | urine |
| hsa-miR-9-3p | plasma |
| hsa-miR-9-5p | plasma, urine, saliva |
| hsa-miR-92a-1-5p | plasma, urine |
| hsa-miR-92a-2-5p | urine |
| hsa-miR-92a-3p | plasma, urine |
| hsa-miR-92b-3p | plasma, saliva |
| hsa-miR-92b-5p | plasma |
| hsa-miR-93-3p | urine, saliva |
| hsa-miR-93-5p | saliva |
| hsa-miR-937-3p | plasma |
| hsa-miR-939-3p | plasma |
| hsa-miR-939-5p | plasma |
| hsa-miR-940 | plasma |
| hsa-miR-941 | urine |
| hsa-miR-942-5p | plasma |
| hsa-miR-944 | saliva |
| hsa-miR-96-5p | plasma |
| hsa-miR-98-3p | plasma, urine |
| hsa-miR-98-5p | saliva |
| hsa-miR-99a-3p | plasma |
| hsa-miR-99a-5p | plasma, urine, saliva |
| hsa-miR-99b-3p | plasma |
| hsa-miR-99b-5p | plasma, urine, saliva |

TABLE 2

| MicroRNA | No expression cut-off | Measurable expression in >50% of the samples | Measurable expression in >80% of the samples | Change in expression |
|---|---|---|---|---|
| hsa-miR-130a-3p | −0.11 | −0.11 | −0.11 | decrease |
| hsa-miR-146b-5p | −0.26 | −0.26 | −0.26 | decrease |
| hsa-miR-486-5p | 2805.07 | 2805.07 | 2805.07 | increase |

TABLE 3

| MicroRNA | No expression cut-off | Measurable expression in >50% of the samples | Measurable expression in >80% of the samples | Change in expression |
|---|---|---|---|---|
| hsa-miR-10b-5p | 3.00 | 3.00 | 3.00 | increase |
| hsa-miR-151a-3p | 3.67 | 3.67 | 3.67 | increase |
| hsa-miR-192-5p | 0.64 | 0.64 | 0.64 | increase |
| hsa-miR-24-3p | 0.28 | 0.28 | 0.28 | increase |
| hsa-miR-28-3p | 2.65 | 2.65 | 2.65 | increase |
| hsa-miR-301a-3p | −0.15 | −0.15 | −0.15 | decrease |
| hsa-miR-30a-5p | 0.36 | 0.36 | 0.36 | increase |
| hsa-miR-484 | 0.49 | 0.49 | 0.49 | increase |

TABLE 4

| MicroRNA | No expression cut-off | Measurable expression in >50% of the samples | Measurable expression in >80% of the samples | Change in expression |
|---|---|---|---|---|
| hsa-miR-146b-5p | −0.13 | −0.13 | −0.13 | decrease |
| hsa-miR-486-5p | 1393.15 | 1393.15 | 1393.15 | increase |

TABLE 5

| MicroRNA | No expression cut-off | Measurable expression in >50% of the samples | Measurable expression in >80% of the samples | Change in expression |
|---|---|---|---|---|
| hsa-miR-10b-5p | 1.47 | 1.47 | 1.47 | increase |
| hsa-miR-151a-3p | 1.95 | 1.95 | 1.95 | increase |
| hsa-miR-192-5p | 0.34 | 0.34 | 0.34 | increase |
| hsa-miR-24-3p | 0.15 | 0.15 | 0.15 | increase |
| hsa-miR-30a-5p | 0.19 | 0.19 | 0.19 | increase |
| hsa-miR-484 | 0.24 | 0.24 | 0.24 | increase |

TABLE 6

| MicroRNA | No expression cut-off | Measurable expression in >50% of the samples | Measurable expression >80% of the samples | Change in expression |
|---|---|---|---|---|
| hsa-miR-486-5p | 26.48 | 26.48 | 26.48 | increase |

TABLE 7

| MicroRNA | No expression cut-off | Measurable expression in >50% of the samples | Measurable expression in >80% of the samples | Change in expression |
|---|---|---|---|---|
| hsa-miR-106a-5p | 0.40 | 0.40 | 0.40 | increase |
| hsa-miR-106b-3p | 4.66 | 4.66 | 4.66 | increase |
| hsa-miR-124-3p | 0.13 | | | increase |

TABLE 7-continued

| MicroRNA | No expression cut-off | Measurable expression in >50% of the samples | Measurable expression in >80% of the samples | Change in expression |
|---|---|---|---|---|
| hsa-miR-1323 | 0.12 | | | increase |
| hsa-miR-136-3p | 0.40 | 0.40 | 0.40 | increase |
| hsa-miR-138-5p | 0.15 | 0.15 | | increase |
| hsa-miR-149-5p | 0.15 | | | increase |
| hsa-miR-181c-5p | 0.92 | 6.92 | 0.92 | increase |
| hsa-miR-199b-5p | 0.17 | 0.17 | 0.17 | increase |
| hsa-miR-210-3p | 6.86 | 6.86 | 6.86 | increase |
| hsa-miR-221-3p | 20.67 | 20.67 | 20.67 | increase |
| hsa-miR-23b-3p | 0.69 | 0.69 | 0.69 | increase |
| hsa-miR-30a-3p | 0.78 | 0.78 | 0.78 | increase |
| hsa-miR-30a-5p | 12.22 | 12.22 | 12.22 | increase |
| hsa-miR-30d-3p | 0.23 | 0.23 | 0.23 | increase |
| hsa-miR-421 | −0.54 | −0.54 | −0.54 | decrease |
| hsa-miR-4492 | 0.11 | | | increase |
| hsa-miR-4792 | 0.35 | 0.35 | | increase |
| hsa-miR-497-5p | 0.78 | 0.78 | 0.78 | increase |
| hsa-miR-515-5p | 0.38 | | | increase |
| hsa-miR-516a-5p | 0.43 | | | increase |
| hsa-miR-574-3p | 0.14 | 0.14 | 0.14 | increase |
| hsa-miR-636 | 0.41 | 0.41 | | increase |
| hsa-miR-7641 | 0.11 | 0.11 | | increase |
| hsa-miR-92a-1-5p | 0.14 | 0.14 | 0.14 | increase |
| hsa-miR-99a-5p | 0.63 | 0.63 | 0.63 | increase |

TABLE 8

| MicroRNA | No expression cut-off | Measurable expression in >50% of the samples | Measurable expression in >80% of the samples | Change in expression |
|---|---|---|---|---|
| hsa-let-7d-3p | 3.46 | 3.46 | 3.46 | increase |
| hsa-let-7i-5p | 43.10 | 43.10 | 43.10 | increase |
| hsa-miR-101-3p | −7.20 | −7.20 | −7.20 | decrease |
| hsa-miR-106b-5p | −1.31 | −1.31 | −1.31 | decrease |
| hsa-miR-124-3p | −0.39 | | | decrease |
| hsa-miR-1260a | 1.18 | 1.18 | 1.18 | increase |
| hsa-miR-1260b | 0.89 | 0.89 | 0.89 | increase |
| hsa-miR-130b-3p | −2.50 | −2.50 | −2.50 | decrease |
| hsa-miR-133a-3p | −0.48 | −0.48 | −0.48 | decrease |
| hsa-miR-136-5p | −0.13 | −0.13 | | decrease |
| hsa-miR-139-3p | 0.14 | | | increase |
| hsa-miR-144-3p | −2.50 | −2.50 | −2.50 | decrease |
| hsa-miR-181c-5p | −2.27 | −2.27 | −2.27 | decrease |
| hsa-miR-1908-5p | 0.20 | 0.20 | 0.20 | increase |
| hsa-miR-193a-5p | 0.13 | 0.13 | | increase |
| hsa-miR-197-3p | 0.72 | 0.72 | 0.72 | increase |
| hsa-miR-199a-5p | −1.36 | −1.36 | −1.36 | decrease |
| hsa-miR-19a-3p | −2.38 | −2.38 | −2.38 | decrease |
| hsa-miR-204-5p | −2.58 | −2.58 | −2.58 | decrease |
| hsa-miR-223-5p | 0.63 | 0.63 | 0.63 | increase |
| hsa-miR-224-5p | 0.47 | 0.47 | 0.47 | increase |
| hsa-miR-23a-5p | 0.66 | 0.66 | 0.66 | increase |
| hsa-miR-29c-3p | −0.30 | −0.30 | −0.30 | decrease |
| hsa-miR-301b-3p | −0.40 | −0.40 | −0.40 | decrease |
| hsa-miR-30a-5p | −2.91 | −2.91 | −2.91 | decrease |
| hsa-miR-30e-3p | 3.05 | 3.05 | 3.05 | increase |
| hsa-miR-338-3p | −0.34 | −0.34 | −0.34 | decrease |
| hsa-miR-4433b-5p | 2.30 | 2.30 | 2.30 | increase |
| hsa-miR-4446-3p | 1.48 | 1.48 | 1.48 | increase |
| hsa-miR-497-5p | −0.14 | −0.14 | −0.14 | decrease |
| hsa-miR-548e-3p | −0.11 | −0.11 | −0.11 | decrease |
| hsa-miR-9-5p | −1.35 | | | decrease |

TABLE 9

| MicroRNA | No expression cut-off | Measurable expression in >50% of the samples | Measurable expression in >80% of the samples | Change in expression |
|---|---|---|---|---|
| hsa-miR-101-3p | −0.14 | −0.14 | −0.14 | decrease |
| hsa-miR-1298-5p | 0.22 | 0.22 | | increase |
| hsa-miR-204-5p | 10.26 | 10.26 | 10.26 | increase |
| hsa-miR-210-3p | 0.12 | 0.12 | 0.12 | increase |
| hsa-miR-22-3p | 3.04 | 3.04 | 3.04 | increase |
| hsa-miR-221-3p | 0.32 | 0.32 | 0.32 | increase |
| hsa-miR-30a-5p | 0.20 | 0.20 | 0.20 | increase |
| hsa-miR-34c-5p | 0.11 | 0.11 | | increase |
| hsa-miR-378a-3p | 1.42 | 1.42 | 1.42 | increase |

TABLE 10

| MicroRNA | No expression cut-off | Measurable expression in >50% of the samples | Measurable expression in >80% of the samples | Change in expression |
|---|---|---|---|---|
| hsa-let-7c-5p | 3.06 | 3.06 | 3.06 | increase |
| hsa-miR-100-5p | 0.89 | 0.89 | 0.89 | increase |
| hsa-miR-106a-5p | 0.35 | 0.35 | 0.35 | increase |
| hsa-miR-1180-3p | 1.14 | 1.14 | 1.14 | increase |
| hsa-miR-124-3p | 0.19 | | | increase |
| hsa-miR-125b-1-3p | 0.28 | 0.28 | | increase |
| hsa-miR-125b-2-3p | 1.05 | 1.05 | 1.05 | increase |
| hsa-miR-125b-5p | 2.14 | 2.14 | 2.14 | increase |
| hsa-miR-1260a | 0.17 | 0.17 | 0.17 | increase |
| hsa-miR-1264 | 0.19 | | | increase |
| hsa-miR-1287-5p | 0.74 | 0.74 | 0.74 | increase |
| hsa-miR-129-5p | 0.14 | | | increase |
| hsa-miR-1298-3p | 1.64 | | | increase |
| hsa-miR-1298-5p | 20.65 | 20.65 | | increase |
| hsa-miR-1323 | 0.17 | | | increase |
| hsa-miR-135a-5p | 0.30 | | | increase |
| hsa-miR-136-3p | 0.58 | 0.58 | 0.58 | increase |
| hsa-miR-138-5p | 0.21 | 0.21 | | increase |
| hsa-miR-143-3p | 13.64 | 13.64 | 13.64 | increase |
| hsa-miR-149-5p | 0.17 | | | increase |
| hsa-miR-150-3p | 0.55 | 0.55 | 0.55 | increase |
| hsa-miR-152-3p | 0.16 | 0.16 | 0.16 | increase |
| hsa-miR-181c-5p | 1.23 | 1.23 | 1.23 | increase |
| hsa-miR-185-3p | 0.50 | 0.50 | 0.50 | increase |
| hsa-miR-18a-5p | 0.21 | 0.21 | | increase |
| hsa-miR-1911-3p | 0.13 | | | increase |
| hsa-miR-1911-5p | 7.80 | | | increase |
| hsa-miR-1912 | 0.32 | | | increase |
| hsa-miR-193b-3p | 0.10 | | | increase |
| hsa-miR-193b-5p | 0.19 | 0.19 | | increase |
| hsa-miR-195-5p | 0.92 | 0.92 | | increase |
| hsa-miR-199b-5p | 0.24 | 0.24 | 0.24 | increase |
| hsa-miR-204-3p | 0.29 | | | increase |
| hsa-miR-204-5p | 953.10 | 953.10 | 953.10 | increase |
| hsa-miR-210-3p | 11.82 | 11.82 | 11.82 | increase |
| hsa-miR-211-5p | 0.16 | | | increase |
| hsa-miR-215-5p | 0.51 | 0.51 | 0.51 | increase |
| hsa-miR-219a-2-3p | 0.17 | | | increase |
| hsa-miR-22-3p | 313.33 | 313.33 | 313.33 | increase |
| hsa-miR-221-3p | 22.12 | 22.12 | 22.12 | increase |
| hsa-miR-23a-3p | 1.30 | 1.30 | 1.30 | increase |
| hsa-miR-23b-3p | 1.11 | 1.11 | 1.11 | increase |
| hsa-miR-27b-5p | 0.25 | 0.25 | 0.25 | increase |
| hsa-miR-296-5p | 0.14 | | | increase |
| hsa-miR-29c-3p | 0.76 | 0.76 | 0.76 | increase |
| hsa-miR-30a-3p | 1.38 | 1.38 | 1.38 | increase |
| hsa-miR-30a-5p | 20.54 | 20.54 | 20.54 | increase |
| hsa-miR-30d-3p | 0.35 | 0.35 | 0.35 | increase |
| hsa-miR-3155a | 0.19 | | | increase |
| hsa-miR-3155b | 0.19 | | | increase |
| hsa-miR-320a | 230.66 | 230.66 | 230.66 | increase |
| hsa-miR-320c | 2.12 | 2.12 | 2.12 | increase |
| hsa-miR-323b-3p | 0.12 | 0.12 | | increase |
| hsa-miR-324-3p | 0.32 | 0.32 | 0.32 | increase |
| hsa-miR-324-5p | 0.18 | 0.18 | | increase |
| hsa-miR-328-3p | 0.48 | 0.48 | 0.48 | increase |
| hsa-miR-331-3p | 0.19 | 0.19 | | increase |
| hsa-miR-339-3p | 1.20 | 1.20 | 1.20 | increase |
| hsa-miR-33a-5p | 0.18 | 0.18 | | increase |
| hsa-miR-33b-5p | 2.78 | 2.78 | 2.78 | increase |
| hsa-miR-345-5p | 0.94 | 0.94 | 0.94 | increase |
| hsa-miR-34b-3p | 0.78 | | | increase |
| hsa-miR-34b-5p | 0.95 | | | increase |
| hsa-miR-34c-3p | 0.33 | | | increase |
| hsa-miR-34c-5p | 10.24 | 10.24 | | increase |
| hsa-miR-3605-3p | 0.14 | 0.14 | | increase |
| hsa-miR-361-3p | 0.33 | 0.33 | 0.33 | increase |
| hsa-miR-3656 | 0.12 | | | increase |
| hsa-miR-378a-3p | 156.67 | 156.67 | 156.67 | increase |
| hsa-miR-378c | 7.71 | 7.71 | 7.71 | increase |
| hsa-miR-378d | 0.43 | 0.43 | 0.43 | increase |
| hsa-miR-378i | 4.25 | 4.25 | 4.25 | increase |
| hsa-miR-3960 | 0.51 | 0.51 | | increase |
| hsa-miR-423-5p | 825.39 | 825.39 | 825.39 | increase |
| hsa-miR-424-5p | 0.47 | 0.47 | 0.47 | increase |
| hsa-miR-4440 | 0.13 | | | increase |
| hsa-miR-4449 | 0.22 | 0.22 | | increase |
| hsa-miR-4466 | 0.14 | | | increase |
| hsa-miR-448 | 0.54 | | | increase |
| hsa-miR-4492 | 0.19 | | | increase |
| hsa-miR-449a | 0.35 | | | increase |
| hsa-miR-4508 | 1.32 | 1.32 | 1.32 | increase |
| hsa-miR-4647 | 0.47 | | | increase |
| hsa-miR-4742-3p | 0.29 | 0.29 | | increase |
| hsa-miR-4745-5p | 0.21 | | | increase |
| hsa-miR-4772-5p | 0.25 | | | increase |
| hsa-miR-4785 | 0.13 | | | increase |
| hsa-miR-4792 | 0.47 | 0.47 | | increase |
| hsa-miR-483-3p | 0.32 | | | increase |
| hsa-miR-497-5p | 1.24 | 1.24 | 1.24 | increase |
| hsa-miR-502-3p | 0.41 | 0.41 | 0.41 | increase |
| hsa-miR-5096 | 0.22 | 0.22 | | increase |
| hsa-miR-512-3p | 0.26 | | | increase |
| hsa-miR-515-5p | 0.32 | | | increase |
| hsa-miR-516a-5p | 0.68 | | | increase |
| hsa-miR-516b-5p | 0.29 | | | increase |
| hsa-miR-517a-3p | 0.15 | | | increase |
| hsa-miR-517b-3p | 0.15 | | | increase |
| hsa-miR-532-5p | 2.55 | 2.55 | 2.55 | increase |
| hsa-miR-548am-5p | 0.20 | 0.20 | | increase |
| hsa-miR-548au-5p | 0.20 | 0.20 | | increase |
| hsa-miR-548c-5p | 0.20 | 0.20 | | increase |
| hsa-miR-548o-5p | 0.20 | 0.20 | | increase |
| hsa-miR-550a-3p | −0.16 | −0.16 | −0.16 | decrease |
| hsa-miR-5689 | 0.16 | | | increase |
| hsa-miR-574-3p | 0.26 | 0.26 | 0.26 | increase |
| hsa-miR-576-3p | 0.24 | 0.24 | | increase |
| hsa-miR-592 | 0.28 | | | increase |
| hsa-miR-6087 | 0.29 | 0.29 | | increase |
| hsa-miR-616-5p | 0.27 | 0.27 | | increase |
| hsa-miR-627-5p | 1.55 | 1.55 | 1.55 | increase |
| hsa-miR-636 | 0.70 | 0.70 | | increase |
| hsa-miR-6501-5p | 0.20 | | | increase |
| hsa-miR-652-3p | 0.89 | 0.89 | 0.89 | increase |
| hsa-miR-664a-3p | 0.22 | 0.22 | | increase |
| hsa-miR-6735-5p | 0.11 | 0.11 | | increase |
| hsa-miR-6741-3p | 0.20 | 0.20 | | increase |
| hsa-miR-6820-5p | 0.27 | | | increase |
| hsa-miR-7641 | 0.15 | 0.15 | | increase |
| hsa-miR-7977 | 0.11 | 0.11 | | increase |
| hsa-miR-873-3p | 0.66 | 0.66 | | increase |
| hsa-miR-873-5p | 0.28 | | | increase |
| hsa-miR-874-3p | 0.11 | 0.11 | | increase |
| hsa-miR-885-5p | 0.19 | | | increase |
| hsa-miR-9-5p | 1.17 | 1.17 | 1.17 | increase |
| hsa-miR-92a-1-5p | 0.22 | 0.22 | 0.22 | increase |
| hsa-miR-92b-3p | 2.80 | 2.80 | 2.80 | increase |
| hsa-miR-99a-3p | 0.32 | | | increase |

TABLE 10-continued

| MicroRNA | No expression cut-off | Measurable expression in >50% of the samples | Measurable expression in >80% of the samples | Change in expression |
|---|---|---|---|---|
| hsa-miR-99a-5p | 1.10 | 1.10 | 1.10 | increase |
| hsa-miR-99b-5p | 4.04 | 4.04 | 4.04 | increase |

TABLE 11

| MicroRNA | No expression cut-off | Measurable expression in >50% of the samples | Measurable expression in >80% of the samples | Change in expression |
|---|---|---|---|---|
| hsa-let-7d-3p | 5.17 | 5.17 | 5.17 | increase |
| hsa-let-7i-5p | 65.68 | 65.68 | 65.68 | increase |
| hsa-miR-101-3p | −11.51 | −11.51 | −11.51 | decrease |
| hsa-miR-106b-5p | −1.68 | −1.68 | −1.68 | decrease |
| hsa-miR-1260a | 1.62 | 1.62 | 1.62 | increase |
| hsa-miR-1260b | 1.17 | 1.17 | 1.17 | increase |
| hsa-miR-139-3p | 0.17 | | | increase |
| hsa-miR-144-3p | −4.16 | −4.16 | −4.16 | decrease |
| hsa-miR-181c-5p | −2.86 | −2.86 | −2.86 | decrease |
| hsa-miR-1908-5p | 0.28 | 0.28 | 0.28 | increase |
| hsa-miR-193a-5p | 0.17 | 0.17 | | increase |
| hsa-miR-197-3p | 1.09 | 1.09 | 1.09 | increase |
| hsa-miR-19a-3p | −3.70 | −3.70 | −3.70 | decrease |
| hsa-miR-224-5p | 0.79 | 0.79 | 0.79 | increase |
| hsa-miR-29c-3p | −0.39 | −0.39 | −0.39 | decrease |
| hsa-miR-30a-5p | −3.65 | −3.65 | −3.65 | decrease |
| hsa-miR-330-5p | −0.17 | −0.17 | −0.17 | decrease |
| hsa-miR-338-3p | −0.39 | −0.39 | −0.39 | decrease |
| hsa-miR-4446-3p | 1.85 | 1.85 | 1.85 | increase |
| hsa-miR-497-5p | −0.14 | −0.14 | −0.14 | decrease |
| hsa-miR-548e-3p | −0.11 | −0.11 | −0.11 | decrease |
| hsa-miR-92a-3p | 227.90 | 227.90 | 227.90 | increase |

TABLE 12

| MicroRNA | No expression cut-off | Measurable expression in >50% of the samples | Measurable expression in >80% of the samples | Change in expression |
|---|---|---|---|---|
| hsa-miR-125a-5p | −2.26 | −2.26 | −2.26 | decrease |
| hsa-miR-130a-3p | −2.07 | −2.07 | −2.07 | decrease |
| hsa-miR-146b-5p | −4.50 | −4.50 | −4.50 | decrease |
| hsa-miR-203a-3p | 1.56 | 1.56 | 1.56 | increase |
| hsa-miR-205-5p | 0.62 | 0.62 | 0.62 | increase |
| hsa-miR-22-5p | 0.21 | 0.21 | 0.21 | decrease |
| hsa-miR-370-3p | −0.14 | −0.14 | | decrease |
| hsa-miR-424-3p | 0.50 | 0.50 | 0.50 | increase |
| hsa-miR-574-5p | 0.22 | 0.22 | 0.22 | increase |

TABLE 13

| MicroRNA | No expression cut-off | Measurable expression in >50% of the samples | Measurable expression in >80% of the samples | Change in expression |
|---|---|---|---|---|
| hsa-miR-101-5p | 0.32 | | | increase |
| hsa-miR-10b-5p | 48.24 | 48.24 | 48.24 | increase |
| hsa-miR-1298-5p | 0.79 | | | increase |
| hsa-miR-133a-3p | −1.28 | −1.28 | −1.28 | decrease |
| hsa-miR-145-5p | −0.26 | −0.26 | −0.26 | decrease |
| hsa-miR-151a-3p | 74.33 | 74.33 | 74.33 | increase |
| hsa-miR-16-2-3p | 4.06 | 4.06 | 4.06 | increase |
| hsa-miR-181a-2-3p | 0.69 | 0.69 | | increase |
| hsa-miR-185-5p | 1.37 | 1.37 | 1.37 | increase |
| hsa-miR-192-5p | 11.80 | 11.80 | 11.80 | increase |
| hsa-miR-195-3p | 0.22 | | | increase |
| hsa-miR-24-3p | 4.85 | 4.85 | 4.85 | increase |
| hsa-miR-25-3p | 73.84 | 73.84 | 73.84 | increase |
| hsa-miR-28-3p | 46.52 | 46.52 | 46.52 | increase |
| hsa-miR-301a-3p | −2.58 | −2.58 | −2.58 | decrease |
| hsa-miR-30a-5p | 7.14 | 7.14 | 7.14 | decrease |
| hsa-miR-3130-3p | 0.17 | | | increase |
| hsa-miR-3150b-3p | 0.12 | | | increase |
| hsa-miR-3200-5p | 0.19 | | | increase |
| hsa-miR-342-3p | 0.93 | 0.93 | 0.93 | increase |
| hsa-miR-382-5p | −0.26 | −0.26 | | decrease |
| hsa-miR-4745-3p | 0.10 | | | increase |
| hsa-miR-484 | 8.40 | 8.40 | 8.40 | increase |
| hsa-miR-625-3p | −0.86 | −0.86 | −0.86 | decrease |
| hsa-miR-625-5p | −1.14 | −1.14 | −1.14 | decrease |

TABLE 14

| MicroRNA | No expression cut-off | Measurable expression in >50% of the samples | Measurable expression in >80% of the samples | Change in expression |
|---|---|---|---|---|
| hsa-miR-146b-5p | −0.11 | −0.11 | −0.11 | decrease |
| hsa-miR-151a-3p | −0.20 | −0.20 | −0.20 | decrease |
| hsa-miR-182-5p | −0.35 | −0.35 | −0.35 | decrease |
| hsa-miR-194-5p | 0.14 | 0.14 | 0.14 | increase |
| hsa-miR-30b-5p | 0.16 | 0.16 | 0.16 | increase |
| hsa-miR-320b | −0.14 | −0.14 | −0.14 | decrease |
| hsa-miR-92a-3p | 1.24 | 1.24 | 1.24 | increase |

TABLE 15

| MicroRNA | No expression cut-off | Measurable expression in >50% of the samples | Measurable expression in >80% of the samples | Change in expression |
|---|---|---|---|---|
| hsa-let-7a-5p | −2.11 | −2.11 | −2.11 | decrease |
| hsa-let-7b-5p | −0.55 | −0.55 | −0.55 | decrease |
| hsa-let-7c-5p | −0.48 | −0.48 | −0.48 | decrease |
| hsa-let-7e-5p | −0.26 | −0.26 | −0.26 | decrease |
| hsa-let-7f-5p | −1.98 | −1.98 | −1.98 | decrease |
| hsa-miR-130a-3p | 0.34 | 0.34 | 0.34 | increase |
| hsa-miR-203a-3p | 2.70 | 2.70 | 2.70 | increase |
| hsa-miR-21-5p | −0.21 | −0.21 | −0.21 | decrease |
| hsa-miR-27a-3p | 0.17 | 0.17 | 0.17 | increase |
| hsa-miR-28-3p | 0.52 | 0.52 | 0.52 | increase |
| hsa-miR-375 | −2.02 | −2.02 | −2.02 | decrease |
| hsa-miR-378a-3p | 2.03 | 2.03 | 2.03 | increase |
| hsa-miR-423-5p | 1.80 | 1.80 | 1.80 | increase |
| hsa-miR-92a-3p | −1.31 | −1.31 | −1.31 | decrease |

TABLE 16

| MicroRNA | No expression cut-off | Measurable expression in >50% of the samples | Measurable expression in >80% of the samples | Change in expression |
|---|---|---|---|---|
| hsa-miR-182-5p | −0.18 | −0.18 | −0.18 | decrease |
| hsa-miR-92a-3p | 0.59 | 0.59 | 0.59 | increase |

TABLE 17

| MicroRNA | No expression cut-off | Measurable expression in >50% of the samples | Measurable expression in >80% of the samples | Change in expression |
|---|---|---|---|---|
| hsa-let-7a-5p | −1.12 | −1.12 | −1.12 | decrease |
| hsa-let-7b-5p | −0.30 | −0.30 | −0.30 | decrease |
| hsa-let-7c-5p | −0.27 | −0.27 | −0.27 | decrease |
| hsa-let-7e-5p | −0.13 | −0.13 | −0.13 | decrease |
| hsa-let-7f-5p | −1.04 | −1.04 | −1.04 | decrease |
| hsa-miR-130a-3p | 0.19 | 0.19 | 0.19 | increase |
| hsa-miR-203a-3p | 1.50 | 1.50 | 1.50 | increase |
| hsa-miR-21-5p | −0.11 | −0.11 | −0.11 | decrease |
| hsa-miR-28-3p | 0.32 | 0.32 | 0.32 | increase |
| hsa-miR-375 | −1.06 | −1.06 | −1.06 | decrease |
| hsa-miR-378a-3p | 1.20 | 1.20 | 1.20 | increase |
| hsa-miR-423-5p | 1.03 | 1.03 | 1.03 | increase |
| hsa-miR-92a-3p | −0.71 | −0.71 | −0.71 | decrease |

TABLE 18

| MicroRNA | No expression cut-off | Measurable expression in >50% of the samples | Measurable expression in >80% of the samples | Change in expression |
|---|---|---|---|---|
| hsa-miR-122-5p | −1.09 | −1.09 | | increase |
| hsa-miR-1307-5p | 0.33 | 0.33 | 0.33 | increase |
| hsa-miR-138-5p | 0.28 | 0.28 | 0.28 | increase |
| hsa-miR-146b-5p | −1.69 | −1.69 | −1.69 | increase |
| hsa-miR-148a-5p | −0.25 | −0.25 | −0.25 | increase |
| hsa-miR-182-5p | −4.63 | −4.63 | −4.63 | increase |
| hsa-miR-23b-3p | −0.52 | −0.52 | −0.52 | increase |
| hsa-miR-339-3p | 0.10 | 0.10 | 0.10 | increase |
| hsa-miR-4454 | −0.15 | −0.15 | −0.15 | increase |
| hsa-miR-4492 | −0.23 | −0.23 | −0.23 | increase |
| hsa-miR-7977 | −0.15 | −0.15 | −0.15 | increase |
| hsa-miR-874-3p | 0.17 | 0.17 | 0.17 | increase |

TABLE 19

| MicroRNA | No expression cut-off | Measurable expression in >50% of the samples | Measurable expression in >80% of the samples | Change in expression |
|---|---|---|---|---|
| hsa-let-7a-5p | −12.80 | −12.80 | −12.80 | increase |
| hsa-let-7d-5p | −0.23 | −0.23 | −0.23 | increase |
| hsa-let-7g-5p | −0.49 | −0.49 | −0.49 | increase |
| hsa-miR-200b-3p | −0.66 | −0.66 | −0.66 | decrease |
| hsa-miR-28-3p | 3.85 | 3.85 | 3.85 | decrease |
| hsa-miR-99a-5p | 0.49 | 0.49 | 0.49 | decrease |

TABLE 20

| MicroRNA | No expression cut-off | Measurable expression in at least 50% of the samples | Measurable expression in at least 80% of the samples | Change in expression |
|---|---|---|---|---|
| hsa-miR-423-3p | 0.11 | 0.11 | 0.11 | increase |
| hsa-miR-423-5p | 0.35 | 0.35 | 0.35 | increase |

TABLE 21

| MicroRNA | No expression cut-off | Measurable expression in at least 50% of the samples | Measurable expression in at least 80% of the samples | Change in expression |
|---|---|---|---|---|
| hsa-miR-203a-3p | 0.40 | 0.40 | 0.40 | increase |

TABLE 22

| MicroRNA | No expression cut-off | Measurable expression in >50% of the samples | Measurable expression in >80% of the samples | Change in expression |
|---|---|---|---|---|
| hsa-miR-125b-5p | 0.95 | 0.95 | 0.95 | increase |
| hsa-miR-1307-3p | 0.20 | 0.20 | 0.20 | increase |
| hsa-miR-1307-5p | 0.27 | 0.27 | 0.27 | increase |
| hsa-miR-146b-5p | −1.43 | −1.43 | −1.43 | decrease |
| hsa-miR-15b-5p | 0.10 | 0.10 | 0.10 | increase |
| hsa-miR-181c-5p | −0.34 | −0.34 | −0.34 | decrease |
| hsa-miR-193b-3p | 0.11 | 0.11 | 0.11 | increase |
| hsa-miR-19a-3p | 0.14 | 0.14 | 0.14 | increase |
| hsa-miR-23b-3p | −0.53 | −0.53 | −0.53 | decrease |
| hsa-miR-27b-3p | −15.89 | −15.89 | −15.89 | decrease |
| hsa-miR-30d-3p | −0.12 | −0.12 | −0.12 | decrease |
| hsa-miR-30e-3p | −0.80 | −0.80 | −0.80 | decrease |
| hsa-miR-31-5p | 0.23 | 0.23 | 0.23 | increase |
| hsa-miR-339-3p | 0.14 | 0.14 | 0.14 | increase |
| hsa-miR-423-3p | 10.61 | 10.61 | 10.61 | increase |
| hsa-miR-423-5p | 29.59 | 29.59 | 29.59 | increase |
| hsa-miR-4449 | 0.18 | 0.18 | | increase |
| hsa-miR-4492 | −0.24 | −0.24 | −0.24 | decrease |
| hsa-miR-454-3p | 0.13 | 0.13 | | increase |
| hsa-miR-484 | 0.43 | 0.43 | 0.43 | increase |
| hsa-miR-509-3p | 0.19 | 0.19 | 0.19 | increase |
| hsa-miR-874-3p | 0.23 | 0.23 | 0.23 | increase |
| hsa-miR-9-5p | −0.10 | −0.10 | −0.10 | decrease |

TABLE 23

| MicroRNA | No expression cut-off | Measurable expression in >50% of the samples | Measurable expression in >80% of the samples | Change in expression |
|---|---|---|---|---|
| hsa-let-7g-5p | −0.67 | −0.67 | −0.67 | decrease |
| hsa-miR-130a-3p | 3.02 | 3.02 | 3.02 | increase |
| hsa-miR-200b-3p | −1.50 | −1.50 | −1.50 | decrease |
| hsa-miR-92a-3p | −13.60 | −13.60 | −13.60 | decrease |

TABLE 24

| MicroRNA | No expression cut-off | Measurable expression in >50% of the samples | Measurable expression in >80% of the samples | Change in expression |
|---|---|---|---|---|
| hsa-let-7a-5p | −38.88 | −38.88 | −38.88 | decrease |
| hsa-let-7b-5p | −10.19 | −10.19 | −10.19 | decrease |
| hsa-let-7c-5p | −9.19 | −9.19 | −9.19 | decrease |
| hsa-let-7d-5p | −0.50 | −0.50 | −0.50 | decrease |
| hsa-let-7e-5p | −4.79 | −4.79 | −4.79 | decrease |
| hsa-let-7f-5p | −35.53 | −35.53 | −35.53 | decrease |
| hsa-let-7g-5p | −1.28 | −1.28 | −1.28 | decrease |
| hsa-miR-130a-3p | 5.82 | 5.82 | 5.82 | increase |
| hsa-miR-200b-3p | −1.81 | −1.81 | −1.81 | decrease |
| hsa-miR-203a-3p | 46.39 | 46.39 | 46.39 | increase |
| hsa-miR-27a-3p | 3.00 | 3.00 | 3.00 | increase |
| hsa-miR-28-3p | 9.28 | 9.28 | 9.28 | increase |
| hsa-miR-375 | −40.17 | −40.17 | −40.17 | decrease |
| hsa-miR-378a-3p | 38.30 | 38.30 | 38.30 | increase |
| hsa-miR-423-5p | 33.95 | 33.95 | 33.95 | increase |
| hsa-miR-92a-3p | −24.72 | −24.72 | −24.72 | decrease |
| hsa-miR-99a-5p | 0.89 | 0.89 | 0.89 | increase |

TABLE 25

| MicroRNA | No expression cut-off | Measurable expression in >50% of the samples | Measurable expression in >80% of the samples | Change in expression |
|---|---|---|---|---|
| hsa-let-7a-5p | −38.88 | −38.88 | −38.88 | decrease |
| hsa-let-7b-5p | −10.19 | −10.19 | −10.19 | decrease |
| hsa-let-7c-5p | −9.19 | −9.19 | −9.19 | decrease |
| hsa-let-7d-5p | −0.50 | −0.50 | −0.50 | decrease |
| hsa-let-7e-5p | −4.79 | −4.79 | −4.79 | decrease |
| hsa-let-7f-5p | −35.53 | −35.53 | −35.53 | decrease |
| hsa-let-7g-5p | −1.28 | −1.28 | −1.28 | decrease |
| hsa-miR-130a-3p | 5.82 | 5.82 | 5.82 | increase |
| hsa-miR-200b-3p | −1.81 | −1.81 | −1.81 | decrease |
| hsa-miR-203a-3p | 46.39 | 46.39 | 46.39 | increase |
| hsa-miR-27a-3p | 3.00 | 3.00 | 3.00 | increase |
| hsa-miR-28-3p | 9.28 | 9.28 | 9.28 | increase |
| hsa-miR-375 | −40.17 | −40.17 | −40.17 | decrease |
| hsa-miR-378a-3p | 38.30 | 38.30 | 38.30 | increase |
| hsa-miR-423-5p | 33.95 | 33.95 | 33.95 | increase |
| hsa-miR-92a-3p | −24.72 | −24.72 | −24.72 | decrease |
| hsa-miR-99a-5p | 0.89 | 0.89 | 0.89 | increase |

TABLE 26

| MicroRNA | No expression cut-off | Measurable expression in >50% of the samples | Measurable expression in >80% of the samples | Change in expression |
|---|---|---|---|---|
| hsa-let-7a-5p | x | x | x | increase |
| hsa-let-7c-5p | x | x | x | increase |
| hsa-miR-125a-5p | x | x | x | increase |
| hsa-miR-200b-3p | x | x | x | increase |
| hsa-miR-92b-3p | x | x | x | increase |
| hsa-miR-140-3p | x | x | x | decrease |
| hsa-miR-186-5p | x | x | x | decrease |
| hsa-miR-30e-5p | x | x | x | decrease |
| hsa-miR-93-5p | x | x | x | decrease |

TABLE 27

| MicroRNA | No expression cut-off | Measurable expression in >50% of the samples | Measurable expression in >80% of the samples | Change in expression |
|---|---|---|---|---|
| hsa-let-7a-5p | x | x | x | increase |
| hsa-let-7c-5p | x | x | x | increase |
| hsa-miR-200b-3p | x | x | x | increase |
| hsa-miR-92b-3p | x | x | x | increase |
| hsa-miR-140-3p | x | x | x | decrease |
| hsa-miR-186-5p | x | x | x | decrease |
| hsa-miR-30e-5p | x | x | x | decrease |

TABLE 28

| MicroRNA | No expression cut-off | Measurable expression in >50% of the samples | Measurable expression in >80% of the samples | Change in expression |
|---|---|---|---|---|
| hsa-miR-125a-5p | x | x | x | increase |
| hsa-miR-130a-3p | x | x | x | increase |
| hsa-miR-99b-5p | x | x | x | increase |
| hsa-let-7f-5p | x | x | x | increase |
| hsa-miR-15b-5p | x | x | x | increase |
| hsa-miR-193b-3p | x | x | x | increase |
| hsa-miR-374b-5p | x | x | x | increase |
| hsa-miR-582-5p | x | x | x | increase |
| hsa-miR-1260a | x | x | x | increase |
| hsa-miR-191-5p | x | x | x | increase |
| hsa-miR-2115-3p | x | x | x | increase |
| hsa-miR-32-5p | x | x | x | increase |
| hsa-miR-335-5p | x | x | x | increase |
| hsa-miR-365a-3p | x | x | x | increase |
| hsa-miR-365b-3p | x | x | x | increase |
| hsa-miR-590-3p | x | x | x | increase |
| hsa-miR-664a-3p | x | x | x | increase |
| hsa-miR-766-3p | x | x | x | increase |
| hsa-miR-885-5p | x | x | x | increase |
| hsa-miR-4732-3p | x | x |  | increase |
| hsa-miR-192-3p | x |  |  | increase |
| hsa-miR-1307-3p | x | x | x | decrease |
| hsa-miR-140-3p | x | x | x | decrease |
| hsa-miR-140-5p | x | x | x | decrease |
| hsa-miR-181b-5p | x | x | x | decrease |
| hsa-miR-181d-5p | x | x | x | decrease |
| hsa-miR-185-5p | x | x | x | decrease |
| hsa-miR-186-5p | x | x | x | decrease |
| hsa-miR-27a-5p | x | x | x | decrease |
| hsa-miR-324-5p | x | x | x | decrease |
| hsa-miR-361-3p | x | x | x | decrease |
| hsa-miR-3615 | x | x | x | decrease |
| hsa-miR-378i | x | x | x | decrease |
| hsa-miR-423-3p | x | x | x | decrease |
| hsa-miR-425-3p | x | x | x | decrease |
| hsa-miR-548e-5p | x | x | x | decrease |

TABLE 29

| MicroRNA | No expression cut-off | Measurable expression in >50% of the samples | Measurable expression in >80% of the samples | Change in expression |
|---|---|---|---|---|
| hsa-miR-125a-5p | x | x | x | increase |
| hsa-miR-130a-3p | x | x | x | increase |
| hsa-miR-99b-5p | x | x | x | increase |
| hsa-miR-15b-5p | x | x | x | increase |
| hsa-miR-193b-3p | x | x | x | increase |
| hsa-miR-374b-5p | x | x | x | increase |
| hsa-miR-582-5p | x | x | x | increase |
| hsa-miR-140-3p | x | x | x | decrease |
| hsa-miR-140-5p | x | x | x | decrease |
| hsa-miR-181b-5p | x | x | x | decrease |
| hsa-miR-181d-5p | x | x | x | decrease |
| hsa-miR-185-5p | x | x | x | decrease |
| hsa-miR-186-5p | x | x | x | decrease |
| hsa-miR-27a-5p | x | x | x | decrease |
| hsa-miR-324-5p | x | x | x | decrease |
| hsa-miR-361-3p | x | x | x | decrease |
| hsa-miR-3615 | x | x | x | decrease |
| hsa-miR-378i | x | x | x | decrease |
| hsa-miR-423-3p | x | x | x | decrease |
| hsa-miR-425-3p | x | x | x | decrease |

TABLE 30

| MicroRNA | No expression cut-off | Measurable expression in >50% of the samples | Measurable expression in >80% of the samples | Change in expression |
|---|---|---|---|---|
| hsa-miR-125a-5p | x | x | x | increase |
| hsa-miR-130a-3p | x | x | x | increase |
| hsa-miR-99b-5p | x | x | x | increase |
| hsa-miR-125b-5p | x | x | x | increase |
| hsa-miR-132-3p | x | x | x | increase |
| hsa-miR-15b-5p | x | x | x | increase |
| hsa-miR-193b-3p | x | x | x | increase |
| hsa-miR-203a-3p | x | x | x | increase |
| hsa-miR-224-5p | x | x | x | increase |

TABLE 30-continued

| MicroRNA | No expression cut-off | Measurable expression in >50% of the samples | Measurable expression in >80% of the samples | Change in expression |
|---|---|---|---|---|
| hsa-miR-340-3p | x | x | x | increase |
| hsa-miR-342-5p | x | x | x | increase |
| hsa-miR-374b-5p | x | x | x | increase |
| hsa-miR-582-5p | x | x | x | increase |
| hsa-miR-877-5p | x | x | x | increase |
| hsa-miR-944 | x | x | x | increase |
| hsa-miR-106b-3p | x | x | x | decrease |
| hsa-miR-140-3p | x | x | x | decrease |
| hsa-miR-140-5p | x | x | x | decrease |
| hsa-miR-181b-5p | x | x | x | decrease |
| hsa-miR-181c-3p | x | x | x | decrease |
| hsa-miR-181d-5p | x | x | x | decrease |
| hsa-miR-185-5p | x | x | x | decrease |
| hsa-miR-186-5p | x | x | x | decrease |
| hsa-miR-204-5p | x | x | x | decrease |
| hsa-miR-24-3p | x | x | x | decrease |
| hsa-miR-27a-5p | x | x | x | decrease |
| hsa-miR-324-5p | x | x | x | decrease |
| hsa-miR-345-5p | x | x | x | decrease |
| hsa-miR-34a-5p | x | x | x | decrease |
| hsa-miR-361-3p | x | x | x | decrease |
| hsa-miR-3615 | x | x | x | decrease |
| hsa-miR-378i | x | x | x | decrease |
| hsa-miR-3909 | x | x | x | decrease |
| hsa-miR-423-3p | x | x | x | decrease |
| hsa-miR-425-3p | x | x | x | decrease |
| hsa-miR-484 | x | x | x | decrease |
| hsa-miR-5010-5p | x | x | x | decrease |
| hsa-miR-542-5p | x | | | decrease |
| hsa-miR-629-5p | x | x | x | decrease |
| hsa-miR-7-5p | x | | | decrease |
| hsa-miR-93-5p | x | x | x | decrease |

TABLE 31

| MicroRNA | No expression cut-off | Measurable expression in >50% of the samples | Measurable expression in >80% of the samples | Change in expression |
|---|---|---|---|---|
| hsa-let-7a-5p | x | x | x | increase |
| hsa-let-7c-5p | x | x | x | increase |
| hsa-miR-125a-5p | x | x | x | increase |
| hsa-miR-200b-3p | x | x | x | increase |
| hsa-miR-130a-3p | x | x | x | increase |
| hsa-miR-92b-3p | x | x | x | increase |
| hsa-miR-99b-5p | x | x | x | increase |
| hsa-miR-125b-5p | x | x | x | increase |
| hsa-miR-132-3p | x | x | x | increase |
| hsa-miR-224-5p | x | x | x | increase |
| hsa-miR-340-3p | x | x | x | increase |
| hsa-miR-342-5p | x | x | x | increase |
| hsa-miR-877-5p | x | x | x | increase |
| hsa-miR-944 | x | x | x | increase |
| hsa-miR-122-5p | x | x | x | increase |
| hsa-miR-133a-3p | x | x | x | increase |
| hsa-miR-151a-3p | x | x | x | increase |
| hsa-miR-151a-5p | x | x | x | increase |
| hsa-miR-151b | x | x | x | increase |
| hsa-miR-195-5p | x | x | x | increase |
| hsa-miR-23b-3p | x | x | x | increase |
| hsa-miR-34b-3p | x | x | x | increase |
| hsa-miR-34c-5p | x | x | x | increase |
| hsa-miR-361-5p | x | x | x | increase |
| hsa-miR-449c-5p | x | x | x | increase |
| hsa-miR-576-5p | x | x | x | increase |
| hsa-miR-98-5p | x | x | x | increase |
| hsa-miR-99a-5p | x | x | x | increase |
| hsa-miR-9-5p | x | x | | increase |
| hsa-miR-34c-3p | x | | | increase |
| hsa-miR-449b-5p | x | | | increase |
| hsa-miR-485-3p | x | | | increase |
| hsa-miR-106b-3p | x | x | x | decrease |
| hsa-miR-140-3p | x | x | x | decrease |
| hsa-miR-181c-3p | x | x | x | decrease |
| hsa-miR-181c-5p | x | x | x | decrease |
| hsa-miR-181d-5p | x | x | x | decrease |
| hsa-miR-186-5p | x | x | x | decrease |
| hsa-miR-199b-5p | x | x | x | decrease |
| hsa-miR-27a-5p | x | x | x | decrease |
| hsa-miR-30e-5p | x | x | x | decrease |
| hsa-miR-345-5p | x | x | x | decrease |
| hsa-miR-3615 | x | x | x | decrease |
| hsa-miR-93-3p | x | x | x | decrease |

TABLE 32

MicroRNA markers that are differentially expressed in plasma based on the samples from players diagnosed with a concussion

| | Concussion vs. | | | | |
|---|---|---|---|---|---|
| MicroRNA | Baseline | High_freq_hits | Low_freq_hits | Max_hitsp | Min_hitsp |
| hsa-let-7c-5p | −1.39 | −1.90 | −2.10 | −1.99 | −1.39 |
| hsa-let-7f-1-3p | 1.34 | | | | |
| hsa-let-7i-3p | | | −1.81 | | −2.30 |
| hsa-miR-100-5p | −2.24 | −2.55 | −2.94 | −3.13 | −2.87 |
| hsa-miR-106a-5p | −1.66 | −1.33 | −1.51 | −1.55 | −1.54 |
| hsa-miR-107 | −1.57 | −1.36 | −2.27 | −1.22 | −2.52 |
| hsa-miR-10b-5p | −2.36 | −2.41 | −2.38 | −2.09 | −2.43 |
| hsa-miR-1180-3p | −1.75 | | | −2.68 | |
| hsa-miR-1185-1-3p | 1.84 | 1.99 | 1.43 | 1.40 | 1.35 |
| hsa-miR-1224-5p | −2.98 | | −4.00 | −2.97 | −3.95 |
| hsa-miR-1228-3p | | | | −2.47 | |
| hsa-miR-1229-3p | 2.16 | 1.81 | 1.81 | 1.65 | 1.82 |
| hsa-miR-1246 | −3.20 | −3.27 | −2.99 | −4.23 | −2.14 |
| hsa-miR-1255b-5p | −1.83 | | −3.07 | −2.65 | −2.72 |
| hsa-miR-125b-1-3p | −1.91 | | −1.81 | −2.96 | |
| hsa-miR-125b-2-3p | −1.75 | −2.00 | −1.82 | −3.70 | −3.35 |
| hsa-miR-125b-5p | −2.10 | −2.01 | −2.86 | −3.42 | −3.05 |
| hsa-miR-1260a | 1.55 | 1.75 | 1.55 | 1.35 | 1.61 |
| hsa-miR-1260b | 1.46 | 1.57 | 1.45 | 1.31 | 1.54 |

TABLE 32-continued

MicroRNA markers that are differentially expressed in plasma based on the samples from players diagnosed with a concussion

| MicroRNA | Concussion vs. | | | | |
|---|---|---|---|---|---|
| | Baseline | High_freq_hits | Low_freq_hits | Max_hitsp | Min_hitsp |
| hsa-miR-1270 | −2.67 | −1.72 | −2.48 | −2.25 | −1.75 |
| hsa-miR-129-2-3p | | | −3.13 | | −3.83 |
| hsa-miR-1323 | −2.66 | | | −3.11 | |
| hsa-miR-133a-5p | | −2.40 | −3.12 | −2.68 | −2.60 |
| hsa-miR-135a-5p | | | | −2.76 | |
| hsa-miR-138-1-3p | | | −2.62 | | −2.96 |
| hsa-miR-138-5p | −2.42 | −2.86 | −3.43 | −3.43 | −4.46 |
| hsa-miR-144-3p | −2.56 | −1.98 | −2.01 | −1.27 | −1.73 |
| hsa-miR-144-5p | −2.36 | −1.65 | −1.52 | −1.28 | −1.37 |
| hsa-miR-145-3p | −1.89 | −1.77 | −1.91 | −1.82 | −1.65 |
| hsa-miR-145-5p | 1.69 | 1.63 | 1.25 | 1.10 | 1.23 |
| hsa-miR-149-5p | | | −2.24 | −3.25 | −2.40 |
| hsa-miR-150-3p | −1.72 | −2.02 | −1.92 | −3.02 | −2.76 |
| hsa-miR-15b-3p | −1.97 | −1.73 | −2.01 | −1.46 | −1.70 |
| hsa-miR-16-2-3p | −1.99 | −1.54 | −1.43 | | −1.40 |
| hsa-miR-184 | | | −2.62 | −2.49 | −2.42 |
| hsa-miR-185-5p | −1.12 | −1.50 | −1.54 | | −2.89 |
| hsa-miR-18b-3p | −2.01 | | | | |
| hsa-miR-192-5p | −1.89 | −1.73 | −1.65 | −1.42 | −1.91 |
| hsa-miR-193b-5p | | | −3.54 | −3.87 | |
| hsa-miR-195-3p | | −2.90 | | −1.96 | −2.23 |
| hsa-miR-19a-5p | | | −1.89 | | −2.19 |
| hsa-miR-203a-3p | −3.79 | −4.57 | −3.00 | −5.49 | −2.64 |
| hsa-miR-205-5p | −3.16 | −3.49 | −3.20 | −3.64 | −3.32 |
| hsa-miR-20b-3p | −2.70 | −2.21 | −2.69 | −2.40 | −2.75 |
| hsa-miR-212-5p | 2.71 | 1.85 | 1.76 | 1.98 | 3.09 |
| hsa-miR-214-3p | | | −2.72 | −2.92 | |
| hsa-miR-215-5p | −2.22 | −1.98 | −2.40 | −1.88 | −2.03 |
| hsa-miR-219a-2-3p | | | | −2.99 | |
| hsa-miR-22-5p | −1.29 | −1.74 | −1.78 | −1.19 | −1.92 |
| hsa-miR-25-3p | −1.60 | −1.72 | −1.42 | −1.11 | −1.36 |
| hsa-miR-25-5p | −1.63 | −2.26 | −2.20 | −2.37 | −2.35 |
| hsa-miR-30a-3p | −1.02 | −1.56 | −1.66 | −2.31 | −1.88 |
| hsa-miR-31-5p | −2.80 | −2.88 | −3.04 | −3.36 | −3.11 |
| hsa-miR-3127-5p | −2.94 | −2.74 | −2.43 | −3.22 | −2.47 |
| hsa-miR-3157-3p | | | −2.12 | | −2.72 |
| hsa-miR-3159 | | −2.34 | −2.37 | −2.51 | |
| hsa-miR-3163 | −3.39 | | | | |
| hsa-miR-3168 | | | −2.66 | −2.86 | |
| hsa-miR-3199 | | | −2.29 | | −2.84 |
| hsa-miR-320b | | −1.84 | −2.27 | −3.35 | |
| hsa-miR-320c | −1.70 | −2.12 | −2.65 | −2.92 | −2.50 |
| hsa-miR-320d | −2.66 | −3.08 | −3.34 | −3.63 | −2.94 |
| hsa-miR-320e | −2.20 | −2.82 | −2.86 | −3.28 | −2.51 |
| hsa-miR-331-3p | 2.12 | 1.82 | 1.96 | 1.21 | 1.57 |
| hsa-miR-338-5p | −1.53 | −1.60 | −1.46 | −1.88 | −1.43 |
| hsa-miR-342-5p | −1.79 | −2.45 | −2.03 | −2.57 | −1.84 |
| hsa-miR-34c-5p | −3.71 | −2.08 | | | |
| hsa-miR-362-3p | −3.29 | −2.53 | −2.93 | −2.70 | −3.16 |
| hsa-miR-363-3p | −1.68 | −1.57 | −1.34 | −1.34 | −1.30 |
| hsa-miR-365b-5p | | | −2.49 | −2.61 | |
| hsa-miR-3688-5p | −2.38 | −1.93 | −2.23 | −1.70 | −2.60 |
| hsa-miR-378a-3p | −1.79 | −1.79 | −3.03 | | |
| hsa-miR-378b | | −3.03 | | −2.89 | |
| hsa-miR-378d | −1.93 | | −2.19 | −3.03 | −2.15 |
| hsa-miR-378f | | −2.55 | −2.51 | −2.90 | −2.67 |
| hsa-miR-378g | | | −2.44 | −2.55 | |
| hsa-miR-423-5p | | | −2.45 | −1.75 | |
| hsa-miR-4466 | | | | −2.41 | |
| hsa-miR-4479 | | | −2.23 | | −2.73 |
| hsa-miR-449b-5p | −2.25 | | | | |
| hsa-miR-449c-5p | −3.12 | −2.26 | −3.28 | −3.01 | −4.40 |
| hsa-miR-451a | −2.19 | −1.63 | −1.67 | −1.25 | −1.78 |
| hsa-miR-4638-5p | 2.11 | 2.40 | 2.30 | 2.56 | 2.77 |
| hsa-miR-4726-5p | | | | −2.43 | |
| hsa-miR-4732-3p | −2.24 | −2.99 | −2.06 | −3.31 | −2.01 |
| hsa-miR-4732-5p | −2.56 | −2.03 | −2.08 | −2.57 | |
| hsa-miR-4745-3p | | −2.90 | | | |
| hsa-miR-4745-5p | | | −2.83 | −3.26 | −2.50 |
| hsa-miR-4766-3p | −2.41 | −2.34 | −2.33 | −2.47 | −2.50 |
| hsa-miR-4772-3p | −3.20 | | −2.39 | | |
| hsa-miR-483-3p | −4.38 | −2.92 | −2.80 | −4.90 | |
| hsa-miR-486-3p | −2.50 | −2.61 | −2.29 | −2.38 | −2.36 |

TABLE 32-continued

MicroRNA markers that are differentially expressed in plasma based on the samples from players diagnosed with a concussion

| MicroRNA | Concussion vs. | | | | |
|---|---|---|---|---|---|
| | Baseline | High_freq_hits | Low_freq_hits | Max_hitsp | Min_hitsp |
| hsa-miR-486-5p | −2.06 | −2.14 | −2.16 | −2.22 | −2.06 |
| hsa-miR-497-5p | −1.04 | −1.17 | −1.50 | −1.74 | −1.73 |
| hsa-miR-5001-3p | | | −2.01 | | −2.62 |
| hsa-miR-501-3p | | | −2.26 | | −2.50 |
| hsa-miR-5010-5p | | −1.58 | −1.98 | −2.29 | |
| hsa-miR-502-3p | −1.32 | −1.20 | −1.42 | −1.55 | −1.82 |
| hsa-miR-5100 | | | | −2.74 | |
| hsa-miR-512-3p | −3.32 | −2.21 | | −4.47 | |
| hsa-miR-515-3p | | −2.34 | | −3.39 | |
| hsa-miR-516b-5p | | | | −3.18 | |
| hsa-miR-532-5p | −1.17 | −1.35 | −1.18 | −1.31 | −1.49 |
| hsa-miR-570-3p | | | −2.28 | | −2.51 |
| hsa-miR-579-5p | | | −2.22 | | −2.85 |
| hsa-miR-582-3p | −1.83 | −1.42 | −1.37 | | −1.47 |
| hsa-miR-590-5p | | −2.43 | −2.41 | −2.61 | −2.94 |
| hsa-miR-615-3p | | | | | |
| hsa-miR-636 | | −2.27 | −2.24 | −3.38 | −2.24 |
| hsa-miR-6509-3p | | 2.53 | | 2.57 | |
| hsa-miR-660-5p | −1.37 | −1.12 | −1.22 | −1.03 | −1.20 |
| hsa-miR-6791-3p | 1.86 | 1.39 | 1.71 | 1.29 | 1.41 |
| hsa-miR-6832-5p | | | −2.27 | −2.84 | |
| hsa-miR-6850-5p | | | −2.86 | −3.24 | |
| hsa-miR-6858-5p | | | | −2.67 | |
| hsa-miR-758-5p | 2.17 | 2.23 | 2.06 | 2.01 | 1.96 |
| hsa-miR-7975 | | −3.12 | | −3.35 | |
| hsa-miR-7976 | | | −3.00 | | −2.14 |
| hsa-miR-8061 | | | −3.00 | | |
| hsa-miR-8072 | | | | −2.52 | |
| hsa-miR-873-3p | −2.15 | −2.95 | −3.51 | −5.05 | −3.39 |
| hsa-miR-873-5p | −4.10 | −3.79 | −3.69 | −5.44 | −3.72 |
| hsa-miR-887-3p | −2.49 | | −3.42 | −3.09 | −3.54 |
| hsa-miR-92a-1-5p | −1.27 | −1.98 | −1.52 | −2.23 | −1.82 |
| hsa-miR-96-5p | −2.12 | −2.20 | −1.71 | −2.06 | −1.77 |
| hsa-miR-99a-5p | −1.92 | −1.96 | −2.23 | −2.91 | −2.20 |

TABLE 33

MicroRNA markers that are differentially expressed in urine based on the samples from players diagnosed with a concussion

| MicroRNA | Concussion vs. | | | | |
|---|---|---|---|---|---|
| | Baseline | High_freq_hits | Low_freq_hits | Max_hitsp | Min_hitsp |
| hsa-miR-106b-5p | −2.48 | −3.39 | −2.70 | −3.17 | −2.24 |
| hsa-miR-1226-3p | | | 4.42 | | 5.07 |
| hsa-miR-1246 | −1.84 | | −2.54 | | |
| hsa-miR-127-3p | | −2.88 | | | |
| hsa-miR-1275 | −2.85 | −2.93 | | | |
| hsa-miR-143-3p | −2.15 | | | | |
| hsa-miR-146b-5p | 1.76 | | 2.27 | 1.99 | 2.80 |
| hsa-miR-148b-5p | −2.48 | | | | |
| hsa-miR-15b-5p | −2.85 | −3.23 | −3.26 | −2.61 | −3.23 |
| hsa-miR-181c-5p | −1.30 | −2.45 | −1.61 | | −1.51 |
| hsa-miR-184 | 2.12 | 3.50 | 2.64 | 2.54 | 2.83 |
| hsa-miR-185-3p | | | | 2.74 | |
| hsa-miR-190a-5p | −2.48 | −3.04 | | | |
| hsa-miR-203a-3p | | | | −3.46 | |
| hsa-miR-203b-5p | −2.77 | | | | |
| hsa-miR-204-3p | | | 2.30 | | |
| hsa-miR-205-5p | −2.86 | −3.33 | −3.48 | −2.47 | −3.57 |
| hsa-miR-210-3p | −1.97 | −2.20 | | | |
| hsa-miR-25-5p | −2.50 | | | | |
| hsa-miR-296-3p | −2.21 | | | | |
| hsa-miR-29b-3p | −2.49 | −2.95 | −2.57 | −2.80 | −2.33 |
| hsa-miR-320a | −2.21 | | | | |
| hsa-miR-320b | −2.26 | −2.40 | | −2.53 | |
| hsa-miR-320c | −2.33 | | | | |
| hsa-miR-339-5p | | | | 3.88 | |

TABLE 33-continued

MicroRNA markers that are differentially expressed in urine based on the samples from players diagnosed with a concussion

| MicroRNA | Concussion vs. | | | | |
|---|---|---|---|---|---|
| | Baseline | High_freq_hits | Low_freq_hits | Max_hitsp | Min_hitsp |
| hsa-miR-33b-5p | | −2.91 | | | |
| hsa-miR-378a-3p | | | 1.82 | | |
| hsa-miR-378c | | | 2.32 | | |
| hsa-miR-378f | | | 2.59 | 2.76 | 2.35 |
| hsa-miR-4461 | −4.08 | | | | |
| hsa-miR-4507 | −2.05 | | | | |
| hsa-miR-4510 | | | | 2.48 | |
| hsa-miR-455-5p | | | | −2.16 | |
| hsa-miR-485-5p | −1.98 | | | | |
| hsa-miR-486-3p | −2.38 | | | | |
| hsa-miR-486-5p | −2.70 | | | | |
| hsa-miR-574-3p | | | | 1.99 | |
| hsa-miR-615-3p | | 2.05 | | | |
| hsa-miR-664a-5p | −2.77 | | | | |
| hsa-miR-671-5p | | | 2.49 | | |
| hsa-miR-6723-5p | −2.40 | | | | |
| hsa-miR-6852-5p | −2.20 | | | | |
| hsa-miR-769-5p | | −2.44 | | | |
| hsa-miR-8061 | −2.69 | | | | |
| hsa-miR-892a | | | −2.54 | | |

TABLE 34

MicroRNA markers differentially expressed in plasma based on the frequency of hits or the impact score

| | High_freq_hits vs. | | Low_freq_hits vs. | Max_hitsp vs. | | Min_hitsp vs. |
|---|---|---|---|---|---|---|
| MicroRNA | Baseline | Low_freq_hits | Baseline | Baseline | Min_hitsp | Baseline |
| hsa-let-7f-1-3p | | | 1.09 | 1.52 | | |
| hsa-let-7i-3p | | | 1.10 | | −1.22 | 1.60 |
| hsa-miR-106a-3p | −1.67 | −2.02 | | | −2.23 | |
| hsa-miR-107 | | | | | −1.30 | 1.07 |
| hsa-miR-1180-3p | | | | 1.06 | 2.23 | −1.17 |
| hsa-miR-1224-5p | | −2.15 | | | | |
| hsa-miR-1228-3p | | 2.02 | −1.66 | | 2.94 | −2.67 |
| hsa-miR-1246 | | | | 1.61 | 2.09 | |
| hsa-miR-1255b-5p | | −1.34 | 1.23 | 1.08 | | 1.16 |
| hsa-miR-125b-1-3p | | | | 1.20 | | |
| hsa-miR-125b-5p | | | | 1.28 | | |
| hsa-miR-129-2-3p | | −3.01 | 2.08 | | −2.47 | 2.77 |
| hsa-miR-1291 | 1.77 | | | | | 1.91 |
| hsa-miR-1323 | −1.78 | | −1.58 | | 2.55 | |
| hsa-miR-133a-5p | | | 1.17 | | | |
| hsa-miR-135a-5p | 1.10 | | | 3.12 | 1.54 | 1.58 |
| hsa-miR-138-1-3p | | −3.40 | 2.47 | | −3.13 | 2.97 |
| hsa-miR-138-5p | | | 1.01 | | | 1.64 |
| hsa-miR-144-3p | | | | −1.05 | | |
| hsa-miR-149-5p | | | | 1.63 | | |
| hsa-miR-184 | | −2.01 | 1.79 | 1.73 | | 1.65 |
| hsa-miR-185-5p | | | | | −2.32 | 2.06 |
| hsa-miR-18b-3p | −1.71 | | | −1.49 | | −1.32 |
| hsa-miR-193b-5p | | −1.69 | 1.94 | 1.52 | 2.20 | |
| hsa-miR-195-3p | 2.32 | 1.64 | | 1.05 | | 1.31 |
| hsa-miR-19a-5p | | −1.21 | 1.52 | | −1.56 | 1.95 |
| hsa-miR-203a-3p | | 1.57 | | 1.56 | 2.85 | −1.29 |
| hsa-miR-212-5p | | | | 1.22 | 1.12 | |
| hsa-miR-214-3p | | −1.75 | 2.09 | 2.53 | 1.89 | |
| hsa-miR-218-5p | −1.81 | −2.53 | | | | |
| hsa-miR-219a-2-3p | | | −2.24 | | 4.11 | |
| hsa-miR-3157-3p | | −1.54 | | | −2.09 | 1.36 |
| hsa-miR-3159 | | | 1.00 | 1.08 | | |
| hsa-miR-3163 | −1.61 | | −1.83 | −1.34 | | −1.78 |
| hsa-miR-3168 | 2.05 | | 3.26 | 3.68 | | 3.23 |
| hsa-miR-3199 | | −1.98 | 1.51 | | −2.96 | 1.94 |
| hsa-miR-320b | | | 1.35 | | 2.25 | 1.55 |
| hsa-miR-320e | | | | 1.11 | | |
| hsa-miR-34c-5p | −1.64 | | −2.28 | | | |
| hsa-miR-365b-5p | −2.13 | −3.25 | | | 3.09 | |
| hsa-miR-378a-3p | | −1.25 | 1.24 | | | |

TABLE 34-continued

MicroRNA markers differentially expressed in plasma based on the frequency of hits or the impact score

| MicroRNA | High_freq_hits vs. Baseline | High_freq_hits vs. Low_freq_hits | Low_freq_hits vs. Baseline | Max_hitsp vs. Baseline | Max_hitsp vs. Min_hitsp | Min_hitsp vs. Baseline |
|---|---|---|---|---|---|---|
| hsa-miR-378b | 2.33 | | 1.38 | 1.66 | | |
| hsa-miR-378d | | | 1.21 | | | |
| hsa-miR-378f | 1.36 | | 1.32 | 1.53 | | 1.30 |
| hsa-miR-378g | 1.23 | | 1.69 | 1.28 | 2.03 | |
| hsa-miR-423-5p | | −1.03 | 1.14 | 1.07 | 1.07 | |
| hsa-miR-4436b-3p | | 1.65 | | | 2.22 | |
| hsa-miR-4466 | | | | | 2.22 | |
| hsa-miR-4479 | | −1.30 | 1.03 | | | 1.56 |
| hsa-miR-449b-5p | −2.48 | | −1.83 | | | |
| hsa-miR-449c-5p | | | | | −1.39 | |
| hsa-miR-4726-5p | | | | 3.22 | | |
| hsa-miR-4732-3p | | | | 1.03 | 1.31 | |
| hsa-miR-4732-5p | | | | | 1.28 | −1.10 |
| hsa-miR-4745-3p | 1.97 | 2.73 | | | | |
| hsa-miR-4745-5p | | −1.72 | 2.50 | 2.84 | | 2.08 |
| hsa-miR-4772-3p | −1.59 | | | −2.13 | | |
| hsa-miR-483-3p | −1.46 | | −1.58 | | 2.78 | −2.09 |
| hsa-miR-5001-3p | | | 1.17 | | −1.54 | 1.74 |
| hsa-miR-501-3p | | −1.07 | 1.06 | | | 1.21 |
| hsa-miR-5010-5p | | | | 1.09 | 1.08 | |
| hsa-miR-5100 | | | | 2.09 | 2.08 | |
| hsa-miR-512-3p | | | −1.88 | 2.09 | 4.42 | −2.33 |
| hsa-miR-515-3p | 2.85 | 2.35 | | 3.99 | 3.83 | |
| hsa-miR-516b-5p | | | | 2.05 | 3.28 | |
| hsa-miR-570-3p | −2.34 | −2.92 | | | −2.38 | |
| hsa-miR-579-5p | | −1.60 | 1.73 | | −2.49 | 2.18 |
| hsa-miR-582-3p | | | | −1.06 | −1.03 | |
| hsa-miR-590-5p | 1.44 | | 1.42 | 1.26 | | 1.60 |
| hsa-miR-615-3p | | | | | −2.28 | 1.46 |
| hsa-miR-636 | 1.05 | | 1.02 | 2.14 | | |
| hsa-miR-6509-3p | −2.01 | −2.35 | | −2.07 | −2.95 | |
| hsa-miR-6850-5p | −2.11 | −3.26 | | | 3.59 | −2.16 |
| hsa-miR-6858-5p | | | | 2.07 | | |
| hsa-miR-7975 | 2.18 | 1.57 | | 2.73 | | |
| hsa-miR-7976 | | −2.32 | 1.65 | | −1.21 | |
| hsa-miR-8061 | | −1.73 | 1.57 | | | |
| hsa-miR-8072 | | | | 2.23 | | |
| hsa-miR-873-3p | | | 1.36 | 2.08 | 1.66 | |
| hsa-miR-873-5p | | | | 1.60 | 1.73 | |
| hsa-miR-887-3p | | −2.09 | | | | 1.80 |

TABLE 35

MicroRNA markers differentially expressed in plasma based on the frequency of hits or the impact score

| MicroRNA | High_freq_hits vs. Baseline | High_freq_hits vs. Low_freq_hits | Low_freq_hits vs. Baseline | Max_hitsp vs. Baseline | Max_hitsp vs. Min_hitsp | Min_hitsp vs. Baseline |
|---|---|---|---|---|---|---|
| hsa-miR-100-5p | | | | | | −1.17 |
| hsa-miR-107 | | 1.07 | | | | |
| hsa-miR-10b-5p | | | | | | −1.08 |
| hsa-miR-122-3p | | | | | 1.14 | |
| hsa-miR-1246 | | | | | −1.16 | |
| hsa-miR-1247-3p | 1.27 | 1.15 | | | | |
| hsa-miR-1247-5p | | | −1.05 | | | |
| hsa-miR-1256 | −1.01 | −1.04 | | | | |
| hsa-miR-125b-1-3p | | | | −1.03 | | −1.22 |
| hsa-miR-125b-5p | | | | | | −1.03 |
| hsa-miR-129-2-3p | | | | | 1.67 | |
| hsa-miR-129-5p | | | | | | −1.11 |
| hsa-miR-1291 | | | | 1.21 | 1.11 | |
| hsa-miR-1294 | | | −1.10 | | 1.16 | |
| hsa-miR-1297 | | | | −1.22 | | |
| hsa-miR-1323 | | | | | | −1.08 |
| hsa-miR-150-3p | | | | | | −1.15 |
| hsa-miR-16-2-3p | | | −1.25 | | | |
| hsa-miR-186-3p | | | | | −1.13 | |
| hsa-miR-18b-3p | | 1.08 | | | | −1.41 |
| hsa-miR-1910-5p | | | | | 1.14 | |
| hsa-miR-193a-3p | | 1.05 | | | | |

TABLE 35-continued

MicroRNA markers differentially expressed in plasma based on the frequency of hits or the impact score

| MicroRNA | High_freq_hits vs. Baseline | Low_freq_hits | Low_freq_hits vs. Baseline | Max_hitsp vs. Baseline | Min_hitsp | Min_hitsp vs. Baseline |
|---|---|---|---|---|---|---|
| hsa-miR-196a-5p | | | | | | −1.41 |
| hsa-miR-202-3p | | | | | | −1.36 |
| hsa-miR-204-5p | −1.15 | | | | | |
| hsa-miR-210-3p | | | −1.04 | | | |
| hsa-miR-2110 | | | | | 1.15 | |
| hsa-miR-2115-3p | | 1.59 | | | | |
| hsa-miR-214-3p | | | −1.01 | | | |
| hsa-miR-219b-5p | | | −1.03 | | | |
| hsa-miR-23b-5p | | | | 1.18 | | |
| hsa-miR-296-5p | | 1.01 | | | | |
| hsa-miR-3140-3p | | | | −1.26 | | |
| hsa-miR-3146 | | −1.19 | 1.14 | | | |
| hsa-miR-3175 | −1.26 | | −1.15 | | | |
| hsa-miR-3180 | | | | −1.08 | | −1.48 |
| hsa-miR-3180-3p | | | | −1.05 | | −1.50 |
| hsa-miR-3180-5p | | | | | 1.10 | |
| hsa-miR-3184-5p | | | | −1.10 | | |
| hsa-miR-320b | | | | | | −1.33 |
| hsa-miR-320c | | | | | | −1.10 |
| hsa-miR-320e | | | | | | −1.08 |
| hsa-miR-3591-3p | | | | | 1.29 | |
| hsa-miR-3617-5p | | | | | −1.39 | 1.08 |
| hsa-miR-3622b-3p | | | | | | −1.14 |
| hsa-miR-3688-3p | | 1.03 | | | | |
| hsa-miR-371a-3p | | | | | | −1.08 |
| hsa-miR-371b-5p | | | | | | −1.03 |
| hsa-miR-378a-3p | | | −1.11 | | | |
| hsa-miR-378b | | 1.09 | | | 1.17 | −1.78 |
| hsa-miR-378c | | | −1.18 | | | |
| hsa-miR-378f | | | | | 1.30 | −1.03 |
| hsa-miR-378g | | 1.13 | | −1.18 | | −1.65 |
| hsa-miR-3942-3p | | | −1.06 | | | |
| hsa-miR-423-5p | | | | | | −1.11 |
| hsa-miR-4421 | | 1.04 | | | | |
| hsa-miR-4422 | | | | | −1.65 | |
| hsa-miR-4448 | | | | 1.84 | 1.12 | |
| hsa-miR-4467 | 1.74 | | 1.02 | | | |
| hsa-miR-4477b | | | | | | 1.11 |
| hsa-miR-4479 | | | −1.03 | | | |
| hsa-miR-4510 | | | 1.02 | | | −1.17 |
| hsa-miR-455-5p | | | | | | −1.24 |
| hsa-miR-4635 | | | | | | −1.10 |
| hsa-miR-4642 | | | | 1.09 | | |
| hsa-miR-4647 | | | | | | −1.19 |
| hsa-miR-4657 | | 1.08 | −1.09 | | | |
| hsa-miR-4659a-3p | | | | −1.27 | −1.24 | |
| hsa-miR-4665-5p | | | −1.10 | | | |
| hsa-miR-4685-3p | | | −1.08 | | | |
| hsa-miR-4690-3p | | | | | −1.15 | |
| hsa-miR-4732-3p | | 1.02 | | | | |
| hsa-miR-4745-5p | | | | | 1.30 | |
| hsa-miR-4772-3p | | | | −1.17 | | |
| hsa-miR-483-3p | | | | −1.14 | | |
| hsa-miR-483-5p | | | | | 1.30 | −1.30 |
| hsa-miR-486-5p | | | | | | −1.10 |
| hsa-miR-490-3p | | | | | 1.05 | −1.14 |
| hsa-miR-490-5p | | | | | 1.44 | |
| hsa-miR-5001-3p | | | | 1.11 | 1.37 | |
| hsa-miR-5004-3p | | | | 1.30 | 1.28 | |
| hsa-miR-500b-3p | | −1.39 | 1.33 | | | |
| hsa-miR-501-3p | | | −1.10 | | 1.42 | −1.22 |
| hsa-miR-512-3p | 1.06 | 1.31 | | | | |
| hsa-miR-516a-5p | | 1.14 | | | | −1.43 |
| hsa-miR-516b-5p | | 1.24 | | | | −1.59 |
| hsa-miR-517a-3p = hsa-miR-517b-3p | | 1.36 | | −1.29 | | −1.27 |
| hsa-miR-518b | | | | | | −1.03 |
| hsa-miR-5190 | | | | −1.02 | | |
| hsa-miR-548aq-5p | 1.23 | | | | | |
| hsa-miR-548f-5p | | | | | −1.10 | |
| hsa-miR-550b-3p | | −1.07 | | | | |
| hsa-miR-5588-5p | | | | | −1.07 | |
| hsa-miR-561-5p | | | | −1.01 | | |
| hsa-miR-570-3p | | | | | | −1.37 |
| hsa-miR-579-5p | −1.12 | | −1.21 | | | |

TABLE 35-continued

MicroRNA markers differentially expressed in plasma based on the frequency of hits or the impact score

| MicroRNA | High_freq_hits vs. Baseline | High_freq_hits vs. Low_freq_hits | Low_freq_hits vs. Baseline | Max_hitsp vs. Baseline | Max_hitsp vs. Min_hitsp | Min_hitsp vs. Baseline |
|---|---|---|---|---|---|---|
| hsa-miR-582-5p | | | | | | −1.03 |
| hsa-miR-597-3p | | 1.02 | | | | |
| hsa-miR-6130 | | | | | | −1.13 |
| hsa-miR-624-3p | | | | | | −1.25 |
| hsa-miR-642a-3p | | | | −1.11 | | −1.13 |
| hsa-miR-642b-5p | | | | −1.21 | | −1.15 |
| hsa-miR-6509-3p | | | | | 1.24 | |
| hsa-miR-6515-5p | | | | | 1.26 | |
| hsa-miR-6727-5p | | | | | | −1.14 |
| hsa-miR-6740-5p | | | | | 1.31 | −1.19 |
| hsa-miR-6751-3p | | −1.02 | | | | |
| hsa-miR-6754-3p | | | | | | −1.11 |
| hsa-miR-6767-5p | | 1.33 | −1.23 | | | |
| hsa-miR-6780a-5p | | | | | 1.87 | −1.36 |
| hsa-miR-6781-5p | | | | 1.58 | 1.39 | |
| hsa-miR-6782-3p | | | | −1.36 | | −1.24 |
| hsa-miR-6783-3p | | −1.01 | | | | |
| hsa-miR-6791-5p | | | | | | −1.09 |
| hsa-miR-6797-3p | | | 1.16 | | | |
| hsa-miR-6804-5p | | 1.09 | | | | |
| hsa-miR-6829-5p | −1.01 | | | | | |
| hsa-miR-6832-5p | | | | | | −1.17 |
| hsa-miR-6850-5p | 1.17 | | | | | |
| hsa-miR-6876-5p | −1.18 | | | | | |
| hsa-miR-6885-3p | −1.02 | −1.30 | | | | |
| hsa-miR-7113-5p | | | | | 1.25 | |
| hsa-miR-7703 | | | | | | −1.07 |
| hsa-miR-7706 | | | | | 1.56 | −1.02 |
| hsa-miR-7851-3p | −1.21 | −1.13 | | | | |
| hsa-miR-7852-3p | −1.21 | | | | | |
| hsa-miR-7975 | | | −1.33 | | | |
| hsa-miR-8061 | | | | | 1.09 | −1.21 |
| hsa-miR-873-3p | | | | −1.07 | | −1.99 |
| hsa-miR-873-5p | 1.06 | 1.32 | | | | |
| hsa-miR-874-3p | | | | | 1.05 | |
| hsa-miR-885-5p | | | | | 1.11 | −1.04 |
| hsa-miR-887-3p | | | | −1.06 | | −1.20 |
| hsa-miR-9-3p | | | | | 1.14 | −1.15 |
| hsa-miR-935 | | | | | 1.09 | |
| hsa-miR-939-3p | | | | | 1.10 | |
| hsa-miR-939-5p | | | | | 1.15 | |

TABLE 36

MicroRNA markers differentially expressed in urine based on the frequency of hits or the impact score

| MicroRNA | High_freq_hits vs. Baseline | High_freq_hits vs. Low_freq_hits | Low_freq_hits vs. Baseline | Max_hitsp vs. Baseline | Max_hitsp vs. Min_hitsp | Min_hitsp vs. Baseline |
|---|---|---|---|---|---|---|
| hsa-miR-122-5p | −2.96 | | −2.55 | | | −2.34 |
| hsa-miR-1226-3p | | 2.48 | −3.91 | | 3.43 | −4.72 |
| hsa-miR-1246 | −1.68 | −1.10 | | | | |
| hsa-miR-125a-3p | −2.25 | | −2.71 | −1.95 | | −2.50 |
| hsa-miR-125b-1-3p | 2.67 | 2.97 | | | | |
| hsa-miR-126-5p | | | −2.19 | −1.76 | | −2.00 |
| hsa-miR-127-3p | 1.42 | 4.89 | −3.46 | −2.05 | | −1.98 |
| hsa-miR-1275 | | 3.08 | −2.25 | −1.99 | | −1.99 |
| hsa-miR-1307-3p | | 1.33 | −2.06 | −1.89 | | −1.85 |
| hsa-miR-143-3p | | | −2.12 | −1.56 | | −2.08 |
| hsa-miR-146a-5p | | 1.66 | −2.08 | −1.44 | | −1.94 |
| hsa-miR-146b-5p | | 1.54 | | | | −1.05 |
| hsa-miR-148b-5p | | | −1.14 | | | −1.10 |
| hsa-miR-181c-5p | 1.12 | | | | | |
| hsa-miR-184 | −1.63 | | | | | |
| hsa-miR-185-3p | | 2.40 | −1.08 | −2.87 | | −1.11 |
| hsa-miR-187-3p | | | −1.28 | | | −1.26 |
| hsa-miR-190a-5p | | 1.90 | | | | |
| hsa-miR-1910-5p | −2.06 | | −1.58 | −1.88 | | −1.38 |
| hsa-miR-199a-3p = hsa-miR-199b-3p | −1.87 | | −2.16 | −1.93 | | −2.08 |
| hsa-miR-203a-3p | −2.12 | | −1.73 | 1.89 | 3.49 | −1.59 |

TABLE 36-continued

MicroRNA markers differentially expressed in urine based on the frequency of hits or the impact score

| MicroRNA | High_freq_hits vs. Baseline | Low_freq_hits | Low_freq_hits vs. Baseline | Max_hitsp vs. Baseline | Min_hitsp | Min_hitsp vs. Baseline |
|---|---|---|---|---|---|---|
| hsa-miR-203b-5p | −3.57 | | −4.31 | −3.48 | | −3.94 |
| hsa-miR-204-3p | | 3.82 | −2.88 | −2.36 | | −2.58 |
| hsa-miR-205-5p | | | | | −1.10 | |
| hsa-miR-210-3p | | 2.43 | −2.10 | −2.30 | | −1.89 |
| hsa-miR-210-5p | | 2.06 | −1.24 | −1.74 | | |
| hsa-miR-212-3p | −3.49 | | −2.84 | −2.63 | | −3.04 |
| hsa-miR-221-3p | | | −1.16 | −1.01 | | −1.02 |
| hsa-miR-25-5p | −1.91 | | −2.04 | −2.53 | | −2.12 |
| hsa-miR-296-3p | | | −1.97 | −2.23 | | −1.97 |
| hsa-miR-3168 | −3.39 | | −2.83 | | | −1.78 |
| hsa-miR-3184-3p | −2.35 | | −2.90 | | | −2.74 |
| hsa-miR-320a | | 2.28 | −2.72 | −1.30 | 1.13 | −2.43 |
| hsa-miR-320b | | 2.90 | −2.78 | | 2.93 | −2.65 |
| hsa-miR-320c | −1.25 | 1.14 | −2.39 | −1.32 | | −2.11 |
| hsa-miR-328-3p | | 1.27 | −1.53 | −1.83 | | −1.50 |
| hsa-miR-331-3p | | | −1.15 | | | −1.10 |
| hsa-miR-339-5p | | 2.06 | | −3.62 | −3.00 | |
| hsa-miR-33b-5p | 2.23 | 2.01 | | | | |
| hsa-miR-378a-3p | | 3.09 | −2.49 | −1.89 | | −2.19 |
| hsa-miR-378c | 1.52 | 3.82 | −2.30 | −2.18 | | −1.95 |
| hsa-miR-378e | | 2.38 | −1.92 | | | −1.28 |
| hsa-miR-378f | | | −2.48 | −2.45 | | −2.04 |
| hsa-miR-423-5p | | 1.51 | −2.15 | −2.13 | | −1.98 |
| hsa-miR-4443 | −2.97 | | −3.08 | −3.45 | | −2.77 |
| hsa-miR-4461 | −3.33 | | −3.37 | −3.59 | | −3.29 |
| hsa-miR-4488 | | | −1.82 | | | −1.95 |
| hsa-miR-4507 | −3.02 | | −3.41 | −2.51 | | −2.99 |
| hsa-miR-4510 | | | 1.42 | | −2.06 | 1.58 |
| hsa-miR-451a | −1.64 | 1.33 | −2.97 | −2.45 | | −2.65 |
| hsa-miR-455-5p | 1.21 | 1.94 | | 1.64 | 2.18 | |
| hsa-miR-485-5p | | | −3.34 | | | −3.21 |
| hsa-miR-486-3p | −2.22 | | −2.65 | −2.33 | | −2.78 |
| hsa-miR-486-5p | −2.42 | | −3.23 | −3.15 | | −3.12 |
| hsa-miR-500a-3p | −1.49 | | −1.44 | −1.66 | | −1.48 |
| hsa-miR-501-5p | −3.39 | | −3.70 | −3.27 | | −3.65 |
| hsa-miR-5100 | −1.36 | | | | | −1.42 |
| hsa-miR-532-3p | −1.83 | | −1.09 | −1.67 | | −1.09 |
| hsa-miR-574-3p | | | | −1.45 | −1.19 | |
| hsa-miR-615-3p | −1.82 | | −1.48 | −1.36 | | −1.63 |
| hsa-miR-664a-5p | −1.35 | | −1.89 | −2.07 | | −1.43 |
| hsa-miR-671-5p | | 2.83 | −1.47 | | | |
| hsa-miR-6723-5p | −2.30 | | −2.29 | | | −2.72 |
| hsa-miR-6852-5p | | | −2.35 | −3.00 | | −1.89 |
| hsa-miR-6858-5p | | | −1.99 | | | −2.03 |
| hsa-miR-708-5p | −3.24 | −1.95 | −1.29 | | | −1.38 |
| hsa-miR-7160-5p | −2.72 | | −2.97 | −2.43 | | −2.35 |
| hsa-miR-769-5p | 1.87 | 3.90 | −2.03 | −2.21 | | −1.88 |
| hsa-miR-8061 | −3.23 | | −2.82 | −2.52 | | −2.53 |
| hsa-miR-874-3p | | 1.78 | −2.02 | −2.30 | | −2.01 |
| hsa-miR-874-5p | −2.18 | | −2.25 | −2.43 | | −2.45 |
| hsa-miR-888-5p | | | 1.47 | | | 1.31 |
| hsa-miR-892a | | | 2.93 | | | 2.45 |

TABLE 37

MicroRNA markers differentially expressed in urine based on the frequency of hits or the impact score

| MicroRNA | High_freq_hits vs. Baseline | Low_freq_hits | Low_freq_hits vs. Baseline | Max_hitsp vs. Baseline | Min_hitsp vs. Baseline | Low_freq_hits |
|---|---|---|---|---|---|---|
| hsa-let-7i-3p | | | | | −1.61 | 2.01 |
| hsa-miR-122-5p | | | | | −1.87 | 1.75 |
| hsa-miR-1226-5p | | | | −1.43 | | |
| hsa-miR-124-3p | | | | | −1.32 | 1.45 |
| hsa-miR-125b-1-3p | | | 1.38 | | | |
| hsa-miR-126-3p | | | 1.14 | | −1.10 | 1.48 |
| hsa-miR-1266-5p | | | | | 1.27 | |
| hsa-miR-129-1-3p | | | | | 1.17 | |
| hsa-miR-1298-5p | 1.66 | | 1.33 | | | |
| hsa-miR-1306-3p | | | | | | −1.24 |

TABLE 37-continued

MicroRNA markers differentially expressed in urine based on the frequency of hits or the impact score

| MicroRNA | High_freq_hits vs. Baseline | High_freq_hits vs. Low_freq_hits | Low_freq_hits vs. Baseline | Max_hitsp vs. Baseline | Min_hitsp vs. Baseline | Min_hitsp vs. Low_freq_hits |
|---|---|---|---|---|---|---|
| hsa-miR-1307-3p | | | | 1.33 | 1.72 | |
| hsa-miR-1307-5p | | | | 1.11 | | |
| hsa-miR-130b-3p | | | −1.41 | | | |
| hsa-miR-144-3p | | | 1.34 | | | |
| hsa-miR-146b-3p | | −1.25 | | 1.37 | 1.34 | |
| hsa-miR-148b-5p | 1.30 | | 1.20 | 1.78 | | |
| hsa-miR-149-5p | | 1.10 | | | 1.43 | |
| hsa-miR-155-5p | 1.16 | | | | | |
| hsa-miR-184 | | | | | −1.01 | |
| hsa-miR-187-3p | | | | 1.09 | | |
| hsa-miR-190a-5p | | | | | 1.15 | |
| hsa-miR-190b | | | −1.61 | | | |
| hsa-miR-191-3p | | | 1.19 | | | |
| hsa-miR-194-3p | 1.36 | | | | | |
| hsa-miR-199a-3p = hsa-miR-199b-3p | | | | −1.22 | −1.44 | |
| hsa-miR-199b-5p | | | | | | −1.55 |
| hsa-miR-200c-3p | 1.16 | | | 1.14 | | |
| hsa-miR-203a-3p | | | | 1.91 | 2.21 | |
| hsa-miR-210-3p | | | | 1.14 | 1.38 | |
| hsa-miR-210-5p | | | | | 1.21 | |
| hsa-miR-211-5p | | | | 1.10 | | |
| hsa-miR-222-5p | 1.38 | | | | | |
| hsa-miR-223-5p | | | | | | −1.74 |
| hsa-miR-224-5p | | | | | | 1.08 |
| hsa-miR-23b-5p | | | | | 1.22 | |
| hsa-miR-301b-3p | | | 1.46 | | | |
| hsa-miR-3168 | | | 1.28 | | | |
| hsa-miR-3182 | | | | 1.12 | 1.09 | |
| hsa-miR-3184-3p | | | | | −1.30 | |
| hsa-miR-3184-5p | | | | | | −1.10 |
| hsa-miR-320b | | | | 1.03 | 1.18 | |
| hsa-miR-320e | | | | | 1.25 | |
| hsa-miR-324-3p | | | | | 1.12 | |
| hsa-miR-338-5p | | | | | | 1.26 |
| hsa-miR-33b-5p | | | 1.13 | | | |
| hsa-miR-362-3p | | | | | | 1.27 |
| hsa-miR-374a-5p | | | | 1.11 | | 1.34 |
| hsa-miR-378a-3p | | | | 1.20 | 1.13 | |
| hsa-miR-378c | | | | 1.21 | 1.00 | |
| hsa-miR-3913-3p | | | −1.83 | | | |
| hsa-miR-3913-5p | | | −1.92 | | | |
| hsa-miR-3943 | | 1.29 | | | | |
| hsa-miR-425-3p | | | | | | 1.39 |
| hsa-miR-4326 | | | | 1.91 | | |
| hsa-miR-4443 | | | | | 1.38 | |
| hsa-miR-4448 | | | | −1.24 | −1.70 | |
| hsa-miR-4449 | | | 1.38 | | | |
| hsa-miR-4461 | | −1.30 | 1.32 | | | |
| hsa-miR-4466 | | | | 1.57 | 1.31 | |
| hsa-miR-450a-5p | −1.07 | −1.09 | | | | |
| hsa-miR-451a | 1.33 | | 2.21 | | | |
| hsa-miR-452-5p | −1.40 | | −1.30 | | | |
| hsa-miR-454-3p | | | | | | 1.21 |
| hsa-miR-455-3p | | | | | | 1.17 |
| hsa-miR-455-5p | | | −1.12 | | 1.05 | |
| hsa-miR-4647 | | −1.31 | | | | |
| hsa-miR-4685-3p | −1.29 | | −1.44 | | | |
| hsa-miR-485-5p | | | | 1.13 | | |
| hsa-miR-486-5p | | | 1.52 | | | |
| hsa-miR-500a-3p | −1.22 | | | | | |
| hsa-miR-503-5p | | | | | | 1.49 |
| hsa-miR-542-3p | −1.24 | | | | | |
| hsa-miR-616-5p | | −1.32 | 1.58 | | | |
| hsa-miR-625-3p | | | | | | 1.46 |
| hsa-miR-625-5p | | | | | | 1.60 |
| hsa-miR-628-3p | 1.19 | | 1.34 | | | |
| hsa-miR-664a-5p | | | | 1.52 | | |
| hsa-miR-6723-5p | | −1.43 | | | | |
| hsa-miR-6852-5p | | | | 1.89 | 1.61 | |
| hsa-miR-769-3p | | | | | 1.70 | |
| hsa-miR-769-5p | −1.03 | −1.76 | | 1.38 | 1.54 | |
| hsa-miR-7706 | | | | −1.72 | | |
| hsa-miR-7856-5p | | | | −1.40 | | |
| hsa-miR-7975 | 1.59 | | | | | |

TABLE 37-continued

MicroRNA markers differentially expressed in urine based on the frequency of hits or the impact score

| MicroRNA | High_freq_hits vs. Baseline | High_freq_hits vs. Low_freq_hits | Low_freq_hits vs. Baseline | Max_hitsp vs. Baseline | Min_hitsp vs. Baseline | Min_hitsp vs. Low_freq_hits |
|---|---|---|---|---|---|---|
| hsa-miR-874-3p | | | | | 1.37 | |
| hsa-miR-92a-1-5p | | | | | 1.25 | |
| hsa-miR-93-3p | | | | | | 1.22 |
| hsa-miR-939-5p | | | | 1.06 | | |
| hsa-miR-98-3p | | | | | −1.56 | |

TABLE 38

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-let-7f-1-3p | | | | 1.18 | 1.09 | 1.05 |
| hsa-miR-106a-3p | | −1.21 | | −1.09 | | |
| hsa-miR-1224-5p | | −1.12 | | −1.08 | | |
| hsa-miR-1228-3p | | | | 1.08 | | |
| hsa-miR-125b-1-3p | | | | 1.30 | | |
| hsa-miR-1291 | 1.65 | | −1.21 | −1.67 | | |
| hsa-miR-1323 | | −1.34 | | | | 1.67 |
| hsa-miR-135a-5p | | | | 1.16 | | |
| hsa-miR-138-1-3p | | | | | | 1.06 |
| hsa-miR-144-3p | | −1.05 | | −1.09 | | |
| hsa-miR-144-5p | | | | −1.02 | | |
| hsa-miR-149-5p | | −1.04 | 1.07 | | 1.86 | 2.11 |
| hsa-miR-16-2-3p | | −1.02 | | | | |
| hsa-miR-184 | | | | 1.36 | | |
| hsa-miR-18b-3p | −1.25 | | | −1.53 | | |
| hsa-miR-193b-5p | 1.25 | | | | | |
| hsa-miR-195-3p | 1.39 | | | | −1.31 | |
| hsa-miR-203a-3p | | | | | | 1.31 |
| hsa-miR-212-5p | 1.11 | | | 1.28 | | |
| hsa-miR-214-3p | 1.45 | | −2.34 | | | 1.69 |
| hsa-miR-218-5p | −1.39 | −1.73 | | | | 1.16 |
| hsa-miR-219a-2-3p | | | | | 1.21 | 1.11 |
| hsa-miR-31-5p | | | −1.25 | | | |
| hsa-miR-3127-5p | −1.02 | −1.20 | | | | |
| hsa-miR-3159 | | | | 1.06 | | |
| hsa-miR-3163 | −1.27 | −1.52 | | −1.26 | | |
| hsa-miR-3168 | 1.13 | | | 1.16 | | |
| hsa-miR-320b | | | | 1.05 | | |
| hsa-miR-34c-5p | −1.53 | −2.30 | | −1.56 | | |
| hsa-miR-362-3p | | | | −1.08 | −1.07 | |
| hsa-miR-3688-5p | | −1.20 | | −1.04 | | |
| hsa-miR-378b | | 1.18 | 1.12 | 1.40 | 1.35 | |
| hsa-miR-378f | | 1.32 | 1.16 | | | |
| hsa-miR-378g | | 1.35 | 1.51 | | | |
| hsa-miR-4436b-3p | −1.23 | −1.24 | | | 1.41 | 1.42 |
| hsa-miR-4466 | −1.14 | | | | 1.40 | 1.03 |
| hsa-miR-449b-5p | | −1.37 | | −1.15 | | |
| hsa-miR-451a | | −1.10 | | | | |
| hsa-miR-4726-5p | 1.41 | | −1.55 | | −1.25 | |
| hsa-miR-4745-3p | −1.41 | −1.44 | | | | |
| hsa-miR-4745-5p | | 1.28 | 1.22 | 1.34 | 1.28 | |
| hsa-miR-4772-3p | | −1.15 | | −1.34 | | |
| hsa-miR-483-3p | | −1.46 | | | | 1.37 |
| hsa-miR-5100 | | | | 1.25 | 1.05 | |
| hsa-miR-512-3p | −1.07 | −1.93 | | | | 1.36 |
| hsa-miR-515-3p | | | | 2.08 | 2.04 | 1.65 |
| hsa-miR-516b-5p | | −1.68 | | | | 1.10 |
| hsa-miR-582-3p | | −1.02 | | | | |
| hsa-miR-590-5p | 1.16 | 1.16 | | 1.17 | | |
| hsa-miR-615-3p | 1.24 | | −1.72 | | −1.49 | |
| hsa-miR-6832-5p | | 1.48 | 1.70 | | −1.72 | |
| hsa-miR-6850-5p | −1.27 | −1.28 | | | 1.57 | 1.59 |
| hsa-miR-6858-5p | | | | 1.11 | 1.16 | 1.27 |
| hsa-miR-7975 | | 1.21 | | 1.35 | 1.14 | |
| hsa-miR-8061 | | | −1.21 | | | 1.44 |
| hsa-miR-8072 | | | | 1.42 | 1.29 | 1.80 |
| hsa-miR-873-3p | | | 1.20 | | | |

TABLE 38-continued

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-873-5p | | | | | 1.72 | |
| hsa-miR-887-3p | −1.16 | | | | | |

TABLE 39

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-let-7a-3p | | | 1.03 | | 1.16 | |
| hsa-let-7g-3p | | | | −1.08 | | |
| hsa-miR-1-3p | −1.45 | | | | | |
| hsa-miR-106a-3p | | −1.14 | | | | |
| hsa-miR-1226-3p | | | | 1.02 | | |
| hsa-miR-1234-3p | | | | | 1.42 | |
| hsa-miR-1247-5p | | | | | | −1.06 |
| hsa-miR-127-3p | −1.34 | 1.42 | | | | |
| hsa-miR-127-5p | | 1.04 | | | | |
| hsa-miR-1275 | | | | 1.33 | | |
| hsa-miR-1283 | | | | 3.31 | | |
| hsa-miR-1287-5p | | | 1.09 | | | |
| hsa-miR-1288-3p | | | | | 2.76 | |
| hsa-miR-1291 | 1.27 | | | | −1.28 | |
| hsa-miR-1298-5p | | −1.86 | | | | |
| hsa-miR-1298-5p | | −1.09 | | | | |
| hsa-miR-1323 | | −1.03 | | | | |
| hsa-miR-134-5p | −1.03 | | | | | |
| hsa-miR-135a-5p | | | | 1.00 | | |
| hsa-miR-139-3p | | | | | 1.12 | |
| hsa-miR-144-3p | | −1.06 | | −1.11 | | |
| hsa-miR-144-5p | | | | −1.06 | | |
| hsa-miR-146a-3p | −1.02 | | | | | |
| hsa-miR-149-5p | | | | | 1.24 | 1.46 |
| hsa-miR-153-3p | | | | | | 1.44 |
| hsa-miR-16-2-3p | | | | −1.05 | | |
| hsa-miR-182-5p | | −1.10 | | | | |
| hsa-miR-183-5p | −1.07 | −1.22 | | −1.06 | | |
| hsa-miR-183-5p | | | | −1.15 | | −1.06 |
| hsa-miR-18b-3p | −1.17 | −1.03 | | −1.44 | | |
| hsa-miR-1911-5p | | | | | | −1.11 |
| hsa-miR-193b-3p | | | −1.42 | | | |
| hsa-miR-193b-3p | | | 1.90 | 1.91 | | |
| hsa-miR-195-3p | 1.36 | | | | −1.05 | |
| hsa-miR-203a-3p | | | | | 1.66 | |
| hsa-miR-208b-3p | 2.01 | | | | | |
| hsa-miR-20a-3p | | | | −1.10 | 1.38 | |
| hsa-miR-211-5p | | | | | | 1.06 |
| hsa-miR-2115-3p | | | | | −1.56 | |
| hsa-miR-212-5p | | | | 1.17 | | |
| hsa-miR-214-3p | 1.31 | | −1.79 | | −1.12 | |
| hsa-miR-214-5p | | | | | | 1.01 |
| hsa-miR-218-5p | −1.29 | −1.56 | | −1.21 | | |
| hsa-miR-219b-5p | | | 1.31 | | | |
| hsa-miR-2276-3p | 1.01 | | | | 1.58 | |
| hsa-miR-2392 | −2.30 | | | | | |
| hsa-miR-23b-5p | | | | | −1.51 | |
| hsa-miR-23c | 2.24 | | | | | |
| hsa-miR-26a-2-3p | | | 1.44 | | | |
| hsa-miR-296-5p | | −1.00 | | | | |
| hsa-miR-29b-2-5p | | | | −1.47 | 1.07 | |
| hsa-miR-3064-5p | 1.04 | | | | | |
| hsa-miR-30b-5p | | | 1.21 | | | |
| hsa-miR-31-5p | | | −1.02 | | | |
| hsa-miR-3115 | | | 1.31 | | | |
| hsa-miR-3121-3p | 1.05 | 1.02 | | | | |
| hsa-miR-3121-3p | | 1.91 | | | | 1.36 |
| hsa-miR-3122 | −1.98 | | | −2.93 | | |
| hsa-miR-3136-5p | | | | −1.35 | | |
| hsa-miR-3158-5p | | −1.29 | | | | |
| hsa-miR-3160-3p | | | | −1.11 | | |
| hsa-miR-3160-5p | | | | −1.29 | | |

TABLE 39-continued

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-3163 | −1.18 | −1.35 | | −1.19 | | |
| hsa-miR-3168 | | 1.37 | | | | |
| hsa-miR-3173-3p | | | | | −1.02 | |
| hsa-miR-3182 | | −1.56 | | | −1.95 | |
| hsa-miR-3184-5p | | | | 3.62 | −2.93 | |
| hsa-miR-3187-5p | −2.48 | 1.63 | | | | |
| hsa-miR-3194-3p | | | −1.01 | | | |
| hsa-miR-3194-5p | | | | −1.52 | 1.66 | |
| hsa-miR-320a | | | 1.25 | | | |
| hsa-miR-320b | | | | 1.10 | | |
| hsa-miR-324-3p | | | | | 1.00 | |
| hsa-miR-328-5p | | 1.51 | | | 2.06 | |
| hsa-miR-337-5p | −1.02 | | | | | |
| hsa-miR-34c-5p | | −1.53 | | | | |
| hsa-miR-3529-3p | | | | −3.12 | 2.67 | |
| hsa-miR-365a-3p = hsa-miR-365b-3p | | −1.45 | | | | |
| hsa-miR-3682-3p | | | | | | −1.11 |
| hsa-miR-3688-5p | | −1.00 | | | | |
| hsa-miR-3691-5p | | | −1.02 | | | |
| hsa-miR-371a-3p | −1.42 | | | | | |
| hsa-miR-371a-5p | | | | 2.86 | | |
| hsa-miR-371b-5p | | −1.06 | | | | |
| hsa-miR-373-3p | | | | | 1.15 | |
| hsa-miR-373-3p | | | | | | −1.40 |
| hsa-miR-377-5p | −1.67 | | | | | |
| hsa-miR-378b | | | | 1.06 | 1.51 | |
| hsa-miR-378e | −1.36 | | | | | |
| hsa-miR-378g | | | | | 1.11 | |
| hsa-miR-380-3p | | | | −1.08 | | |
| hsa-miR-382-5p | −1.24 | | | | | |
| hsa-miR-383-5p | −3.75 | | | | | |
| hsa-miR-3940-3p | −1.34 | | | −1.80 | 1.14 | |
| hsa-miR-4326 | −1.22 | | | | | |
| hsa-miR-4424 | | | −2.18 | −2.09 | | |
| hsa-miR-4436b-3p | −1.00 | | | | 1.15 | 1.10 |
| hsa-miR-4440 | −1.98 | 1.86 | | | | |
| hsa-miR-4443 | | | | | | −1.02 |
| hsa-miR-4448 | −1.99 | | 2.19 | | | |
| hsa-miR-4449 | | | 1.37 | 1.32 | | |
| hsa-miR-4461 | | −1.76 | | | | |
| hsa-miR-4467 | | | | 3.03 | | |
| hsa-miR-4474-3p | | | | −2.00 | | |
| hsa-miR-4479 | | | | | | 1.14 |
| hsa-miR-4482-3p | | | | −1.07 | | |
| hsa-miR-4489 | −2.76 | 2.42 | | | | |
| hsa-miR-449b-5p | | −1.15 | | | | |
| hsa-miR-4510 | −2.01 | | | | | |
| hsa-miR-451a | | −1.02 | | | | |
| hsa-miR-455-3p | 2.74 | | | | | |
| hsa-miR-455-5p | | | −1.16 | | −1.29 | |
| hsa-miR-4646-5p | | | | 1.10 | | |
| hsa-miR-4654 | | | 1.29 | | | |
| hsa-miR-4654 | | | | 1.32 | | |
| hsa-miR-4657 | | 1.04 | | | | |
| hsa-miR-4667-5p | | | 1.16 | | | |
| hsa-miR-4668-5p | | | | −2.38 | | |
| hsa-miR-4707-3p | | 1.02 | | | | |
| hsa-miR-4709-5p | | | | | | 1.18 |
| hsa-miR-4726-5p | 1.10 | | −1.18 | | | |
| hsa-miR-4732-3p | | | 1.02 | | | |
| hsa-miR-4738-3p | | | | | 1.31 | |
| hsa-miR-4743-5p | | | 1.23 | | | |
| hsa-miR-4745-5p | | | | | | 1.18 |
| hsa-miR-4747-5p | | | | 1.15 | | 1.24 |
| hsa-miR-4748 | | | | 1.38 | | |
| hsa-miR-4755-5p | | | | −1.79 | | |
| hsa-miR-4762-5p | −1.43 | | | −1.18 | 1.04 | |
| hsa-miR-4767 | | | | −1.19 | | |
| hsa-miR-4772-3p | | | | −1.21 | | |
| hsa-miR-4783-3p | | 2.10 | | | | |
| hsa-miR-4785 | | | 1.15 | | | |
| hsa-miR-4797-3p | | | | | | −1.03 |
| hsa-miR-483-3p | | −1.21 | | | | |
| hsa-miR-485-5p | −1.01 | | | | | |
| hsa-miR-490-3p | −1.32 | | | −1.25 | | |

TABLE 39-continued

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-494-5p | −1.65 | | | | | |
| hsa-miR-499a-5p | 1.65 | | | | | |
| hsa-miR-5009-5p | | | −1.32 | | | |
| hsa-miR-5009-5p | | | 1.41 | | | −1.36 |
| hsa-miR-500b-3p | | | −1.95 | | | |
| hsa-miR-501-5p | | | | −1.48 | | |
| hsa-miR-503-3p | −2.25 | 2.07 | | | | |
| hsa-miR-503-3p | | 1.15 | | | | |
| hsa-miR-512-3p | | −1.29 | | | | 1.21 |
| hsa-miR-516a-5p | | | 2.75 | 3.87 | | |
| hsa-miR-516a-5p | | | | | | 1.15 |
| hsa-miR-516b-5p | | −1.00 | | | | 1.30 |
| hsa-miR-517a-3p = hsa-miR-517b-3p | | | | 3.48 | | |
| hsa-miR-517c-3p | | | 2.88 | 2.96 | | |
| hsa-miR-5189-3p | −1.43 | | | | | |
| hsa-miR-518b | | | 2.77 | 3.19 | | |
| hsa-miR-518c-3p | | | | 2.72 | | |
| hsa-miR-518e-5p = hsa-miR-519a-5p = hsa-miR-519b-5p = hsa-miR-519c-5p = hsa-miR-522-5p = hsa-miR-523-5p | | | 2.65 | 3.12 | | |
| hsa-miR-519c-3p | | | | 2.74 | | |
| hsa-miR-519d-3p | | | 2.70 | | | |
| hsa-miR-520d-5p | | | 2.56 | 2.74 | | |
| hsa-miR-526b-5p | | | 2.33 | | | |
| hsa-miR-541-3p | | −1.29 | | | | |
| hsa-miR-542-5p | −1.03 | | | | | |
| hsa-miR-543 | −1.00 | | | | | |
| hsa-miR-548ac | | | | −1.08 | | |
| hsa-miR-548as-3p | 1.12 | | | | | |
| hsa-miR-548as-3p | | | | | | 1.48 |
| hsa-miR-550b-2-5p | | | | −1.04 | | |
| hsa-miR-551a | −1.59 | | | | | |
| hsa-miR-5583-3p | | | 1.11 | | | |
| hsa-miR-5695 | | | | −1.09 | | |
| hsa-miR-577 | | | | | 1.03 | |
| hsa-miR-590-5p | 1.00 | 1.01 | | 1.05 | | |
| hsa-miR-6130 | | | | 3.20 | −3.21 | |
| hsa-miR-6131 | | | | | | −1.05 |
| hsa-miR-615-3p | 1.08 | | −1.25 | | −1.24 | |
| hsa-miR-615-5p | | 2.74 | | | | |
| hsa-miR-616-3p | | | | 1.06 | | |
| hsa-miR-629-5p | −1.08 | | | −1.29 | | |
| hsa-miR-642a-3p | | | | 2.91 | −1.93 | |
| hsa-miR-642b-5p | | | | 2.82 | −1.94 | |
| hsa-miR-6501-5p | | | | | | 1.12 |
| hsa-miR-6503-3p | | | | −1.48 | | |
| hsa-miR-6509-5p | −1.22 | 1.12 | | | 1.20 | |
| hsa-miR-6511a-5p | | | 1.64 | 1.85 | | |
| hsa-miR-6511b-5p | | | 1.18 | 1.53 | | |
| hsa-miR-6726-3p | | −1.33 | | | | |
| hsa-miR-6730-5p | | | 1.20 | | | |
| hsa-miR-6734-5p | | | | | | −1.04 |
| hsa-miR-6735-3p | | | 1.56 | | | |
| hsa-miR-6738-5p | −2.89 | | | | | |
| hsa-miR-6740-5p | −2.13 | | | | | |
| hsa-miR-6749-3p | −1.63 | | | | | |
| hsa-miR-675-5p | | 2.70 | 2.12 | | | |
| hsa-miR-6751-3p | | 1.69 | | | 2.37 | |
| hsa-miR-6764-3p | | 1.05 | | | | |
| hsa-miR-6767-5p | | −1.48 | | | −1.55 | |
| hsa-miR-6770-3p | | | | −1.44 | 1.33 | |
| hsa-miR-6770-5p | | | 1.44 | | | |
| hsa-miR-6777-3p | | | | 1.11 | | |
| hsa-miR-6780a-5p | | | | 1.55 | | |
| hsa-miR-6781-5p | −2.38 | | 3.23 | | | |
| hsa-miR-6782-3p | | | | 2.15 | | |
| hsa-miR-6787-5p | | | | 1.81 | | |
| hsa-miR-6791-5p | | | 1.59 | 2.55 | | |
| hsa-miR-6793-3p | | | | | 1.02 | |
| hsa-miR-6809-3p | | 1.02 | | | | |
| hsa-miR-6820-5p | | | | 1.35 | 1.10 | 1.49 |
| hsa-miR-6840-3p | | | 3.03 | 2.75 | | |
| hsa-miR-6850-5p | −1.00 | | | | | |
| hsa-miR-6851-5p | | | 1.90 | | | |

TABLE 39-continued

MicroRNA markers that are differentially expressed in plasma based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-6858-5p | | | | 1.03 | | |
| hsa-miR-6859-3p | −1.13 | | | | | |
| hsa-miR-6875-5p | | | | | 1.46 | |
| hsa-miR-6877-3p | 1.00 | | | | | |
| hsa-miR-6878-5p | 2.59 | | | | | |
| hsa-miR-6879-3p | | | | | 1.10 | |
| hsa-miR-6885-5p | | | 2.31 | 2.29 | | |
| hsa-miR-6886-5p | −1.85 | | | | | |
| hsa-miR-6889-3p | | | | | 1.69 | |
| hsa-miR-6894-3p | | | | 1.08 | | |
| hsa-miR-7-5p | | | | −2.84 | 2.64 | |
| hsa-miR-7106-3p | | 2.30 | | | 2.76 | |
| hsa-miR-7110-3p | | | | 1.19 | | |
| hsa-miR-7155-3p | | | | −1.26 | | |
| hsa-miR-760 | | | | | 1.40 | |
| hsa-miR-769-5p | | | | 1.14 | | |
| hsa-miR-7975 | | 1.08 | | | | |
| hsa-miR-8061 | 1.00 | | −1.23 | | −1.07 | |
| hsa-miR-8072 | | | | 1.15 | 1.08 | 1.43 |
| hsa-miR-885-5p | | −1.08 | | | | |
| hsa-miR-92b-5p | | | | −1.39 | 1.02 | |
| hsa-miR-939-3p | | | | | 1.70 | |
| hsa-miR-939-5p | −1.20 | 1.18 | | | | |
| hsa-miR-940 | | | | 1.02 | 1.20 | |
| hsa-miR-98-3p | | | | | 1.17 | |

TABLE 40

MicroRNA markers that are differentially expressed in urine based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-122-5p | | −1.73 | −2.58 | | −2.40 | |
| hsa-miR-1226-3p | −2.49 | | | | 1.91 | |
| hsa-miR-1246 | | | | −1.12 | | −1.11 |
| hsa-miR-125a-3p | −2.87 | −2.97 | | −1.92 | | |
| hsa-miR-125b-1-3p | | 1.44 | 1.38 | | −1.65 | |
| hsa-miR-126-5p | | | | −1.19 | | −1.01 |
| hsa-miR-127-3p | −1.93 | | 1.21 | −1.11 | | |
| hsa-miR-1275 | −1.98 | −2.43 | | −1.58 | | |
| hsa-miR-1307-3p | −2.18 | −1.78 | | −1.56 | | |
| hsa-miR-143-3p | −1.27 | −1.50 | | −1.37 | | |
| hsa-miR-146a-5p | −1.86 | | | −1.44 | | |
| hsa-miR-148b-5p | −1.09 | −1.32 | | −1.27 | | |
| hsa-miR-185-3p | −1.18 | −2.18 | | | 1.72 | |
| hsa-miR-187-3p | −1.39 | −2.50 | −1.10 | | 1.87 | |
| hsa-miR-190a-5p | | −1.21 | | −1.62 | | |
| hsa-miR-1910-5p | −1.90 | −2.61 | | −1.89 | | |
| hsa-miR-199a-3p = hsa-miR-199b-3p | | | | −1.25 | −1.16 | |
| hsa-miR-203b-5p | −1.81 | −1.86 | | −2.75 | | |
| hsa-miR-204-3p | −2.10 | −2.94 | | −1.45 | 1.49 | |
| hsa-miR-210-3p | −2.21 | −2.03 | | | 1.36 | 1.17 |
| hsa-miR-210-5p | −1.29 | −2.22 | | −1.25 | | |
| hsa-miR-212-3p | −2.29 | | | −2.02 | | |
| hsa-miR-221-3p | −1.47 | −1.46 | | | | |
| hsa-miR-25-5p | −1.28 | −2.25 | | | 1.46 | |
| hsa-miR-296-3p | −2.48 | | 1.54 | | | |
| hsa-miR-3168 | | −2.25 | | −1.67 | | |
| hsa-miR-3184-3p | −2.37 | −1.81 | | −1.93 | | |
| hsa-miR-320a | −1.85 | −1.12 | | −1.37 | | |
| hsa-miR-320b | −2.58 | −1.14 | 1.44 | | 2.03 | |
| hsa-miR-320c | −2.45 | −1.96 | | −1.56 | | |
| hsa-miR-328-3p | −1.92 | | | −1.38 | | |
| hsa-miR-331-3p | −1.65 | −3.08 | −1.43 | −1.05 | 2.02 | |
| hsa-miR-339-5p | −1.23 | | 1.53 | | | |
| hsa-miR-33b-5p | | 1.84 | 1.66 | | | |
| hsa-miR-378a-3p | −2.01 | | 1.62 | | 1.04 | |
| hsa-miR-378c | −2.15 | −2.28 | | −1.38 | | |
| hsa-miR-378e | −1.45 | −1.19 | | | | |
| hsa-miR-378f | −2.15 | −1.82 | | | | |

TABLE 40-continued

MicroRNA markers that are differentially expressed in urine based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-423-5p | −2.11 | −1.08 | 1.03 | −1.34 | | |
| hsa-miR-4443 | −3.05 | −3.50 | | −2.73 | | |
| hsa-miR-4461 | −1.71 | −1.57 | | −2.32 | | |
| hsa-miR-4488 | −1.60 | −2.57 | | | | 2.11 |
| hsa-miR-4510 | 1.23 | | | 1.14 | | |
| hsa-miR-451a | −1.23 | | | | | |
| hsa-miR-455-5p | | | | | 1.57 | 1.43 |
| hsa-miR-485-5p | −1.78 | −1.82 | | | | |
| hsa-miR-486-3p | −2.19 | −2.53 | | −2.55 | | |
| hsa-miR-486-5p | −2.94 | −2.73 | | −2.84 | | |
| hsa-miR-500a-3p | −2.02 | −1.94 | | −1.18 | | |
| hsa-miR-501-5p | −2.43 | −3.06 | | −1.82 | | |
| hsa-miR-5100 | −1.36 | −2.16 | | −1.14 | | |
| hsa-miR-532-3p | −1.63 | −2.60 | | −1.46 | | 1.14 |
| hsa-miR-574-3p | | −1.85 | −1.42 | | | 1.69 |
| hsa-miR-615-3p | −2.04 | −2.66 | | −1.02 | 1.02 | 1.65 |
| hsa-miR-664a-5p | −1.62 | −1.34 | | −1.18 | | |
| hsa-miR-671-5p | | −1.72 | −1.90 | | | |
| hsa-miR-6723-5p | −2.26 | −2.10 | | −2.19 | | |
| hsa-miR-6852-5p | −1.91 | −1.63 | | | | |
| hsa-miR-6858-5p | −1.63 | −2.33 | | −1.55 | | |
| hsa-miR-708-5p | −1.39 | −2.36 | | | | |
| hsa-miR-7160-5p | −2.29 | −2.40 | | −2.86 | | |
| hsa-miR-769-5p | | | 1.17 | | | |
| hsa-miR-8061 | −2.54 | −2.79 | | −2.98 | | |
| hsa-miR-874-3p | −2.62 | | 1.67 | −1.28 | 1.34 | |
| hsa-miR-874-5p | −2.39 | −2.56 | | −1.73 | | |
| hsa-miR-888-5p | 1.11 | 1.38 | | 1.22 | | |
| hsa-miR-892a | 2.39 | 2.08 | | 2.11 | | |

TABLE 41

MicroRNA markers that are differentially expressed in urine based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-1226-3p | −3.21 | −1.70 | 1.51 | | 2.07 | |
| hsa-miR-874-3p | −2.06 | −2.58 | | | 1.18 | 1.69 |
| hsa-miR-664a-5p | −1.99 | −1.12 | | −1.15 | | |
| hsa-miR-4461 | −1.75 | | 1.53 | −1.69 | | −1.47 |
| hsa-miR-150-5p | −1.71 | | | | 1.62 | |
| hsa-miR-615-3p | −1.61 | −1.71 | | | 1.01 | 1.11 |
| hsa-miR-185-5p | −1.58 | | | | | |
| hsa-miR-500a-3p | −1.42 | −1.48 | | | | |
| hsa-miR-93-3p | −1.40 | −1.52 | | | | |
| hsa-miR-204-3p | −1.38 | −2.14 | | | | 1.41 |
| hsa-miR-1307-3p | −1.37 | −2.25 | | | | 1.29 |
| hsa-miR-1304-3p | −1.35 | −1.33 | | | | |
| hsa-miR-4443 | −1.35 | −1.65 | | −1.23 | | |
| hsa-miR-4728-3p | −1.30 | | | | 1.19 | |
| hsa-miR-296-3p | −1.28 | −1.35 | | | | |
| hsa-miR-320a | −1.26 | −1.19 | | | 1.28 | 1.20 |
| hsa-miR-362-5p | −1.24 | | | −1.10 | | |
| hsa-miR-502-3p | −1.22 | −1.15 | | | | |
| hsa-miR-148b-5p | −1.21 | −1.51 | | −1.08 | | |
| hsa-miR-532-3p | −1.20 | −1.75 | | −1.27 | | |
| hsa-miR-320c | −1.20 | | | | | |
| hsa-miR-130b-5p | −1.19 | | | | | |
| hsa-miR-221-3p | −1.18 | −1.30 | | | | |
| hsa-miR-501-5p | −1.18 | −1.20 | | −1.12 | | |
| hsa-miR-187-3p | −1.17 | −1.68 | | | | 1.04 |
| hsa-miR-185-3p | −1.16 | −1.98 | | | | 1.76 |
| hsa-miR-3605-5p | −1.15 | −1.41 | | | | |
| hsa-miR-708-5p | −1.14 | −1.56 | | −1.15 | | |
| hsa-miR-92a-1-5p | −1.12 | −1.24 | | | | |
| hsa-miR-328-3p | −1.08 | −1.91 | | | | 1.19 |
| hsa-miR-210-5p | −1.05 | −1.64 | | | | |
| hsa-miR-320e | −1.04 | | | | | |
| hsa-miR-504-5p | 1.00 | | | | | |
| hsa-let-7c-5p | 1.06 | 1.30 | | | | |
| hsa-miR-98-3p | 1.08 | 1.42 | | 1.04 | | |

TABLE 41-continued

MicroRNA markers that are differentially expressed in urine based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-let-7a-5p | 1.10 | 1.03 | | | | |
| hsa-miR-375 | 1.16 | 1.17 | | | | |
| hsa-miR-4510 | 1.23 | | | | | |
| hsa-miR-410-3p | 1.24 | 1.24 | | | | |
| hsa-miR-122-5p | 1.30 | | −1.59 | | −1.20 | |
| hsa-miR-449a | 1.30 | | | | | |
| hsa-miR-449c-5p | 1.36 | | | 1.87 | | |
| hsa-miR-7704 | 1.38 | | | | | |
| hsa-miR-1255a | 1.41 | | | | | |
| hsa-miR-1908-3p | 1.45 | | −1.27 | | | |
| hsa-miR-3064-5p | 1.46 | | | | | |
| hsa-miR-508-3p | 1.49 | | | | | |
| hsa-miR-149-3p | 1.57 | | | 1.55 | | |
| hsa-miR-223-5p | 1.73 | 1.70 | | | | |
| hsa-miR-892a | 1.91 | 1.77 | | 1.71 | | |
| hsa-miR-331-3p | | −1.78 | | | | 1.49 |
| hsa-miR-146b-3p | | −1.60 | | | 1.30 | 1.93 |
| hsa-miR-339-5p | | −1.52 | −1.12 | | | 1.56 |
| hsa-miR-1269b | | −1.50 | | | | |
| hsa-miR-378c | | −1.45 | | | | 1.43 |
| hsa-miR-3928-3p | | −1.42 | | | | |
| hsa-miR-3182 | | −1.38 | | | | |
| hsa-miR-188-5p | | −1.35 | | | | |
| hsa-miR-542-5p | | −1.33 | | | | |
| hsa-miR-378a-3p | | −1.32 | | | | 1.17 |
| hsa-miR-1307-5p | | −1.28 | | | | |
| hsa-miR-3158-3p | | −1.26 | | | | |
| hsa-miR-210-3p | | −1.24 | | | | 1.20 |
| hsa-miR-574-3p | | −1.23 | | | | 1.11 |
| hsa-miR-378e | | −1.22 | | | | 1.15 |
| hsa-miR-653-5p | | −1.22 | | −1.66 | | |
| hsa-miR-1910-5p | | −1.21 | | | | |
| hsa-miR-125a-3p | | −1.17 | | | | 1.08 |
| hsa-miR-31-5p | | −1.16 | | | | |
| hsa-miR-489-3p | | −1.14 | | −1.06 | | |
| hsa-miR-324-3p | | −1.13 | | | | 1.08 |
| hsa-miR-190a-5p | | −1.12 | | −1.74 | | |
| hsa-miR-423-3p | | −1.08 | | | | |
| hsa-miR-450a-5p | | −1.07 | | | | |
| hsa-miR-181a-2-3p | | −1.06 | | | | |
| hsa-miR-484 | | −1.03 | | | | |
| hsa-miR-26b-3p | | −1.01 | | | | |
| hsa-miR-518a-3p | | 1.02 | 1.06 | | | |
| hsa-miR-25-3p | | 1.02 | | | | |
| hsa-miR-184 | | 1.16 | | | | |
| hsa-miR-130b-3p | | 1.21 | | | | |
| hsa-miR-126-3p | | 1.22 | 1.13 | | | −1.21 |
| hsa-miR-548i | | 1.25 | | | | |
| hsa-miR-584-5p | | 1.27 | | 1.32 | | |
| hsa-miR-107 | | 1.28 | | | | |
| hsa-miR-320b | | 1.29 | | | | −1.02 |
| hsa-miR-199a-5p | | 1.29 | | | | −1.25 |
| hsa-miR-517a-3p = hsa-miR-517b-3p | | 1.32 | 1.14 | | | −1.24 |
| hsa-miR-27a-3p | | 1.32 | | | | −1.11 |
| hsa-miR-152-5p | | 1.32 | 1.16 | | | |
| hsa-miR-143-3p | | 1.32 | | | | −1.69 |
| hsa-miR-1283 | | 1.32 | 1.18 | | | −1.31 |
| hsa-miR-888-5p | | 1.35 | | 1.12 | | |
| hsa-miR-512-3p | | 1.37 | 1.37 | | | −1.55 |
| hsa-miR-1323 | | 1.38 | | | | −1.50 |
| hsa-miR-199a-3p = hsa-miR-199b-3p | | 1.40 | | | | −1.57 |
| hsa-miR-136-3p | | 1.40 | | | | |
| hsa-miR-301b-3p | | 1.53 | | 1.25 | | |
| hsa-miR-516a-5p | | 1.56 | | | | −1.70 |
| hsa-miR-126-5p | | 1.58 | | | | −1.16 |
| hsa-miR-515-5p | | 1.72 | 1.54 | | | −2.03 |
| hsa-miR-3913-3p | | | −1.34 | | −1.30 | |
| hsa-miR-744-3p | | | −1.23 | | −1.44 | |
| hsa-miR-149-5p | | | −1.18 | | | 1.21 |
| hsa-miR-4448 | | | −1.03 | | −1.53 | |
| hsa-let-7f-2-3p | | | 1.07 | | | |
| hsa-miR-4326 | | | 1.42 | | | |
| hsa-miR-628-5p | | | | −1.37 | | |

TABLE 41-continued

MicroRNA markers that are differentially expressed in urine based on subjects' probability score for the risk of concussion

| MicroRNA | X1_vs_0 | X2_vs_0 | X2_vs_1 | X3_vs_0 | X3_vs_1 | X3_vs_2 |
|---|---|---|---|---|---|---|
| hsa-miR-651-5p | | | −1.32 | | −1.57 | |
| hsa-miR-4488 | | | 1.14 | | | 1.38 |
| hsa-miR-125b-1-3p | | | 1.20 | | | |
| hsa-miR-365b-5p | | | 1.24 | | | |
| hsa-miR-199b-5p | | | 1.25 | | 1.26 | |
| hsa-miR-4746-5p | | | 1.29 | | 1.34 | |
| hsa-miR-891a-5p | | | 1.42 | | 1.00 | |
| hsa-miR-487b-3p | | | 1.56 | | | |
| hsa-miR-92a-2-5p | | | 1.89 | | | 1.61 |
| hsa-miR-133a-3p | | | 1.95 | | 1.55 | |
| hsa-miR-1298-5p | | | 2.48 | | 1.60 | 1.79 |
| hsa-miR-1911-5p | | | 2.52 | | 1.77 | 1.85 |
| hsa-miR-190a-3p | | | | | −1.39 | |
| hsa-miR-20a-5p | | | | | −1.13 | |
| hsa-miR-138-5p | | | | | 1.00 | 1.32 |
| hsa-miR-22-5p | | | | | 1.23 | |
| hsa-miR-3651 | | | | | 1.32 | |
| hsa-miR-323b-3p | | | | | 1.32 | |
| hsa-miR-338-5p | | | | | 1.43 | |
| hsa-miR-455-5p | | | | | 1.54 | 1.55 |
| hsa-miR-516b-5p | | | | | | −1.45 |
| hsa-miR-99a-5p | | | | | | 1.03 |
| hsa-miR-877-5p | | | | | | 1.08 |
| hsa-miR-9-5p | | | | | | 1.08 |
| hsa-miR-181a-3p | | | | | | 1.14 |
| hsa-miR-378d | | | | | | 1.20 |
| hsa-miR-3913-5p | | | | | | 1.28 |
| hsa-miR-324-5p | | | | | | 1.32 |
| hsa-miR-326 | | | | | | 1.43 |

TABLE 42

List of miRNAs detectable in plasma that is determined by random forest classification to be most useful in comparing High_freq_hits and Baseline

| MeanDecreaseGini | miRNA_ID |
|---|---|
| 3.14 | hsa-miR-18b-3p |
| 2.37 | hsa-miR-873-5p |
| 2.23 | hsa-miR-579-5p |
| 1.91 | hsa-miR-204-5p |
| 1.88 | hsa-miR-1256 |
| 1.83 | hsa-miR-7851-3p |
| 1.80 | hsa-miR-7852-3p |
| 1.71 | hsa-miR-4467 |
| 1.57 | hsa-miR-193a-3p |
| 1.20 | hsa-miR-6829-5p |
| 1.15 | hsa-miR-6751-3p |
| 1.04 | hsa-miR-6850-5p |
| 0.94 | hsa-miR-3175 |
| 0.92 | hsa-miR-6885-3p |
| 0.89 | hsa-miR-512-3p |
| 0.85 | hsa-miR-548aq-5p |
| 0.81 | hsa-miR-1247-3p |
| 0.60 | hsa-miR-6876-5p |

TABLE 44

List of miRNAs detectable in plasma that is determined by random forest classification to be most useful in comparing Low_freq_hits and Baseline

| MeanDecreaseGini | miRNA_ID |
|---|---|
| 3.36 | hsa-miR-16-2-3p |
| 2.29 | hsa-miR-210-3p |
| 2.16 | hsa-miR-501-3p |
| 2.10 | hsa-miR-378a-3p |
| 1.94 | hsa-miR-1294 |
| 1.91 | hsa-miR-378c |
| 1.83 | hsa-miR-4685-3p |
| 1.74 | hsa-miR-579-5p |
| 1.71 | hsa-miR-214-3p |
| 1.65 | hsa-miR-4665-5p |
| 1.08 | hsa-miR-4479 |
| 1.08 | hsa-miR-1247-5p |
| 1.02 | hsa-miR-6767-5p |
| 0.95 | hsa-miR-3175 |
| 0.77 | hsa-miR-219b-5p |
| 0.73 | hsa-miR-4510 |
| 0.63 | hsa-miR-7975 |
| 0.55 | hsa-miR-4467 |
| 0.55 | hsa-miR-3942-3p |
| 0.49 | hsa-miR-4657 |
| 0.39 | hsa-miR-500b-3p |
| 0.27 | hsa-miR-6797-3p |
| 0.24 | hsa-miR-3146 |

TABLE 43

List of miRNAs detectable in plasma that is determined by random forest classification to be most useful in comparing High_freq_hits and Low_freq_hits

| MeanDecreaseGini | miRNA_ID |
|---|---|
| 1.59 | hsa-miR-550b-3p |
| 1.58 | hsa-miR-597-3p |
| 1.47 | hsa-miR-296-5p |
| 1.41 | hsa-miR-7851-3p |
| 1.24 | hsa-miR-378g |

TABLE 43-continued

List of miRNAs detectable in plasma that is determined by random forest classification to be most useful in comparing High_freq_hits and Low_freq_hits

| MeanDecreaseGini | miRNA_ID |
|---|---|
| 1.06 | hsa-miR-873-5p |
| 1.05 | hsa-miR-6783-3p |
| 1.01 | hsa-miR-107 |
| 0.98 | hsa-miR-378b |
| 0.93 | hsa-miR-1256 |
| 0.92 | hsa-miR-3688-3p |
| 0.92 | hsa-miR-4421 |
| 0.84 | hsa-miR-512-3p |
| 0.84 | hsa-miR-4732-3p |
| 0.81 | hsa-miR-1247-3p |
| 0.73 | hsa-miR-6804-5p |
| 0.68 | hsa-miR-2115-3p |
| 0.60 | hsa-miR-6885-3p |
| 0.58 | hsa-miR-516b-5p |
| 0.53 | hsa-miR-6767-5p |
| 0.52 | hsa-miR-3146 |
| 0.46 | hsa-miR-500b-3p |
| 0.43 | hsa-miR-517a-3p = hsa-miR-517b-3p |
| 0.37 | hsa-miR-4657 |
| 0.34 | hsa-miR-516a-5p |

TABLE 45

List of miRNAs detectable in plasma that is determined by random forest classification to be most useful in comparing Max_hitsp and Baseline

| MeanDecreaseGini | miRNA_ID |
|---|---|
| 2.21 | hsa-miR-483-3p |
| 1.75 | hsa-miR-4772-3p |
| 1.54 | hsa-miR-5001-3p |
| 1.32 | hsa-miR-1246 |
| 1.24 | hsa-miR-873-3p |
| 1.14 | hsa-miR-23b-5p |
| 1.09 | hsa-miR-125b-1-3p |
| 1.09 | hsa-miR-5004-3p |
| 1.04 | hsa-miR-378g |
| 0.96 | hsa-miR-3184-5p |
| 0.94 | hsa-miR-4642 |
| 0.93 | hsa-miR-4659a-3p |
| 0.90 | hsa-miR-561-5p |
| 0.83 | hsa-miR-1297 |
| 0.80 | hsa-miR-3180 |
| 0.72 | hsa-miR-3140-3p |
| 0.71 | hsa-miR-642a-3p |
| 0.69 | hsa-miR-6782-3p |
| 0.69 | hsa-miR-3180-3p |
| 0.67 | hsa-miR-642b-5p |
| 0.64 | hsa-miR-887-3p |
| 0.55 | hsa-miR-5190 |
| 0.52 | hsa-miR-4448 |
| 0.50 | hsa-miR-6781-5p |
| 0.39 | hsa-miR-517a-3p = hsa-miR-517b-3p |
| 0.33 | hsa-miR-122-3p |
| 0.10 | hsa-miR-1291 |

TABLE 47

List of miRNAs detectable in plasma that is determined by random forest classification to be most useful in comparing Min_hitsp and Baseline

| MeanDecreaseGini | miRNA_ID |
|---|---|
| 1.38 | hsa-miR-486-5p |
| 1.17 | hsa-miR-100-5p |

TABLE 47-continued

List of miRNAs detectable in plasma that is determined by random forest classification to be most useful in comparing Min_hitsp and Baseline

| MeanDecreaseGini | miRNA_ID |
|---|---|
| 1.02 | hsa-miR-7706 |
| 0.85 | hsa-miR-125b-1-3p |
| 0.82 | hsa-miR-501-3p |
| 0.78 | hsa-miR-18b-3p |
| 0.73 | hsa-miR-150-3p |
| 0.73 | hsa-miR-10b-5p |
| 0.70 | hsa-miR-490-3p |
| 0.69 | hsa-miR-6780a-5p |
| 0.67 | hsa-miR-125b-5p |
| 0.63 | hsa-miR-4647 |
| 0.62 | hsa-miR-320b |
| 0.59 | hsa-miR-423-5p |
| 0.51 | hsa-miR-378f |
| 0.47 | hsa-miR-320e |
| 0.45 | hsa-miR-371b-5p |
| 0.44 | hsa-miR-8061 |
| 0.41 | hsa-miR-887-3p |
| 0.39 | hsa-miR-455-5p |
| 0.38 | hsa-miR-642a-3p |
| 0.36 | hsa-miR-3617-5p |
| 0.35 | hsa-miR-483-5p |
| 0.34 | hsa-miR-642b-5p |
| 0.33 | hsa-miR-582-5p |
| 0.32 | hsa-miR-873-3p |
| 0.31 | hsa-miR-320c |
| 0.30 | hsa-miR-378b |
| 0.30 | hsa-miR-6727-5p |
| 0.30 | hsa-miR-378g |
| 0.26 | hsa-miR-371a-3p |
| 0.26 | hsa-miR-3180-3p |
| 0.26 | hsa-miR-885-5p |
| 0.25 | hsa-miR-624-3p |
| 0.23 | hsa-miR-3180 |
| 0.23 | hsa-miR-129-5p |
| 0.22 | hsa-miR-516a-5p |
| 0.21 | hsa-miR-4510 |
| 0.20 | hsa-miR-570-3p |
| 0.19 | hsa-miR-1323 |
| 0.16 | hsa-miR-6782-3p |
| 0.15 | hsa-miR-7703 |
| 0.15 | hsa-miR-518b |
| 0.15 | hsa-miR-6832-5p |
| 0.15 | hsa-miR-202-3p |
| 0.14 | hsa-miR-9-3p |
| 0.13 | hsa-miR-4477b |
| 0.13 | hsa-miR-6791-5p |
| 0.12 | hsa-miR-6740-5p |
| 0.11 | hsa-miR-6130 |
| 0.10 | hsa-miR-517a-3p = hsa-miR-517b-3p |
| 0.09 | hsa-miR-516b-5p |
| 0.09 | hsa-miR-196a-5p |
| 0.08 | hsa-miR-6754-3p |
| 0.04 | hsa-miR-4635 |
| 0.02 | hsa-miR-3622b-3p |

TABLE 46

List of miRNAs detectable in plasma that is determined by random forest classification to be most useful in comparing Max_hitsp and Min_hitsp

| MeanDecreaseGini | miRNA_ID |
|---|---|
| 1.27 | hsa-miR-6780a-5p |
| 1.14 | hsa-miR-490-3p |
| 0.75 | hsa-miR-483-5p |
| 0.72 | hsa-miR-5001-3p |
| 0.68 | hsa-miR-6515-5p |
| 0.68 | hsa-miR-548f-5p |
| 0.63 | hsa-miR-378b |

TABLE 46-continued

List of miRNAs detectable in plasma that is determined by random forest classification to be most useful in comparing Max_hitsp and Min_hitsp

| MeanDecreaseGini | miRNA_ID |
| --- | --- |
| 0.59 | hsa-miR-1291 |
| 0.56 | hsa-miR-2110 |
| 0.52 | hsa-miR-378f |
| 0.51 | hsa-miR-874-3p |
| 0.46 | hsa-miR-501-3p |
| 0.44 | hsa-miR-6740-5p |
| 0.44 | hsa-miR-1294 |
| 0.41 | hsa-miR-186-3p |
| 0.40 | hsa-miR-7706 |
| 0.39 | hsa-miR-3591-3p |
| 0.37 | hsa-miR-3180-5p |
| 0.36 | hsa-miR-4422 |
| 0.36 | hsa-miR-939-5p |
| 0.35 | hsa-miR-9-3p |
| 0.35 | hsa-miR-885-5p |
| 0.34 | hsa-miR-8061 |
| 0.32 | hsa-miR-1910-5p |
| 0.31 | hsa-miR-4448 |
| 0.30 | hsa-miR-490-5p |
| 0.25 | hsa-miR-4745-5p |
| 0.25 | hsa-miR-7113-5p |
| 0.24 | hsa-miR-5588-5p |
| 0.22 | hsa-miR-3617-5p |
| 0.22 | hsa-miR-129-2-3p |
| 0.21 | hsa-miR-4690-3p |
| 0.20 | hsa-miR-4659a-3p |
| 0.20 | hsa-miR-939-3p |
| 0.15 | hsa-miR-5004-3p |
| 0.12 | hsa-miR-6781-5p |
| 0.11 | hsa-miR-6509-3p |
| 0.10 | hsa-miR-935 |

TABLE 48

List of miRNAs detectable in plasma that is determined by random forest classification to be most useful in comparing samples from subjects with mild exposure to potentially injurious head impact (probability score of 0-0.1) and samples from subjects with least exposure to potentially injurious head impact (probability score of 0)

| MeanDecreaseGini | miRNA_ID |
| --- | --- |
| 3.46 | hsa-miR-218-5p |
| 2.86 | hsa-miR-183-5p |
| 2.70 | hsa-miR-18b-3p |
| 2.60 | hsa-miR-4436b-3p |
| 2.12 | hsa-miR-195-3p |
| 2.08 | hsa-miR-548as-3p |
| 1.74 | hsa-miR-6859-3p |
| 1.61 | hsa-miR-1291 |
| 1.57 | hsa-miR-590-5p |
| 1.54 | hsa-miR-3163 |
| 1.40 | hsa-miR-6850-5p |
| 1.36 | hsa-miR-214-3p |
| 1.36 | hsa-miR-3121-3p |
| 1.01 | hsa-miR-615-3p |
| 0.86 | hsa-miR-8061 |
| 0.85 | hsa-miR-4726-5p |

TABLE 50

List of miRNAs detectable in plasma that is determined by random forest classification to be most useful in comparing samples from subjects with moderate exposure potentially injurious head impact (probability score of 0.1-0.5) and samples from subjects with mild exposure potentially injurious head impact (probability score of 0-0.1)

| MeanDecreaseGini | miRNA_ID |
| --- | --- |
| 4.56 | hsa-miR-214-3p |
| 4.01 | hsa-miR-31-5p |
| 3.36 | hsa-miR-5583-3p |
| 2.27 | hsa-miR-4732-3p |
| 2.24 | hsa-miR-4726-5p |
| 2.07 | hsa-miR-193b-3p |
| 1.59 | hsa-miR-3194-3p |
| 1.58 | hsa-miR-5009-5p |
| 1.39 | hsa-miR-8061 |
| 1.30 | hsa-miR-615-3p |
| 1.03 | hsa-miR-455-5p |

TABLE 49

List of miRNAs detectable in plasma that is determined by random forest classification to be most useful in comparing samples from subjects with moderate exposure potentially injurious head impact (probability score of 0.1-0.5) and samples from subjects with least exposure potentially injurious head impact (probability score of 0)

| MeanDecreaseGini | miRNA_ID |
| --- | --- |
| 4.29 | hsa-miR-144-3p |
| 3.19 | hsa-miR-365a-3p = hsa-miR-365b-3p |
| 3.06 | hsa-miR-451a |
| 2.12 | hsa-miR-183-5p |
| 1.99 | hsa-miR-296-5p |
| 1.40 | hsa-miR-3158-5p |
| 1.40 | hsa-miR-3688-5p |
| 1.23 | hsa-miR-182-5p |
| 1.16 | hsa-miR-483-3p |
| 1.11 | hsa-miR-34c-5p |
| 1.06 | hsa-miR-218-5p |
| 1.05 | hsa-miR-590-5p |
| 1.00 | hsa-miR-885-5p |
| 0.79 | hsa-miR-6764-3p |
| 0.79 | hsa-miR-371b-5p |
| 0.74 | hsa-miR-106a-3p |
| 0.69 | hsa-miR-3163 |
| 0.66 | hsa-miR-503-3p |
| 0.64 | hsa-miR-1323 |
| 0.62 | hsa-miR-3121-3p |
| 0.62 | hsa-miR-7975 |
| 0.57 | hsa-miR-18b-3p |
| 0.49 | hsa-miR-512-3p |
| 0.49 | hsa-miR-6809-3p |
| 0.35 | hsa-miR-4657 |
| 0.33 | hsa-miR-1298-5p |
| 0.31 | hsa-miR-516b-5p |
| 0.29 | hsa-miR-3168 |
| 0.24 | hsa-miR-449b-5p |

TABLE 51

List of miRNAs detectable in plasma that is determined by random forest classification to be most useful in comparing samples from subjects with high exposure potentially injurious head impact (probability score of >0.5) and samples from subjects with least exposure potentially injurious head impact (probability score of 0)

| MeanDecreaseGini | miRNA_ID |
| --- | --- |
| 5.49 | hsa-miR-16-2-3p |
| 2.49 | hsa-miR-18b-3p |

TABLE 51-continued

List of miRNAs detectable in plasma that is determined by random forest classification to be most useful in comparing samples from subjects with high exposure potentially injurious head impact (probability score of >0.5) and samples from subjects with least exposure potentially injurious head impact (probability score of 0)

| MeanDecreaseGini | miRNA_ID |
|---|---|
| 2.12 | hsa-miR-144-5p |
| 1.99 | hsa-miR-144-3p |
| 1.74 | hsa-miR-4772-3p |
| 1.59 | hsa-miR-5695 |
| 1.58 | hsa-miR-4482-3p |
| 1.47 | hsa-miR-1226-3p |
| 1.46 | hsa-miR-183-5p |
| 1.45 | hsa-miR-3163 |
| 1.31 | hsa-miR-218-5p |
| 1.28 | hsa-miR-6820-5p |
| 1.21 | hsa-miR-320b |
| 1.14 | hsa-miR-7155-3p |
| 1.09 | hsa-miR-3160-3p |
| 0.98 | hsa-miR-135a-5p |
| 0.91 | hsa-miR-378b |
| 0.80 | hsa-miR-212-5p |
| 0.76 | hsa-miR-4654 |
| 0.64 | hsa-miR-4747-5p |
| 0.64 | hsa-miR-590-5p |
| 0.60 | hsa-miR-8072 |
| 0.51 | hsa-miR-548ac |
| 0.47 | hsa-miR-3160-5p |
| 0.35 | hsa-miR-6858-5p |

TABLE 53

List of miRNAs detectable in plasma that is determined by random forest classification to be most useful in comparing samples from subjects with high exposure potentially injurious head impact (probability score of >0.5) and samples from subject with moderate exposure potentially injurious head impact (probability score of 0.1-0.5)

| MeanDecreaseGini | miRNA_ID |
|---|---|
| 3.26 | hsa-miR-149-5p |
| 2.91 | hsa-miR-6820-5p |
| 2.28 | hsa-miR-211-5p |
| 2.24 | hsa-miR-4436b-3p |
| 2.19 | hsa-miR-6131 |
| 1.97 | hsa-miR-5009-5p |
| 1.96 | hsa-miR-6501-5p |
| 1.80 | hsa-miR-4747-5p |
| 1.74 | hsa-miR-8072 |
| 1.73 | hsa-miR-4443 |
| 1.72 | hsa-miR-4479 |
| 1.52 | hsa-miR-516a-5p |
| 1.45 | hsa-miR-512-3p |
| 1.30 | hsa-miR-516b-5p |
| 1.01 | hsa-miR-4745-5p |

TABLE 52

List of miRNAs detectable in plasma that is determined by random forest classification to be most useful in comparing samples from subjects with high exposure potentially injurious head impact (probability score of >0.5) and samples from subjects with mild exposure potentially injurious head impact (probability score of 0-0.1)

| MeanDecreaseGini | miRNA_ID |
|---|---|
| 3.46 | hsa-miR-6879-3p |
| 2.32 | hsa-miR-1291 |
| 1.88 | hsa-miR-4436b-3p |

TABLE 52-continued

List of miRNAs detectable in plasma that is determined by random forest classification to be most useful in comparing samples from subjects with high exposure potentially injurious head impact (probability score of >0.5) and samples from subjects with mild exposure potentially injurious head impact (probability score of 0-0.1)

| MeanDecreaseGini | miRNA_ID |
|---|---|
| 1.81 | hsa-miR-195-3p |
| 1.72 | hsa-miR-203a-3p |
| 1.69 | hsa-miR-6793-3p |
| 1.63 | hsa-miR-760 |
| 1.56 | hsa-miR-149-5p |
| 1.46 | hsa-miR-373-3p |
| 1.39 | hsa-miR-615-3p |
| 1.14 | hsa-miR-6820-5p |
| 1.06 | hsa-miR-3173-3p |
| 1.03 | hsa-miR-214-3p |
| 1.03 | hsa-miR-378g |
| 0.95 | hsa-miR-378b |
| 0.90 | hsa-miR-8072 |
| 0.88 | hsa-miR-455-5p |
| 0.64 | hsa-miR-8061 |

TABLE 54

List of miRNAs detectable in urine that is determined by random forest classification to be most useful in comparing High_freq_hits and Baseline

| MeanDecreaseGini | miRNA_ID |
|---|---|
| 1.95 | hsa-miR-500a-3p |
| 1.20 | hsa-miR-542-3p |
| 1.00 | hsa-miR-769-5p |
| 0.93 | hsa-miR-450a-5p |
| 0.93 | hsa-miR-451a |
| 0.78 | hsa-miR-222-5p |
| 0.76 | hsa-miR-148b-5p |
| 0.75 | hsa-miR-628-3p |
| 0.72 | hsa-miR-155-5p |
| 0.69 | hsa-miR-200c-3p |
| 0.66 | hsa-miR-7975 |
| 0.58 | hsa-miR-452-5p |
| 0.50 | hsa-miR-1298-5p |
| 0.45 | hsa-miR-194-3p |
| 0.27 | hsa-miR-4685-3p |

TABLE 57

List of miRNAs detectable in urine that is determined by random forest classification to be most useful in comparing Max_hitsp and Baseline

| MeanDecreaseGini | miRNA_ID |
|---|---|
| 0.93 | hsa-miR-210-3p |
| 0.73 | hsa-miR-187-3p |
| 0.60 | hsa-miR-320b |
| 0.51 | hsa-miR-203a-3p |
| 0.51 | hsa-miR-199a-3p = hsa-miR-199b-3p |
| 0.50 | hsa-miR-1307-3p |
| 0.48 | hsa-miR-664a-5p |
| 0.47 | hsa-miR-1307-5p |
| 0.41 | hsa-miR-200c-3p |
| 0.38 | hsa-miR-378c |
| 0.35 | hsa-miR-7706 |
| 0.32 | hsa-miR-148b-5p |
| 0.32 | hsa-miR-1226-5p |
| 0.31 | hsa-miR-3182 |
| 0.30 | hsa-miR-146b-3p |
| 0.27 | hsa-miR-769-5p |

TABLE 57-continued

List of miRNAs detectable in
urine that is determined by random
forest classification to be most useful in
comparing Max_hitsp and Baseline

| MeanDecreaseGini | miRNA_ID |
| --- | --- |
| 0.26 | hsa-miR-378a-3p |
| 0.26 | hsa-miR-6852-5p |
| 0.22 | hsa-miR-4448 |
| 0.22 | hsa-miR-374a-5p |
| 0.22 | hsa-miR-4326 |
| 0.20 | hsa-miR-211-5p |
| 0.14 | hsa-miR-7856-5p |
| 0.10 | hsa-miR-485-5p |
| 0.03 | hsa-miR-4466 |
| 0.02 | hsa-miR-939-5p |

TABLE 55

List of miRNAs detectable in
urine that is determined by random
forest classification to be most useful in
comparing High_freq_hits and
Low_freq_hits

| MeanDecreaseGini | miRNA_ID |
| --- | --- |
| 3.10 | hsa-miR-146b-3p |
| 2.48 | hsa-miR-149-5p |
| 1.83 | hsa-miR-769-5p |
| 1.68 | hsa-miR-4461 |
| 1.63 | hsa-miR-450a-5p |
| 1.26 | hsa-miR-616-5p |
| 1.05 | hsa-miR-3943 |
| 0.80 | hsa-miR-6723-5p |
| 0.40 | hsa-miR-4647 |

TABLE 56

List of miRNAs detectable in
urine that is determined by random
forest classification to be most useful in
comparing Low_freq_hits and Baseline

| MeanDecreaseGini | miRNA_ID |
| --- | --- |
| 2.11 | hsa-miR-130b-3p |
| 1.99 | hsa-miR-451a |
| 1.84 | hsa-miR-455-5p |
| 1.79 | hsa-miR-144-3p |
| 1.74 | hsa-miR-4685-3p |
| 1.73 | hsa-miR-486-5p |
| 1.60 | hsa-miR-452-5p |
| 1.47 | hsa-miR-1298-5p |
| 1.29 | hsa-miR-4449 |
| 1.27 | hsa-miR-4461 |
| 1.18 | hsa-miR-125b-1-3p |
| 1.15 | hsa-miR-190b |
| 1.06 | hsa-miR-33b-5p |
| 0.98 | hsa-miR-126-3p |
| 0.97 | hsa-miR-301b-3p |
| 0.96 | hsa-miR-148b-5p |
| 0.79 | hsa-miR-616-5p |
| 0.79 | hsa-miR-628-5p |
| 0.73 | hsa-miR-3168 |
| 0.55 | hsa-miR-191-3p |
| 0.54 | hsa-miR-3913-5p |
| 0.52 | hsa-miR-3913-3p |

TABLE 58

List of miRNAs detectable in
urine that is determined by random
forest classification to be most useful in
comparing Max_hitsp and Min_hitsp

| MeanDecreaseGini | miRNA_ID |
| --- | --- |
| 0.78 | hsa-miR-455-5p |
| 0.67 | hsa-miR-210-3p |
| 0.66 | hsa-miR-3182 |
| 0.61 | hsa-miR-320b |
| 0.56 | hsa-miR-210-5p |
| 0.53 | hsa-miR-203a-3p |
| 0.49 | hsa-miR-126-3p |
| 0.41 | hsa-miR-378c |
| 0.38 | hsa-miR-129-1-3p |
| 0.33 | hsa-miR-769-5p |
| 0.31 | hsa-miR-149-5p |
| 0.29 | hsa-miR-190a-5p |
| 0.29 | hsa-miR-122-5p |
| 0.29 | hsa-miR-320e |
| 0.29 | hsa-miR-1307-3p |
| 0.27 | hsa-miR-124-3p |
| 0.26 | hsa-miR-324-3p |
| 0.24 | hsa-miR-4448 |
| 0.22 | hsa-miR-3184-3p |
| 0.21 | hsa-miR-146b-3p |
| 0.20 | hsa-miR-378a-3p |
| 0.19 | hsa-miR-874-3p |
| 0.19 | hsa-miR-4443 |
| 0.19 | hsa-miR-184 |
| 0.15 | hsa-miR-199a-3p = hsa-miR-199b-3p |
| 0.15 | hsa-miR-98-3p |
| 0.11 | hsa-miR-92a-1-5p |
| 0.10 | hsa-miR-6852-5p |
| 0.07 | hsa-miR-769-3p |
| 0.06 | hsa-miR-1266-5p |
| 0.04 | hsa-let-7i-3p |
| 0.02 | hsa-miR-4466 |
| 0.02 | hsa-miR-23b-5p |

TABLE 60

List of miRNAs detectable in
urine that is determined by random
forest classification to be most useful in
comparing samples from subjects with
mild exposure to potentially injurious
head impact (probability score of 0-0.1)
and samples from subjects with least
exposure to potentially injurious head
impact (probability score of 0)

| MeanDecreaseGini | miRNA_ID |
| --- | --- |
| 2.57 | hsa-miR-1908-3p |
| 2.02 | hsa-miR-1226-3p |
| 1.62 | hsa-miR-1255a |
| 1.25 | hsa-miR-223-5p |
| 1.05 | hsa-miR-664a-5p |
| 1.02 | hsa-miR-892a |
| 0.99 | hsa-miR-532-3p |
| 0.97 | hsa-let-7c-5p |
| 0.84 | hsa-miR-500a-3p |
| 0.83 | hsa-miR-615-3p |
| 0.79 | hsa-miR-874-3p |
| 0.71 | hsa-miR-328-3p |
| 0.70 | hsa-miR-4443 |
| 0.68 | hsa-miR-320a |
| 0.65 | hsa-miR-4728-3p |
| 0.62 | hsa-let-7a-5p |
| 0.61 | hsa-miR-221-3p |
| 0.61 | hsa-miR-210-5p |
| 0.60 | hsa-miR-150-5p |
| 0.59 | hsa-miR-449c-5p |
| 0.48 | hsa-miR-708-5p |

TABLE 60-continued

List of miRNAs detectable in urine that is determined by random forest classification to be most useful in comparing samples from subjects with mild exposure to potentially injurious head impact (probability score of 0-0.1) and samples from subjects with least exposure to potentially injurious head impact (probability score of 0)

| MeanDecreaseGini | miRNA_ID |
|---|---|
| 0.43 | hsa-miR-296-3p |
| 0.42 | hsa-miR-1307-3p |
| 0.42 | hsa-miR-93-3p |
| 0.40 | hsa-miR-187-3p |
| 0.36 | hsa-miR-130b-5p |
| 0.35 | hsa-miR-4461 |
| 0.33 | hsa-miR-185-3p |
| 0.31 | hsa-miR-3605-5p |
| 0.29 | hsa-miR-449a |
| 0.29 | hsa-miR-122-5p |
| 0.28 | hsa-miR-502-3p |
| 0.28 | hsa-miR-501-5p |
| 0.24 | hsa-miR-320e |
| 0.24 | hsa-miR-7704 |
| 0.24 | hsa-miR-185-5p |
| 0.23 | hsa-miR-1304-3p |
| 0.23 | hsa-miR-148b-5p |
| 0.21 | hsa-miR-320c |
| 0.19 | hsa-miR-508-3p |
| 0.18 | hsa-miR-204-3p |
| 0.17 | hsa-miR-362-5p |
| 0.17 | hsa-miR-3064-5p |
| 0.16 | hsa-miR-92a-1-5p |
| 0.16 | hsa-miR-98-3p |
| 0.16 | hsa-miR-504-5p |
| 0.15 | hsa-miR-375 |
| 0.15 | hsa-miR-149-3p |
| 0.13 | hsa-miR-4510 |
| 0.12 | hsa-miR-410-3p |

TABLE 59

List of miRNAs detectable in urine that is determined by random forest classification to be most useful in comparing Min_hitsp and Baseline

| MeanDecreaseGini | miRNA_ID |
|---|---|
| 2.50 | hsa-let-7i-3p |
| 2.13 | hsa-miR-425-3p |
| 2.10 | hsa-miR-454-3p |
| 1.91 | hsa-miR-3184-5p |
| 1.80 | hsa-miR-455-3p |
| 1.59 | hsa-miR-224-5p |
| 1.38 | hsa-miR-126-3p |
| 1.38 | hsa-miR-374a-5p |
| 1.33 | hsa-miR-625-3p |
| 1.32 | hsa-miR-362-3p |
| 1.13 | hsa-miR-625-5p |
| 1.07 | hsa-miR-93-3p |
| 0.96 | hsa-miR-122-5p |
| 0.80 | hsa-miR-503-5p |
| 0.74 | hsa-miR-223-5p |
| 0.68 | hsa-miR-1306-3p |
| 0.63 | hsa-miR-338-5p |
| 0.45 | hsa-miR-199b-5p |
| 0.24 | hsa-miR-124-3p |

TABLE 61

List of miRNAs detectable in urine that is determined by random forest classification to be most useful in comparing samples from subjects with moderate exposure potentially injurious head impact (probability score of 0.1-0.5) and samples from subjects with least exposure potentially injurious head impact (probability score of 0)

| MeanDecreaseGini | miRNA_ID |
|---|---|
| 0.70 | hsa-miR-107 |
| 0.59 | hsa-miR-25-3p |
| 0.50 | hsa-let-7c-5p |
| 0.48 | hsa-miR-31-5p |
| 0.48 | hsa-miR-500a-3p |
| 0.47 | hsa-miR-320b |
| 0.46 | hsa-miR-331-3p |
| 0.44 | hsa-miR-328-3p |
| 0.39 | hsa-miR-423-3p |
| 0.37 | hsa-miR-181a-2-3p |
| 0.34 | hsa-miR-378c |
| 0.31 | hsa-miR-1307-3p |
| 0.29 | hsa-miR-517a-3p = hsa-miR-517b-3p |
| 0.28 | hsa-miR-708-5p |
| 0.28 | hsa-miR-1304-3p |
| 0.26 | hsa-miR-130b-3p |
| 0.26 | hsa-miR-301b-3p |
| 0.25 | hsa-miR-136-3p |
| 0.24 | hsa-miR-210-5p |
| 0.23 | hsa-miR-874-3p |
| 0.22 | hsa-miR-27a-3p |
| 0.21 | hsa-miR-1307-5p |
| 0.21 | hsa-miR-548i |
| 0.21 | hsa-miR-204-3p |
| 0.18 | hsa-miR-1323 |
| 0.17 | hsa-miR-152-5p |
| 0.17 | hsa-miR-574-3p |
| 0.16 | hsa-miR-187-3p |
| 0.15 | hsa-miR-221-3p |
| 0.14 | hsa-miR-653-5p |
| 0.14 | hsa-miR-199a-3p = hsa-miR-199b-3p |
| 0.14 | hsa-miR-532-3p |
| 0.14 | hsa-let-7a-5p |
| 0.14 | hsa-miR-148b-5p |
| 0.14 | hsa-miR-615-3p |
| 0.14 | hsa-miR-375 |
| 0.13 | hsa-miR-518a-3p |
| 0.13 | hsa-miR-502-3p |
| 0.13 | hsa-miR-378e |
| 0.13 | hsa-miR-125a-3p |
| 0.13 | hsa-miR-892a |
| 0.12 | hsa-miR-339-5p |
| 0.12 | hsa-miR-126-3p |
| 0.12 | hsa-miR-210-3p |
| 0.11 | hsa-miR-484 |
| 0.11 | hsa-miR-190a-5p |
| 0.11 | hsa-miR-410-3p |
| 0.10 | hsa-miR-223-5p |
| 0.10 | hsa-miR-584-5p |
| 0.10 | hsa-miR-664a-5p |
| 0.10 | hsa-miR-1269b |
| 0.10 | hsa-miR-3182 |
| 0.09 | hsa-miR-146b-3p |
| 0.09 | hsa-miR-512-3p |
| 0.09 | hsa-miR-3928-3p |
| 0.09 | hsa-miR-501-5p |
| 0.09 | hsa-miR-516a-5p |
| 0.08 | hsa-miR-184 |
| 0.08 | hsa-miR-1910-5p |
| 0.08 | hsa-miR-324-3p |
| 0.07 | hsa-miR-1226-3p |
| 0.07 | hsa-miR-143-3p |
| 0.07 | hsa-miR-199a-5p |
| 0.07 | hsa-miR-320a |
| 0.07 | hsa-miR-185-3p |
| 0.07 | hsa-miR-378a-3p |

TABLE 61-continued

List of miRNAs detectable in urine that is determined by random forest classification to be most useful in comparing samples from subjects with moderate exposure potentially injurious head impact (probability score of 0.1-0.5) and samples from subjects with least exposure potentially injurious head impact (probability score of 0)

| MeanDecreaseGini | miRNA_ID |
|---|---|
| 0.06 | hsa-miR-542-5p |
| 0.05 | hsa-miR-126-5p |
| 0.05 | hsa-miR-93-3p |
| 0.05 | hsa-miR-3158-3p |
| 0.05 | hsa-miR-4443 |
| 0.05 | hsa-miR-515-5p |
| 0.05 | hsa-miR-98-3p |
| 0.04 | hsa-miR-1283 |
| 0.04 | hsa-miR-888-5p |
| 0.03 | hsa-miR-26b-3p |
| 0.03 | hsa-miR-92a-1-5p |
| 0.03 | hsa-miR-188-5p |
| 0.03 | hsa-miR-3605-5p |
| 0.02 | hsa-miR-296-3p |
| 0.02 | hsa-miR-489-3p |
| 0.02 | hsa-miR-450a-5p |

TABLE 62

List of miRNAs detectable in urine that is determined by random forest classification to be most useful in comparing samples from subjects with moderate exposure potentially injurious head impact (probability score of 0.1-0.5) and samples from subjects with mild exposure potentially injurious head impact (probability score of 0-0.1)

| MeanDecreaseGini | miRNA_ID |
|---|---|
| 2.09 | hsa-miR-4461 |
| 1.96 | hsa-miR-4448 |
| 1.73 | hsa-miR-126-3p |
| 1.72 | hsa-miR-152-5p |
| 1.67 | hsa-miR-149-5p |
| 1.56 | hsa-let-7f-2-3p |
| 1.53 | hsa-miR-339-5p |
| 1.33 | hsa-miR-4326 |
| 0.77 | hsa-miR-1283 |
| 0.72 | hsa-miR-512-3p |
| 0.45 | hsa-miR-1226-3p |
| 0.35 | hsa-miR-122-5p |
| 0.22 | hsa-miR-1908-3p |
| 0.21 | hsa-miR-744-3p |
| 0.18 | hsa-miR-3913-3p |
| 0.15 | hsa-miR-518a-3p |
| 0.12 | hsa-miR-515-5p |
| 0.08 | hsa-miR-517a-3p = hsa-miR-517b-3p |

TABLE 64

List of miRNAs detectable in urine that is determined by random forest classification to be most useful in comparing samples from subjects with high exposure potentially injurious head impact (probability score of >0.5) and samples from subjects with mild exposure potentially injurious head impact (probability score of 0-0.1)

| MeanDecreaseGini | miRNA_ID |
|---|---|
| 1.89 | hsa-miR-338-5p |
| 1.52 | hsa-miR-4746-5p |
| 1.39 | hsa-miR-615-3p |
| 1.38 | hsa-miR-4448 |
| 1.38 | hsa-miR-138-5p |
| 1.35 | hsa-miR-3913-3p |
| 1.21 | hsa-miR-150-5p |
| 1.19 | hsa-miR-651-5p |
| 1.17 | hsa-miR-891a-5p |
| 1.16 | hsa-miR-3651 |
| 1.16 | hsa-miR-22-5p |
| 1.12 | hsa-miR-744-3p |
| 1.05 | hsa-miR-190a-3p |
| 0.84 | hsa-miR-1226-3p |
| 0.81 | hsa-miR-20a-5p |
| 0.81 | hsa-miR-146b-3p |
| 0.79 | hsa-miR-320a |
| 0.79 | hsa-miR-874-3p |
| 0.73 | hsa-miR-455-5p |
| 0.66 | hsa-miR-4728-3p |
| 0.61 | hsa-miR-323b-3p |
| 0.60 | hsa-miR-133a-3p |
| 0.39 | hsa-miR-199b-5p |
| 0.38 | hsa-miR-1911-5p |
| 0.37 | hsa-miR-1298-5p |
| 0.35 | hsa-miR-122-5p |

TABLE 63

List of miRNAs detectable in urine that is determined by random forest classification to be most useful in comparing samples from subjects with high exposure potentially injurious head impact (probability score of >0.5) and samples from subjects with least exposure potentially injurious head impact (probability score of 0)

| MeanDecreaseGini | miRNA_ID |
|---|---|
| 2.41 | hsa-miR-190a-5p |
| 1.38 | hsa-miR-365b-5p |
| 1.38 | hsa-miR-532-3p |
| 1.09 | hsa-miR-449c-5p |
| 0.95 | hsa-miR-653-5p |
| 0.89 | hsa-miR-628-5p |
| 0.72 | hsa-miR-891a-5p |
| 0.67 | hsa-miR-664a-5p |
| 0.63 | hsa-miR-362-5p |
| 0.62 | hsa-miR-708-5p |
| 0.62 | hsa-miR-98-3p |
| 0.61 | hsa-miR-149-3p |
| 0.55 | hsa-miR-148b-5p |
| 0.49 | hsa-miR-584-5p |
| 0.46 | hsa-miR-892a |
| 0.45 | hsa-miR-133a-3p |
| 0.43 | hsa-miR-501-5p |
| 0.43 | hsa-miR-489-3p |
| 0.42 | hsa-miR-199b-5p |
| 0.39 | hsa-miR-301b-3p |
| 0.37 | hsa-miR-4746-5p |
| 0.36 | hsa-miR-92a-2-5p |
| 0.34 | hsa-miR-4461 |
| 0.33 | hsa-miR-4488 |

TABLE 63-continued

List of miRNAs detectable in urine that is determined by random forest classification to be most useful in comparing samples from subjects with high exposure potentially injurious head impact (probability score of >0.5) and samples from subjects with least exposure potentially injurious head impact (probability score of 0)

| MeanDecreaseGini | miRNA_ID |
|---|---|
| 0.30 | hsa-miR-1911-5p |

TABLE 65

List of miRNAs detectable in urine that is determined by random forest classification to be most useful in comparing samples from subjects with high exposure potentially injurious head impact (probability score of >0.5) and samples from subject with moderate exposure potentially injurious head impact (probability score of 0.1-0.5)

| MeanDecreaseGini | miRNA_ID |
|---|---|
| 1.32 | hsa-miR-1307-3p |
| 0.73 | hsa-miR-339-5p |
| 0.63 | hsa-miR-149-5p |
| 0.62 | hsa-miR-574-3p |
| 0.60 | hsa-miR-185-3p |
| 0.57 | hsa-miR-331-3p |
| 0.49 | hsa-miR-199a-3p = hsa-miR-199b-3p |
| 0.46 | hsa-miR-204-3p |
| 0.42 | hsa-miR-877-5p |
| 0.41 | hsa-miR-324-5p |
| 0.41 | hsa-miR-27a-3p |
| 0.38 | hsa-miR-125a-3p |
| 0.37 | hsa-miR-4488 |
| 0.35 | hsa-miR-378a-3p |
| 0.34 | hsa-miR-328-3p |
| 0.32 | hsa-miR-320b |
| 0.29 | hsa-miR-378c |
| 0.26 | hsa-miR-187-3p |
| 0.25 | hsa-miR-138-5p |
| 0.23 | hsa-miR-324-3p |
| 0.23 | hsa-miR-326 |
| 0.23 | hsa-miR-1323 |
| 0.23 | hsa-miR-874-3p |
| 0.22 | hsa-miR-143-3p |
| 0.21 | hsa-miR-210-3p |
| 0.20 | hsa-miR-181a-3p |
| 0.19 | hsa-miR-126-5p |
| 0.18 | hsa-miR-378e |
| 0.18 | hsa-miR-126-3p |
| 0.16 | hsa-miR-516b-5p |
| 0.16 | hsa-miR-378d |
| 0.15 | hsa-miR-455-5p |
| 0.15 | hsa-miR-99a-5p |
| 0.15 | hsa-miR-320a |
| 0.12 | hsa-miR-517a-3p = hsa-miR-517b-3p |
| 0.12 | hsa-miR-9-5p |
| 0.11 | hsa-miR-515-5p |
| 0.11 | hsa-miR-1298-5p |
| 0.11 | hsa-miR-4461 |
| 0.10 | hsa-miR-516a-5p |
| 0.08 | hsa-miR-92a-2-5p |
| 0.08 | hsa-miR-615-3p |
| 0.07 | hsa-miR-146b-3p |
| 0.06 | hsa-miR-1911-5p |
| 0.05 | hsa-miR-1283 |
| 0.04 | hsa-miR-3913-5p |
| 0.03 | hsa-miR-512-3p |
| 0.01 | hsa-miR-199a-5p |

TABLE 66

| Comparison | Accuracy_test | AccuracyNull_test | Sensitivity_test | Specificity_test |
|---|---|---|---|---|
| High_freq_hits_vs_Baseline_with_5genes | 0.70 | 0.64 | 0.48 | 0.82 |
| High_freq_hits_vs_Low_freq_hits_with_4genes | 0.57 | 0.50 | 0.53 | 0.62 |
| Low_freq_hits_vs_Baseline_with_6genes | 0.71 | 0.64 | 0.51 | 0.82 |
| Max_hitsp_vs_Baseline_with_4genes | 0.69 | 0.69 | 0.40 | 0.83 |
| Max_hitsp_vs_Min_hitsp_with_4genes | 0.63 | 0.57 | 0.71 | 0.53 |
| Min_hitsp_vs_Baseline_with_15genes | 0.75 | 0.75 | 0.36 | 0.88 |
| Class1_vs_Class0_with_16genes | 0.81 | 0.64 | 0.61 | 0.91 |
| Class2_vs_Class0_with_19genes | 0.80 | 0.56 | 0.70 | 0.88 |
| Class2_vs_Class1_with_7genes | 0.73 | 0.58 | 0.76 | 0.68 |
| Class3_vs_Class0_with_16genes | 0.78 | 0.56 | 0.73 | 0.83 |
| Class3_vs_Class1_with_5genes | 0.79 | 0.58 | 0.85 | 0.70 |
| Class3_vs_Class2_with_15genes | 0.66 | 0.50 | 0.65 | 0.67 |

TABLE 67

| Comparison | Accuracy_test | AccuracyNull_test | Sensitivity_test | Specificity_test |
|---|---|---|---|---|
| High_freq_hits_vs_Baseline_with_5genes | 0.71 | 0.71 | 0.47 | 0.81 |
| High_freq_hits_vs_Low_freq_hits_with_4genes | 0.81 | 0.83 | 0.01 | 0.98 |
| Low_freq_hits_vs_Baseline_with_6genes | 0.81 | 0.83 | 0.00 | 0.98 |

TABLE 67-continued

| Comparison | Accuracy_test | AccuracyNull_test | Sensitivity_test | Specificity_test |
|---|---|---|---|---|
| Max_hitsp_vs_Baseline_with_4genes | 0.76 | 0.67 | 0.92 | 0.44 |
| Max_hitsp_vs_Min_hitsp_with_4genes | 0.82 | 0.83 | 0.26 | 0.94 |
| Min_hitsp_vs_Baseline_with_15genes | 0.82 | 0.83 | 0.19 | 0.95 |
| Class1_vs_Class0_with_16genes | 0.87 | 0.69 | 0.96 | 0.69 |
| Class2_vs_Class0_with_19genes | 0.92 | 0.71 | 0.79 | 0.97 |
| Class2_vs_Class1_with_7genes | 0.84 | 0.85 | 0.15 | 0.96 |
| Class3_vs_Class0_with_16genes | 0.84 | 0.85 | 0.15 | 0.97 |
| Class3_vs_Class1_with_5genes | 0.87 | 0.56 | 0.91 | 0.84 |
| Class3_vs_Class2_with_15genes | 0.83 | 0.73 | 0.50 | 0.96 |

What is claimed is:

1. A method of determining the risk of a subject developing a mild traumatic brain injury (mTBI) or the fitness of a subject to participate in an activity with chances of receiving a head impact, the method comprising:
obtaining a biological sample from the subject;
obtaining a control biological sample, wherein the control biological sample is selected from the group consisting of: a baseline sample of the subject and a matched sample from one or more different subjects;
measuring the biological sample from the subject for an amount of at least one microRNA marker selected from the microRNA markers hsa-miR-4732-5p and hsa-miR-1180-3p,
measuring the control biological sample for an amount of the at least one microRNA marker; and
comparing the amount of the at least one microRNA marker in the biological sample from the subject with the amount of the at least one microRNA marker in the control biological sample, wherein a change in the amount of the at least one microRNA marker in the biological sample from the subject compared with the control biological sample is indicative of the subject having a risk for mTBI or being unfit for participating in the activity with chances of receiving a head impact;
wherein decreased or increased amounts of hsa-miR-4732-5p microRNA, hsa-miR-1180-3p microRNA, or both in the biological sample from the subject is indicative of the subject being at risk for mTBI or unfit for participating in the activity with chances of receiving a head impact.

2. The method of claim 1, wherein a direction of change in the amount of the at least one microRNA marker from the subject compared with the control biological sample being the same as the direction of change indicated for the at least one microRNA marker, is indicative of the subject being at risk for mTBI or being unfit for participating in the activity with chances of receiving a head impact, wherein the at least one microRNA marker is selected from the microRNA markers hsa-miR-4732-5p and hsa-miR-1180-3p and having a change in expression wherein the expression of the at least one microRNA marker in the biological sample is increased relative to the expression of the at least one microRNA marker in the control biological sample.

3. The method of claim 1, wherein the biological sample from the subject and the control biological sample are plasma samples, and the at least one microRNA marker is selected from the microRNA markers.

4. The method of claim 1, wherein the control sample is from the subject's baseline sample, the at least one microRNA marker is selected from the microRNA markers hsa-miR-4732-5p and hsa-miR-1180-3p and having a change in expression wherein expression of the at least one microRNA marker is decreased relative to the expression of the at least one microRNA marker in the subject's baseline sample.

5. The method of claim 1, wherein the biological sample from the subject and the control biological sample are urine samples, and the microRNA marker is hsa-miR-1180-3p.

* * * * *